United States Patent
Chang et al.

(10) Patent No.: US 9,828,436 B2
(45) Date of Patent: Nov. 28, 2017

(54) ANTIBODIES AGAINST IMMUNOGENIC GLYCOPEPTIDES, COMPOSITIONS COMPRISING THE SAME AND USE THEREOF

(71) Applicant: Mackay Medical Foundation The Presbyterian Church In Taiwan Mackay Memorial Hospital, Taipei (TW)

(72) Inventors: Chih-long Chang, Taipei (TW); Chao-chih Wu, Taipei (TW)

(73) Assignee: MacKay Medical Foundation The Presbyterian Church In Taiwan MacKay Memorial Hospital, Taipei (TW)

(*) Notice: Subject to any disclaimer, the term of this patent is extended or adjusted under 35 U.S.C. 154(b) by 0 days.

(21) Appl. No.: 15/126,945

(22) PCT Filed: Mar. 19, 2015

(86) PCT No.: PCT/US2015/021413
§ 371 (c)(1),
(2) Date: Sep. 16, 2016

(87) PCT Pub. No.: WO2015/143123
PCT Pub. Date: Sep. 24, 2015

(65) Prior Publication Data
US 2017/0107297 A1   Apr. 20, 2017

Related U.S. Application Data

(60) Provisional application No. 61/955,216, filed on Mar. 19, 2014.

(51) Int. Cl.
*A61K 39/395* (2006.01)
*C07K 16/30* (2006.01)
*A61K 45/06* (2006.01)
*A61K 39/00* (2006.01)

(52) U.S. Cl.
CPC .... *C07K 16/3076* (2013.01); *A61K 39/39558* (2013.01); *A61K 45/06* (2013.01); *C07K 16/3069* (2013.01); *A61K 2039/505* (2013.01); *C07K 2317/24* (2013.01); *C07K 2317/565* (2013.01); *C07K 2317/73* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,736,142 A | 4/1998 | Sette et al. |
| 6,413,935 B1 | 7/2002 | Sette et al. |
| 6,544,952 B1 | 4/2003 | Danishefsky et al. |
| 8,158,367 B2 | 4/2012 | Wong et al. |
| 8,268,969 B2 | 9/2012 | Wong et al. |
| 2001/0048929 A1 | 12/2001 | Chong et al. |
| 2003/0157115 A1 | 8/2003 | Bay et al. |
| 2005/0033030 A1 | 2/2005 | Lo et al. |
| 2005/0049197 A1 | 3/2005 | Sette et al. |
| 2007/0083334 A1 | 4/2007 | Mintz et al. |
| 2007/0178095 A1 | 8/2007 | Smith et al. |
| 2008/0299126 A1 | 12/2008 | Han et al. |
| 2009/0136526 A1 | 5/2009 | McDonagh et al. |
| 2009/0252748 A1 | 10/2009 | Mi et al. |
| 2010/0008954 A1 | 1/2010 | Wong et al. |
| 2011/0117085 A1 | 5/2011 | Rotem-Yehudar et al. |
| 2011/0229510 A1 | 9/2011 | Danishefsky et al. |
| 2011/0236934 A1 | 9/2011 | Samain et al. |
| 2011/0245100 A1 | 10/2011 | Yarranton et al. |
| 2011/0250202 A1 | 10/2011 | Cote et al. |
| 2011/0256154 A1 | 10/2011 | Vincent et al. |
| 2012/0238729 A1 | 9/2012 | Kuramochi et al. |
| 2012/0244142 A1 | 9/2012 | Kimura et al. |
| 2012/0328646 A1 | 12/2012 | Wong et al. |
| 2013/0095173 A1 | 4/2013 | Danishefsky et al. |
| 2013/0209471 A1 | 8/2013 | Schwarz et al. |
| 2013/0236486 A1 | 9/2013 | Boons et al. |
| 2013/0315911 A1 | 11/2013 | Stevens et al. |
| 2014/0193427 A1 | 7/2014 | Lerner et al. |
| 2016/0264684 A1 | 9/2016 | da Silva et al. |
| 2016/0362498 A1 | 12/2016 | Zhang et al. |

FOREIGN PATENT DOCUMENTS

| | | |
|---|---|---|
| WO | 2014107652 A2 | 7/2014 |
| WO | 2015143126 A2 | 9/2015 |
| WO | 2015157629 A2 | 10/2015 |

(Continued)

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Written Opinion of the International Searching Authority for PCT/US2015/021413, dated Sep. 24, 2015.
Hung et al., "A monoclonal anti-Globo H antibody, VK9, can mediate CDC/ADCC and inhibit adhesion of Globo H+ cancer cells to extracellular matrix," Cancer Res 72: abstract 2529; Apr. 15, 2012.

(Continued)

*Primary Examiner* — Laura B Goddard
*Assistant Examiner* — Meera Natarajan
(74) *Attorney, Agent, or Firm* — Fisherbroyles LLP; Adam Whiting

(57) ABSTRACT

Disclosed herein are antibodies which specifically bind to at least one epitope defined by the immunogenic glycopeptide. Other aspects of the present disclosure are pharmaceutical composition comprising the antibody; and method for preventing and/or treating Globo-H-positive cancer.

20 Claims, 17 Drawing Sheets

(56) References Cited

FOREIGN PATENT DOCUMENTS

WO 2015159118 A2 10/2015

OTHER PUBLICATIONS

Sarkar, Sourav, "Synthesis and Study of Anti-tumor Vaccines," Doctoral Dissertation, University of Toledo, Dec. 2012.

Hevey et al., "Recent advances in developing synthetic carbohydrate-based vaccines for cancer immunotherapies," Future Med. Chem. (2012) 4(4), 545-584.

Wang et al., "Polyclonal antibodies from patients immunized with a globo H-keyhole limpet hemocyanin vaccine Isolation, quantification, and characterization of immune responses by using totally synthetic immobilized tumor antigens," PNAS (Mar. 14, 2000), vol. 97, No. 6, 2719-2724.

Wang et al., "Glycan microarray of Globo H and related structures for quantitative analysis of breast cancer," PNAS, Aug. 19, 2008, vol. 105, No. 33: 11661-11666.

Chang et al., "Expression of Globo H and SSEA3 in breast cancer stem cells and the involvement of fucosyl transferases 1 and 2 in Globo H synthesis," PNAS, Aug. 19, 2008, vol. 105, No. 33: 11667-11672.

Eller et al., "Affinity of monoclonal antibodies for Globo-series glycans," Carbohydr Res. Oct. 9, 2014; 397: 1-6. doi:10.1016/j.carres.2014.07.003.

Go et al., "Synthesis of a Trimeric gp120 Epitope Mimic Conjugated to a THelper Peptide to Improve Antigenicity," J Am Chem Soc. Mar. 16, 2011; 133(10): 3230-3233. doi:10.1021/ja1083915.

Jeon et al., "A Practical Total Synthesis of Globo-H for Use in Anticancer Vaccines," J Org Chem. Nov. 6, 2009; 74(21): 8452-8455. doi:10.1021/jo901682p.

Buskas et al., "Immunotherapy for Cancer: Synthetic Carbohydrate-based Vaccines," Chem Commun (Camb). Sep. 28, 2009; (36): 5335-5349. doi:10.1039/b908664c.

Zhu et al., "From Synthesis to Biologics: Preclinical Data on a Chemistry Derived Anticancer Vaccine," J Am Chem Soc. Jul. 8, 2009; 131(26): 9298-9303. doi:10.1021/ja901415s.

Alexander et al., "Linear PADRE T Helper Epitope and Carbohydrate B Cell Epitope Conjugates Induce Specific High Titer IgG Antibody Responses," The Journal of Immunology, 2000, 164: 1625-1633.

Slovin et al., "Carbohydrate vaccines as immunotherapy for cancer," Immunology and Cell Biology (2005) 83, 418-428. doi:10.1111/j.1440-1711.2005.01350.x.

Adamo et al., "Synthetically defined glycoprotein vaccines: current status and future directions," Chem. Sci., 2013, 4, 2995.

Wilson et al., "Synthetic Carbohydrate-Based Tumor Vaccines," In Carbohydrate-Based Vaccines; Roy, R.; ACS Symposium Series; American Chemical Society: Washington, DC, 2008. Publication Date: Jul. 2, 2008 | doi: 10.1021/bk-2008-0989.ch012.

Danishefsky et al., "Development of Globo-H Cancer Vaccine," Acc. Chem. Res. 2015, 48, 643-652. DOI: 10.1021/ar5004187.

Kuduk et al., "Synthetic and immunological studies on clustered modes of mucin-related Tn and TF O-linked antigens: the preparation of a glycopeptide-based vaccine for clinical trials against prostate cancer," J Am Chem Soc. 1998;120:12474-12485.

Ingale et al., "Robust immune responses elicited by a fully synthetic three-component vaccine," Nat Chem Biol. Oct. 2007; 3(10):663-7. Epub Sep. 2, 2007.

Slovin et al., "Fully synthetic carbohydrate-based vaccines in biochemically relapsed prostate cancer: clinical trial results with alpha-N-acetylgalactosamine-O-serine/threonine conjugate vaccine," J Clin Oncol. 2003;21:4292-4298.

\* cited by examiner

A.

B.

ANTIBODIES AGAINST IMMUNOGENIC GLYCOPEPTIDES, COMPOSITIONS COMPRISING THE SAME AND USE THEREOF

FIELD OF THE INVENTION

The present invention relates to the field of immunotherapy of cancer. More particularly, the disclosed invention relates to an antibody against an immunogenic glycopeptide, a pharmaceutical composition comp comprising the antibody and to the use thereof in cancer therapy.

BACKGROUND OF THE INVENTION

Globo H is a hexasaccharide and belongs to a large number of tumor-associated carbohydrate antigens that are overexpressed on the surface of various epithelial cancer cells, including breast, colon, ovarian, pancreatic, lung, and prostate cancer cells. The aberrant expression of Globo H renders it an attractive candidate for immunotherapy and the development of cancer vaccines for Globo H-positive cancers.

However, like most carbohydrate antigens, Globo H is often tolerated by the immune system, and consequently, the immunogenicity induced by Globo H is limited. Further, the production of antibody against a specific immunogen typically involves the cooperative interaction of two types of lymphocytes, B-cells and helper T-cells. Yet, Globo H alone cannot activate helper T-cells, which also attributes to the poor immunogenicity of Globo H. Accordingly, the immunization with Globo H is often typified by low titer of immunoglobulin M (IgM) and failure to class switch to immunoglobulin G (IgG), as well as ineffective antibody affinity maturation.

Various approaches have been developed to address the above-mentioned deficiencies. In certain researches, foreign carrier proteins or peptides having T-epitopes (such as keyhole limpet hemocyanin (KLH) or detoxified tetanus toxoid (TT)) have been conjugated with carbohydrate antigens hoping to enhance the immunogenicity of the carbohydrate antigens. US 20010048929 provided a multivalent immunogenic molecule, comprising a carrier molecule containing at least one functional T-cell epitope, and multiple different carbohydrate fragments each linked to the carrier molecule and each containing at least one functional B-cell epitope, wherein said carrier molecule imparts enhanced immunogenicity to said multiple carbohydrate fragments and wherein the carbohydrate fragment is Globo H, LeY or STn. US 20120328646 provides a carbohydrate based vaccine containing Globo H (B cell epitope) chemically conjugated to the immunogenic carrier diphtheria toxin cross-reacting material 197 (DT-CRM 197) (Th epitope) via a p-nitrophenyl linker, which provides immunogenicity in breast cancer models, showing delayed tumorigenesis in xenograft studies. US 20120263749 relates to a polyvalent vaccine for treating cancer comprising at least two conjugated antigens selected from a group containing glycolipid antigen such as Globo H, a Lewis antigen and a ganglioside, polysaccharide antigen, mucin antigen, glycosylated mucin antigen and an appropriate adjuvant.

Nonetheless, conjugation of carbohydrates to a carrier protein poses several new problems. According to Ingale et al., the foreign carrier protein and the linker for attaching the carrier protein and the carbohydrate may elicit strong B-cell responses, thereby leading to the suppression of an antibody response against the carbohydrate epitope (Ingale S. et al. *Robust immune responses elicited by a fully synthetic three-component vaccine. Nat Chem Biol.* 2007 October; 3(10): 663-7. Epub 2007 Sep. 2). Furthermore, Ingale et al. also indicated that the conjugation chemistry is difficult to control, resulting in conjugates with ambiguities in composition and structure, which may affect the reproducibility of an immune response. Considering the above-mentioned factors, Ingale et al. concluded that it is not surprising that preclinical and clinical studies using carbohydrate-protein conjugates have led to mixed results. For example, Kuduk et al. taught that the immunization with a trimeric cluster of Tn-antigens conjugated to KLH in the presence of the adjuvant QS-21 elicited modest titers of IgG antibodies in mice (Kuduk S D, et al. *Synthetic and immunological studies on clustered modes of mucin-related Tn and TF O-linked antigens: the preparation of a glycopeptide-based vaccine for clinical trials against prostate cancer. J Am Chem Soc.* 1998; 120:12474-12485); while Slovin et al. taught that the same vaccine gave low median IgG and IgM antibody titers in a clinical trial of relapsed prostate cancer patients (Slovin S F, et al. *Fully synthetic carbohydrate-based vaccines in biochemically relapsed prostate cancer: clinical trial results with alpha-N-acetylgalactosamine-O-serine/threonine conjugate vaccine. J Clin Oncol.* 2003; 21:4292-4298).

Moreover, for cancer patients with hypoimmune status; particular in patients receiving chemotherapy or radiation therapy, as well as late-stage cancer patients, the efficacy of active immune intervention is often limited, for these patients may not be able to produce sufficient antibodies to elicit the anti-tumor effect.

In view of the foregoing, there exists a need in the art for developing alternative strategies for improving the immunization and/or therapeutic efficacy of carbohydrate-based vaccines.

SUMMARY OF THE INVENTION

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is directed to an antibody which specifically binds to Globo H according to any of the above-mentioned aspect/embodiments of the present disclosure.

According to certain embodiments, the antibody is a monoclonal antibody.

According to optional embodiments, the antibody is a chimeric or humanized antibody.

In still another aspect, the present disclosure is directed to a pharmaceutical composition for treating a cancer in a subject in need thereof.

According to one embodiment of the present disclosure, the pharmaceutical composition comprises (1) a therapeutically effective amount of the antibody according to any of the above-mentioned aspects/embodiments of the present disclosure, and optionally (2) a pharmaceutically acceptable carrier.

In still yet another aspect, the present disclosure is directed to a method of treating a cancer in a subject in need thereof.

According to embodiments of the present disclosure, the method includes administering to the subject the pharmaceutical composition the antibody or pharmaceutical composition according to any of the above-mentioned aspects/embodiments of the present disclosure.

DETAILED DESCRIPTION OF THE INVENTION

Figure 1:
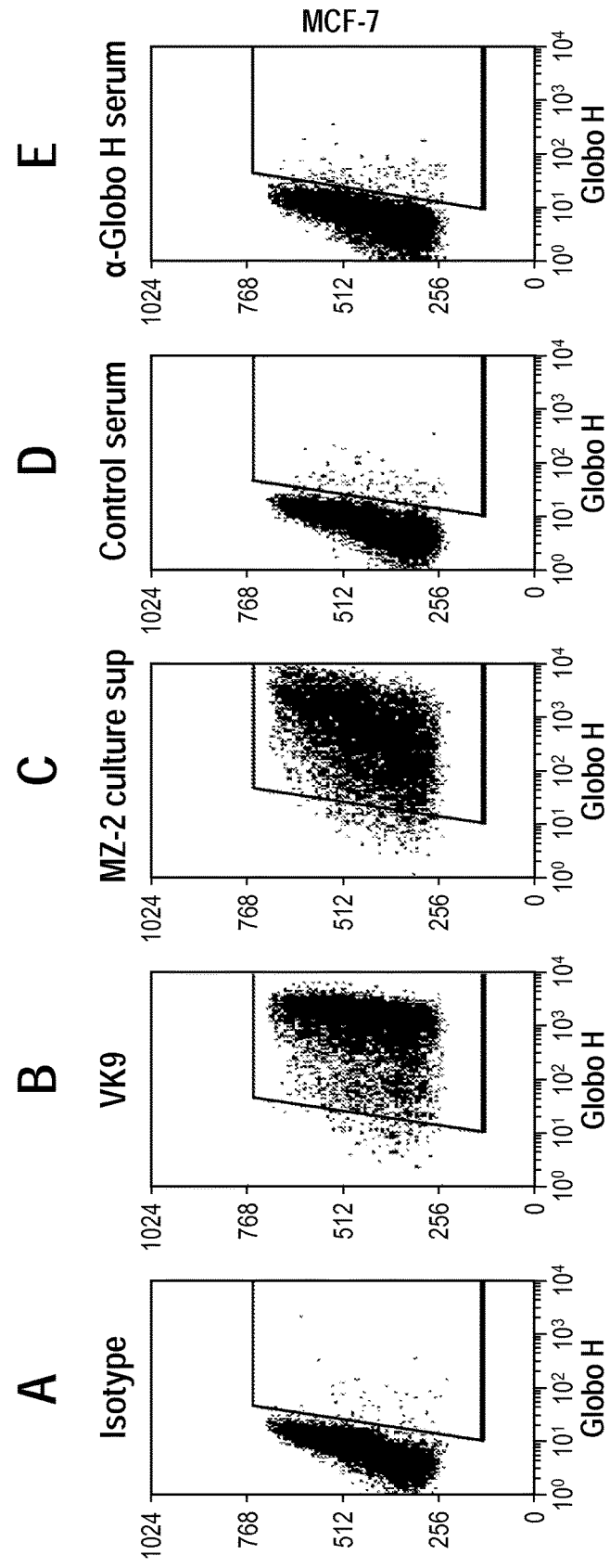
FIGS. 1A to E illustrate results of cell binding assay (A: Isotype; B: VK9; C: MZ-2; D: Control serum; E: α-Globo H serum).

The present invention is based, at least, on the finding that recombinant antibodies specifically bind to Globo H for treating cancer expression tumor-associated carbohydrate antigens.
Definition Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antigen" as used herein is defined as a substance capable of eliciting an immune response. Said immune response may involve either antibody production, or the activation of specific immunologically-competent cells, or both. As used herein, the term "immunogen" refers to an antigen capable of inducing the production of an antibody. Also, the term "immunogenicity" generally refers to the ability of an immunogen or antigen to stimulate an immune response.

The term "epitope" refers to a unit of structure conventionally bound by an immunoglobulin VH/VL pair. An epitope defines the minimum binding site for an antibody, and thus represent the target of specificity of an antibody.

The term "antibody" as used herein refers to a whole antibody molecule or a fragment, variant or derivative thereof, which is capable of recognizing or binding to an antigen. Most natural antibodies have two heavy chains and two light chains linked to each other by disulfide bonds. The light chain includes a variable domain (VL) and a constant domain (CL); while the heavy chain includes a variable domain (VH) and three constant domains (CH1, CH2 and CH3, collectively referred to as CH). The variable regions of both light (VL) and heavy (VH) chains determine binding recognition and specificity to the antigen. The VH and VL regions can be further subdivided into regions of hypervariability, termed complementarity determining regions (CDR), interspersed with regions that are more conserved, termed framework regions (FR). Each VH and VL is, composed of three CDRs and four FRs arranged from amino-terminus to carboxy-terminus in the following order: FR1, CDR1, FR2, CDR2, FR3, CDR3, FR4. The constant region domains of the light (CL) and heavy (CH) chains confer important biological properties such as antibody chain association, secretion, trans-placental mobility, complement binding, and binding to Fc receptors (FcR).

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). According to the methods used herein, the amino acid positions assigned to CDRs and FRs can be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs), i.e., CDR1, CDR2, and CDR3) refers to the amino acid residues of an antibody variable domain the presence of which are necessary for antigen binding. Each variable domain typically has three CDR regions identified as CDR1, CDR2 and CDR3. H-CDR refers to the CDR of the heavy chain and L-CDR refers to the CDR of the light chain.

As used herein, the term "monoclonal antibody" refers to an antibody molecule obtained from a single type of antibody-producing cells.

The term "chimeric antibody" refers to an antibody comprising a variable region from one source or species and at least a portion of a constant region derived from a different source or species, usually prepared by recombinant DNA techniques. It is preferred that the CDRs of a chimeric antibody have one origin, while the remainder of the antibody has a different origin. In particular, in the present invention the chimeric antibody may be a humanized antibody in which the antigen binding sequences/variable domains of a non-human antibody have been grafted onto human antibody framework regions.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The humanized forms of rodent antibodies will essentially comprise the same CDR sequences of the parental rodent antibodies, although certain amino acid substitutions may be included to increase affinity, increase stability of the humanized antibody, or for other reasons. However, as CDR loop exchanges do not uniformly result in an antibody with the same binding properties as the antibody of origin, changes in framework residues (FR), residues involved in CDR loop support, might also be introduced in humanized antibodies to preserve antigen binding affinity.

Unless specified otherwise, in the peptide notation used herein, the left-hand direction is the amino-terminal (N-terminal) direction and the right-hand direction is the carboxy-terminal (C-terminal) direction, in accordance with standard usage and convention.

"Percentage (%) amino acid sequence identity" with respect to the amino acid sequences identified herein is defined as the percentage of amino acid residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). Specifically, the percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

As discussed herein, minor variations in the amino acid sequences of proteins/polypeptides are contemplated as being encompassed by the presently disclosed and claimed inventive concept(s), providing that the variations in the amino acid sequence maintain at least 80% such as at least, 81%, 82%, 83%, 84%, 85%, 86%, 87%, 88%, 89%, 90%, 91%, 92%, 93%, 94%, 95%, 96%, 97%, 98% and 99%. In particular, conservative amino acid replacements are contemplated. Conservative replacements are those that take place within a family of amino acids that are related in their side chains. Genetically encoded amino acids are generally divided into families: (1) acidic aspartate, glutamate; (2) basic lysine, arginine, histidine; (3) nonpolar alanine, valine, leucine, isoleucine, proline, phenylalanine, methionine, tryptophan; and (4) uncharged polar glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of proteins/polypeptides can be readily prepared by those of ordinary skill in the art. Preferred amino- and carboxy-termini of fragments or analogs occur near boundaries of functional domains.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

As used herein, the term "antigen-binding portion" of an antibody (or simply "antigen portion"), refers to full length or one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR), or any fusion proteins comprising such antigen-binding portion.

Unless contrary to the context, the term "treatment" are used herein broadly to include a preventative (e.g., prophylactic), curative, or palliative measure that results in a desired pharmaceutical and/or physiological effect. Preferably, the effect is therapeutic in terms of partially or completely curing or preventing cancer. Also, the terms "treatment" and "treating" as used herein refer to application or administration of the present immunogenic glycopeptide, antibody, or pharmaceutical composition comprising any of the above to a subject, who has cancer, a symptom of cancer, a disease or disorder secondary to cancer, or a predisposition toward cancer, with the purpose to partially or completely alleviate, ameliorate, relieve, delay onset of, inhibit progression of, reduce severity of, and/or reduce incidence of one or more symptoms or features of cancer. Generally, a "treatment" includes not just the improvement of symptoms or decrease of markers of the disease, but also a cessation or slowing of progress or worsening of a symptom that would be expected in absence of treatment. The term "treating" can also be used herein in a narrower sense which refers only to curative or palliative measures intended to ameliorate and/or cure an already present disease state or condition in a patient or subject.

The term "preventing" as used herein refers to a preventative or prophylactic measure that stops a disease state or condition from occurring in a patient or subject. Prevention can also include reducing the likelihood of a disease state or condition from occurring in a patient or subject and impeding or arresting the onset of said disease state or condition.

The term "effective amount" as used herein refers to the quantity of a component which is sufficient to yield a desired response. Effective amount may be expressed, for example, in grams, milligrams or micrograms or as milligrams per kilogram of body weight (mg/kg). The term also refers to an amount of a pharmaceutical composition containing an active component or combination of components. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives.

As used herein, the term "therapeutically effective amount" refers to the quantity of an active component which is sufficient to yield a desired therapeutic response. A therapeutically effective amount is also one in which any toxic or detrimental effects of the compound or composition are outweighed by the therapeutically beneficial effects.

As used herein, a "pharmaceutically acceptable carrier" is one that is suitable for use with the subjects without undue adverse side effects (such as toxicity, irritation, and allergic response) commensurate with a reasonable benefit/risk ratio. Also, each carrier must be "acceptable" in the sense of being compatible with the other ingredients of the pharmaceutical composition. The carrier can be in the form of a solid, semi-solid, or liquid diluent, cream or a capsule. The carrier must be "acceptable" in the sense of being compatible with the other ingredients of the formulation, and is selected to minimize any degradation of the active agent and to minimize any adverse side effects in the subject.

The term "subject" refers to a mammal including the human species that is treatable with antibody. The term "subject" is intended to refer to both the male and female gender unless one gender is specifically indicated.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Antibodies for Prevention and/or Treatment Cancer

Provided herein are novel recombinant anti-Globo H antibodies and anti-Globo H-binding peptides specifically binding to Globo H or its derivatives, and methods of their use in anti-tumor immunotherapies, such as the treatment of cancer. Once bound to a cancer antigen, antibodies can induce antibody-dependent cell-mediated cytotoxicity, activate the complement system, and prevent a receptor interacting with its ligand (such as Globo H). In one embodiment, the compositions comprising the anti-Globo H-binding peptides or anti-Globo H antibodies described herein are useful in anti-cancer therapies. Furthermore, the compositions comprising the anti-Globo H-binding peptides or anti-Globo H antibodies can combine with an additional anti-tumor agent. In particular, the present embodiments provide the complementarity determining region (CDR) sequences of specific anti-Globo H antibodies, which can be used in a variety of anti-Globo H-binding peptides. In particular, the present invention provides a humanized or chimeric antibody or an antigen-binding fragment thereof capable of binding to Globo H or its derivatives.

In one aspect, the present invention provides an isolated anti-Globo H antibody or an antigen-binding portion thereof, comprising at least one of a heavy chain complementarity determining region 1 (H-CDR1) consisting of the amino acid residues of GFSLSTFDMGVG (SEQ ID NO: 1), GSSLSTFDVGVG (SEQ ID NO: 2), GFSLGTFDLGIG (SEQ ID NO: 3), GFSLSTFDLGIG (SEQ ID NO: 4) or a variant having amino acid sequence with at least 80% identity to any of SEQ ID NOs: 1 to 4; a heavy chain CDR2 (H-CDR2) consisting of the amino acid residues of HIWWDDDKYYNPA (SEQ ID NO:5), HIWGDDDKYYNPA (SEQ ID NO: 6) or a variant having amino acid sequence with at least 80% identity to any of SEQ ID NOs: 5 and 6; and a heavy chain CDR3 (H-CDR3) consisting of the amino acid residues of LYGNYLTSFYCDY (SEQ ID NO: 7), or LSGNYLTSFYCDY (SEQ ID NO: 8), LYGNYLRSYYCDY (SEQ ID NO: 9) or a variant having amino acid sequence with at least 80% identity to any of SEQ ID NOs: 7 to 9; and at least one of a light chain CDR1 (L-CDR1) consisting of the amino acid residues of SASSSVSYMH (SEQ ID NO: 10), SASSRVSYMH (SEQ ID NO:11), SARSSVSYMH (SEQ ID NO:12), RASSSVSYMH (SEQ ID NO:13) or a variant having amino acid sequence with at least 80% identity to any of SEQ ID NOs: 10 to 13; a light chain CDR2 (L-CDR2) consisting of the amino acid residues of ATSNLAS (SEQ ID NO:14), WTSDRYS (SEQ ID NO:15), DTSKLAS (SEQ ID NO:16) or a variant having amino acid sequence with at least 80% identity to any of SEQ ID NOs: 14 to 16; and a light chain CDR3 (L-CDR3) consisting of the amino acid residues QQWSSNPFT (SEQ ID NO: 17), QQWSSNPLT (SEQ ID NO: 18), QQHLHIPYT (SEQ ID NO: 19) or a variant having amino acid sequence with at least 80% identity to any of SEQ ID NOs: 17 to 19; such that said isolated antibody or antigen-binding portion thereof binds to Globo H. Preferably, the sequence identity as mentioned above is at least 81%, 82%, 83%, 84%, 85%, 86%, 87%, 88%, 89%, 90%, 91%, 91%, 92%, 93%, 94%, 95%, 96%, 97%, 98% or 99%.

In a further embodiment, the present invention provides an isolated anti-Globo H antibody or an antigen-binding portion thereof, comprising (i) a heavy chain variable region comprising a heavy chain variable region comprising H-CDR1 selected from the group consisting of SEQ ID NOs: 1 to 4, H-CDR2 selected from the group consisting of SEQ ID NOs: 5 and 6 and H-CDR3 selected from the group consisting of SEQ ID NOs: 7 to 9, and (ii) light chain variable regions comprising L-CDR1 selected from the group consisting of SEQ ID NOs: 10 to 13, L-CDR2 selected from the group consisting of SEQ ID NOs: 14 to 16 and L-CDR3 selected from the group consisting of SEQ ID NOs: 17 to 19. Preferably, H-CDR1 is SEQ ID NO:3; H-CRD2 is SEQ ID NO:5; H-CDR3 is SEQ ID NO:8; L-CDR1 is SEQ ID NO:10; L-CDR2 is SEQ ID NO:16; and L-CDR3 is SEQ ID NO:18.

In further embodiments, H-CDR1 has the amino acid sequence of SEQ ID NO:3 or SEQ ID NO:4; H-CDR2 has the amino acid sequence of SEQ ID NO:5; H-CDR3 has the amino acid sequence of SEQ ID NO: 8; L-CDR1 has the amino acid sequence of SEQ ID NO:12; L-CDR2 has the amino acid sequence of SEQ ID NO:16 and L-CDR3 has the amino acid sequence of SEQ ID NO:18.

In one aspect, the present invention provides a heavy chain variable region comprising a heavy chain variable region comprising H-CDR1 selected from the group consisting of SEQ ID NOs: 1 to 4, H-CDR2 selected from the group consisting of SEQ ID NOs: 5 and 6 and H-CDR3 selected from the group consisting of SEQ ID NOs: 7 to 9. In a further embodiment, the present invention provides a heavy chain variable region comprising SEQ ID NO: 3 as H-CDR1, SEQ ID NO: 5 H-CDR2 and SEQ ID NO: 8 as H-CDR3.

In one aspect, the present invention provides a light chain variable region comprising L-CDR1 selected from the group consisting of SEQ ID NOs: 10 to 13, L-CDR2 selected from the group consisting of SEQ ID NOs: 14 to 16 and L-CDR3 selected from the group consisting of SEQ ID NOs: 17 to 19. In a further embodiment, the present invention provides a light chain variable region comprising SEQ ID NO: 12 as L-CDR1, SEQ ID NO: 16 as L-CDR2 and SEQ ID NO: 18 as L-CDR3.

In one embodiment, the isolated anti-Globo H antibody is a monocloncal antibody. Monoclonal antibodies to Globo H can be made according to knowledge and skill in the art. For example, it can be made by injecting test subjects with Globo H conjugate of the invention and then isolating hybridomas expressing antibodies having the desired sequence or functional characteristics.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the conventional techniques known in the art; for example, the isolation of murine and human antibodies, respectively, using phage libraries. Subsequent publications describe the production of high affinity (nM range) human antibodies by chain shuffling, as well as combinatorial infection and in vivo recombination as a strategy for constructing very large phage libraries. Thus, these techniques are viable alternatives to traditional monoclonal antibody hybridoma techniques for isolation of monoclonal antibodies.

In one embodiment, the present invention provides an isolated anti-Globo H antibody, comprising (i) a heavy chain variable region comprising an amino acid sequence having at least 85% identical to any of the amino acid sequences of SEQ ID NOs: 140 to 163, and (ii) a light chain variable region comprising an amino acid sequence having at least 80% identical to any of the amino acid sequence of SEQ ID NO: 164 to 199. Preferably, the sequence identity as mentioned above is at least 90%, 91%, 91%, 92%, 93%, 94%, 95%, 96%, 97%, 98% or 99%.

In one embodiment, the present invention provides an isolated anti-Globo H antibody, comprising (i) a heavy chain variable region comprising an amino acid sequence having at least 85% identical to the amino acid sequences of SEQ ID NO: 147, and (ii) a light chain variable region comprising an amino acid sequence having at least 80% identical to the amino acid sequence of SEQ ID NO: 195. In a further embodiment, the present invention provides an isolated anti-Globo H antibody, comprising (i) a heavy chain variable region comprising an amino acid sequence consisting of SEQ ID NO: 147, and (ii) a light chain variable region comprising an amino acid sequence consisting of SEQ ID NO: 195 (MZ-2 antibody). The nucleotides encoding the heavy chain variable region having the amino acid sequence of SEQ ID NO: 147 are as follows:

```
                                         (SEQ ID NO: 236)
CAGGTTACTCTGAAAGAGTCTGGCCCTGGGATATTGCAGACCTCCCAGAC

CCTCAGTCTGACTTGTTCTTTCTCTGGGTTTTCACTGGGCACTTTTGATT

TGGGTATAGGCTGGATTCGTCAGCCTTCAGGGAAGGGTCTGGAGTGGCTG

GCGCACATCTGGTGGGATGATGATAAGTACTATAATCCAGCCCTGAAGAG

TCGGCTCACAATCTCCAAGGATACCTCCAAAAACCAGGTATTCCTCAAGA

TCGCCAATGTGGACACTGCAGACTCTGCCACATATTACTGTGCTCGGCTC

TCTGGAAACTACCTCACGTCGTTCTACTGTGACTACTGGGGCCAAGGCAC

CACTCTCACAGTGTCCTCA
```

The nucleotides encoding the light chain variable region having the amino acid sequence of SEQ ID NO: 195 are as follows:

```
                                         (SEQ ID NO: 237)
CAAATTGTTCTCACCCAGTCTCCAGCAATCGTGTCTGCATCTCCAGGGG

AGAAGGTCACCATGACCTGCAGTGCCAGATCAAGTGTAAGTTATATGCA

CTGGTACCAGCAGAAGTCAGGCACCTCCCCCAAAAGATGGATTTATGAC

ACATCCAAACTGGCTTCTGGAGTCCCTGCTCGCTTCAGTGGCAGTGGGT

CTGGGACCTCTTATTCTCTCACAATCAGCAGCATGGAGGCTGAAGACGC

TGCCACTTATTACTGCCAGCAGTGGAGTAGTAATCCACTCACGTTCGGT

GCTGGGACCAAGCTGGAACTGAAACGG
```

Heavy Chain Variable Region of MZ-2 Series

```
                                         (SEQ ID NO: 140)
QVTLKESGPGILQTSQTLSLTCSFSGFSLSTFDMGVGWIRQPSGKGLEWL
AHIWWDDDKYYNPALKSRLTISKDTSKNQVFLKIANVDTADSATYYCARL
YGNYLTSFYCDYWGQGTTLTVSS (SEQ ID NO: 141)
QVTLKESGPGILQTSQTLSLTCSFSGFSLSTFDMGVGWIRQPSGKGLEWL
AHIWWDDDKYYNPALKSRLTISKDTSKNQVFLKIANVDTADSATYYCARL
SGNYLTSFYCDYWGQGTTLTVSS (SEQ ID NO: 142)
QVTLKESGPGILQTSQTLSLTCSFSGFSLSTFDMGVGWIRQPSGKGLEWL
AHIWWDDDKYYNPALKSRLTISKDTSKNQVFLKIANVDTADSATYYCARL
YGNYLRSYYCDYWGQGTTLTVSS (SEQ ID NO: 143)
QVTLKESGPGILQTSQTLSLTCSFSGSSLSTFDVGVGWIRQPSGKGLEWL
AHIWWDDDKYYNPALKSRLTISKDTSKNQVFLKIANVDTADSATYYCARL
YGNYLTSFYCDYWGQGTTLTVSS (SEQ ID NO: 144)
QVTLKESGPGILQTSQTLSLTCSFSGSSLSTFDVGVGWIRQPSGKGLEWL
AHIWWDDDKYYNPALKSRLTISKDTSKNQVFLKIANVDTADSATYYCARL
SGNYLTSFYCDYWGQGTTLTVSS (SEQ ID NO: 145)
QVTLKESGPGILQTSQTLSLTCSFSGSSLSTFDVGVGWIRQPSGKGLEWL
AHIWWDDDKYYNPALKSRLTISKDTSKNQVFLKIANVDTADSATYYCARL
YGNYLTSFYCDYWGQGTTLTVSS (SEQ ID NO: 146)
QVTLKESGPGILQTSQTLSLTCSFSGFSLGTFDLGIGWIRQPSGKGLEWL
AHIWWDDDKYYNPALKSRLTISKDTSKNQVFLKIANVDTADSATYYCARL
YGNYLTSFYCDYWGQGTTLTVSS (SEQ ID NO: 147)
QVTLKESGPGILQTSQTLSLTCSFSGFSLGTFDLGIGWIRQPSGKGLEWL
AHIWWDDDKYYNPALKSRLTISKDTSKNQVFLKIANVDTADSATYYCARL
SGNYLTSFYCDYWGQGTTLTVSS (SEQ ID NO: 148)
QVTLKESGPGILQTSQTLSLTCSFSGFSLGTFDLGIGWIRQPSGKGLEWL
AHIWWDDDKYYNPALKSRLTISKDTSKNQVFLKIANVDTADSATYYCARL
YGNYLRSYYCDYWGQGTTLTVSS (SEQ ID NO: 149)
QVTLKESGPGILQTSQTLSLTCSFSGFSLSTFDLGIGWIRQPSGKGLEWL
AHIWWDDDKYYNPALKSRLTISKDTSKNQVFLKIANVDTADSATYYCARL
YGNYLTSFYCDYWGQGTTLTVSS (SEQ ID NO: 150)
QVTLKESGPGILQTSQTLSLTCSFSGFSLSTFDLGIGWIRQPSGKGLEWL
AHIWWDDDKYYNPALKSRLTISKDTSKNQVFLKIANVDTADSATYYCARL
SGNYLTSFYCDYWGQGTTLTVSS (SEQ ID NO: 151)
QVTLKESGPGILQTSQTLSLTCSFSGFSLSTFDLGIGWIRQPSGKGLEWL
AHIWWDDDKYYNPALKSRLTISKDTSKNQVFLKIANVDTADSATYYCARL
YGNYLRSYYCDYWGQGTTLTVSS (SEQ ID NO: 152)
QVTLKESGPGILQTSQTLSLTCSFSGFSLSTFDMGVGWIRQPSGKGLEWL
AHIWGDDDKYYNPALKSRLTISKDTSKNQVFLKIANVDTADSATYYCARL
YGNYLTSFYCDYWGQGTTLTVSS (SEQ ID NO: 153)
QVTLKESGPGILQTSQTLSLTCSFSGFSLSTFDMGVGWIRQPSGKGLEWL
AHIWGDDDKYYNPALKSRLTISKDTSKNQVFLKIANVDTADSATYYCARL
SGNYLTSFYCDYWGQGTTLTVSS (SEQ ID NO: 154)
QVTLKESGPGILQTSQTLSLTCSFSGFSLSTFDMGVGWIRQPSGKGLEWL
AHIWGDDDKYYNPALKSRLTISKDTSKNQVFLKIANVDTADSATYYCARL
YGNYLRSYYCDYWGQGTTLTVSS (SEQ ID NO: 155)
QVTLKESGPGILQTSQTLSLTCSFSGSSLSTFDVGVGWIRQPSGKGLEWL
AHIWGDDDKYYNPALKSRLTISKDTSKNQVFLKIANVDTADSATYYCARL
YGNYLTSFYCDYWGQGTTLTVSS (SEQ ID NO: 156)
QVTLKESGPGILQTSQTLSLTCSFSGSSLSTFDVGVGWIRQPSGKGLEWL
AHIWGDDDKYYNPALKSRLTISKDTSKNQVFLKIANVDTADSATYYCARL
SGNYLTSFYCDYWGQGTTLTVSS (SEQ ID NO: 157)
QVTLKESGPGILQTSQTLSLTCSFSGSSLSTFDVGVGWIRQPSGKGLEWL
AHIWGDDDKYYNPALKSRLTISKDTSKNQVFLKIANVDTADSATYYCARL
YGNYLRSYYCDYWGQGTTLTVSS (SEQ ID NO: 158)
QVTLKESGPGILQTSQTLSLTCSFSGFSLGTFDLGIGWIRQPSGKGLEWL
AHIWGDDDKYYNPALKSRLTISKDTSKNQVFLKIANVDTADSATYYCARL
YGNYLTSFYCDYWGQGTTLTVSS
```

(SEQ ID NO: 159)
QVTLKESGPGILQTSQTLSLTCSFSGFSLGTFDLGIGWIRQPSGKGLEWL
AHIWGDDDKYYNPALKSRLTISKDTSKNQVFLKIANVDTADSATYYCARL
SGNYLTSFYCDYWGQGTTLTVSS (SEQ ID NO: 160)
QVTLKESGPGILQTSQTLSLTCSFSGFSLGTFDLGIGWIRQPSGKGLEWL
AHIWGDDDKYYNPALKSRLTISKDTSKNQVFLKIANVDTADSATYYCARL
YGNYLRSYYCDYWGQGTTLTVSS (SEQ ID NO: 161)
QVTLKESGPGILQTSQTLSLTCSFSGFSLSTFDLGIGWIRQPSGKGLEWL
AHIWGDDDKYYNPALKSRLTISKDTSKNQVFLKIANVDTADSATYYCARL
YGNYLTSFYCDYWGQGTTLTVSS (SEQ ID NO: 162)
QVTLKESGPGILQTSQTLSLTCSFSGFSLSTFDLGIGWIRQPSGKGLEWL
AHIWGDDDKYYNPALKSRLTISKDTSKNQVFLKIANVDTADSATYYCARL
SGNYLTSFYCDYWGQGTTLTVSS (SEQ ID NO: 163)
QVTLKESGPGILQTSQTLSLTCSFSGFSLSTFDLGIGWIRQPSGKGLEWL
AHIWGDDDKYYNPALKSRLTISKDTSKNQVFLKIANVDTADSATYYCARL
YGNYLRSYYCDYWGQGTTLTVSS

Light Chain Variable Region of MZ-2 Series (SEQ ID NO: 164)
QIVLTQSPAIVSASPGEKVTMTCSASSSVSYMHWYQQKSGTSPKRWIYAT
SNLASGVPARFSGSGSGTSYSLTISSMEAEDAATYYCQQWSSNPFTFGAG
TKLELKR (SEQ ID NO: 165)
QIVLTQSPAIVSASPGEKVTMTCSASSSVSYMHWYQQKSGTSPKRWIYAT
SNLASGVPARFSGSGSGTSYSLTISSMEAEDAATYYCQQWSSNPLTFGAG
TKLELKR (SEQ ID NO: 166)
QIVLTQSPAIVSASPGEKVTMTCSASSSVSYMHWYQQKSGTSPKRWIYAT
SNLASGVPARFSGSGSGTSYSLTISSMEAEDAATYYCQQHLHIPYTFGAG
TKLELKR (SEQ ID NO: 167)
QIVLTQSPAIVSASPGEKVTMTCSASSRVSYMHWYQQKSGTSPKRWIYAT
SNLASGVPARFSGSGSGTSYSLTISSMEAEDAATYYCQQWSSNPFTFGAG
TKLELKR (SEQ ID NO: 168)
QIVLTQSPAIVSASPGEKVTMTCSASSRVSYMHWYQQKSGTSPKRWIYAT
SNLASGVPARFSGSGSGTSYSLTISSMEAEDAATYYCQQWSSNPLTFGAG
TKLELKR (SEQ ID NO: 169)
QIVLTQSPAIVSASPGEKVTMTCSASSRVSYMHWYQQKSGTSPKRWIYAT
SNLASGVPARFSGSGSGTSYSLTISSMEAEDAATYYCQQHLHIPYTFGAG
TKLELKR (SEQ ID NO: 170)
QIVLTQSPAIVSASPGEKVTMTCSARSSVSYMHWYQQKSGTSPKRWIYAT
SNLASGVPARFSGSGSGTSYSLTISSMEAEDAATYYCQQWSSNPFTFGAG
TKLELKR (SEQ ID NO: 171)
QIVLTQSPAIVSASPGEKVTMTCSARSSVSYMHWYQQKSGTSPKRWIYAT
SNLASGVPARFSGSGSGTSYSLTISSMEAEDAATYYCQQWSSNPLTFGAG
TKLELKR (SEQ ID NO: 172)
QIVLTQSPAIVSASPGEKVTMTCSARSSVSYMHWYQQKSGTSPKRWIYAT
SNLASGVPARFSGSGSGTSYSLTISSMEAEDAATYYCQQHLHIPYTFGAG
TKLELKR (SEQ ID NO: 173)
QIVLTQSPAIVSASPGEKVTMTCRASSSVSYMHWYQQKSGTSPKRWIYAT
SNLASGVPARFSGSGSGTSYSLTISSMEAEDAATYYCQQWSSNPFTFGAG
TKLELKR (SEQ ID NO: 174)
QIVLTQSPAIVSASPGEKVTMTCRASSSVSYMHWYQQKSGTSPKRWIYAT
SNLASGVPARFSGSGSGTSYSLTISSMEAEDAATYYCQQWSSNPLTFGAG
TKLELKR (SEQ ID NO: 175)
QIVLTQSPAIVSASPGEKVTMTCRASSSVSYMHWYQQKSGTSPKRWIYAT
SNLASGVPARFSGSGSGTSYSLTISSMEAEDAATYYCQQHLHIPYTFGAG
TKLELKR (SEQ ID NO: 176)
QIVLTQSPAIVSASPGEKVTMTCSASSSVSYMHWYQQKSGTSPKRWIYWT
SDRYSGVPARFSGSGSGTSYSLTISSMEAEDAATYYCQQWSSNPFTFGAG
TKLELKR (SEQ ID NO: 177)
QIVLTQSPAIVSASPGEKVTMTCSASSSVSYMHWYQQKSGTSPKRWIYWT
SDRYSGVPARFSGSGSGTSYSLTISSMEAEDAATYYCQQWSSNPLTFGAG
TKLELKR (SEQ ID NO: 178)
QIVLTQSPAIVSASPGEKVTMTCSASSSVSYMHWYQQKSGTSPKRWIYWT
SDRYSGVPARFSGSGSGTSYSLTISSMEAEDAATYYCQQHLHIPYTFGAG
TKLELKR (SEQ ID NO: 179)
QIVLTQSPAIVSASPGEKVTMTCSASSRVSYMHWYQQKSGTSPKRWIYWT
SDRYSGVPARFSGSGSGTSYSLTISSMEAEDAATYYCQQWSSNPFTFGAG
TKLELKR (SEQ ID NO: 180)
QIVLTQSPAIVSASPGEKVTMTCSASSRVSYMHWYQQKSGTSPKRWIY
WTSDRYSGVPARFSGSGSGTSYSLTISSMEAEDAATYYCQQWSSNPLTF
GAGTKLELKR (SEQ ID NO: 181)
QIVLTQSPAIVSASPGEKVTMTCSASSRVSYMHWYQQKSGTSPKRWIYW
TSDRYSGVPARFSGSGSGTSYSLTISSMEAEDAATYYCQQHLHIPYTFG
AGTKLELKR (SEQ ID NO: 182)
QIVLTQSPAIVSASPGEKVTMTCSARSSVSYMHWYQQKSGTSPKRWIYWT
SDRYSGVPARFSGSGSGTSYSLTISSMEAEDAATYYCQQWSSNPFTFGAG
TKLELKR (SEQ ID NO: 183)
QIVLTQSPAIVSASPGEKVTMTCSARSSVSYMHWYQQKSGTSPKRWIYWT
SDRYSGVPARFSGSGSGTSYSLTISSMEAEDAATYYCQQWSSNPLTFGAG
TKLELKR (SEQ ID NO: 184)
QIVLTQSPAIVSASPGEKVTMTCSARSSVSYMHWYQQKSGTSPKRWIYWT
SDRYSGVPARFSGSGSGTSYSLTISSMEAEDAATYYCQQHLHIPYTFGAG
TKLELKR (SEQ ID NO: 185)
QIVLTQSPAIVSASPGEKVTMTCRASSSVSYMHWYQQKSGTSPKRWIYWT
SDRYSGVPARFSGSGSGTSYSLTISSMEAEDAATYYCQQWSSNPFTFGAG
TKLELKR (SEQ ID NO: 186)
QIVLTQSPAIVSASPGEKVTMTCRASSSVSYMHWYQQKSGTSPKRWIYWT
SDRYSGVPARFSGSGSGTSYSLTISSMEAEDAATYYCQQWSSNPLTFGAG
TKLELKR (SEQ ID NO: 187)
QIVLTQSPAIVSASPGEKVTMTCRASSSVSYMHWYQQKSGTSPKRWIYWT
SDRYSGVPARFSGSGSGTSYSLTISSMEAEDAATYYCQQHLHIPYTFGAG
TKLELKR (SEQ ID NO: 188)
QIVLTQSPAIVSASPGEKVTMTCSASSSVSYMHWYQQKSGTSPKRWIYDT
SKLASGVPARFSGSGSGTSYSLTISSMEAEDAATYYCQQWSSNPFTFGAG
TKLELKR (SEQ ID NO: 189)
QIVLTQSPAIVSASPGEKVTMTCSASSSVSYMHWYQQKSGTSPKRWIYDT
SKLASGVPARFSGSGSGTSYSLTISSMEAEDAATYYCQQWSSNPLTFGAG
TKLELKR -continued

```
                                         (SEQ ID NO: 190)
QIVLTQSPAIVSASPGEKVTMTCSASSSVSYMHWYQQKSGTSPKRWIYDT
SKLASGVPARFSGSGSGTSYSLTISSMEAEDAATYYCQQHLHIPYTFGAG
TKLELKR (SEQ ID NO: 191)
QIVLTQSPAIVSASPGEKVTMTCSASSRVSYMHWYQQKSGTSPKRWIYDT
SKLASGVPARFSGSGSGTSYSLTISSMEAEDAATYYCQQWSSNPFTFGAG
TKLELKR (SEQ ID NO: 192)
QIVLTQSPAIVSASPGEKVTMTCSASSRVSYMHWYQQKSGTSPKRWIYDT
SKLASGVPARFSGSGSGTSYSLTISSMEAEDAATYYCQQWSSNPLTFGAG
TKLELKR (SEQ ID NO: 193)
QIVLTQSPAIVSASPGEKVTMTCSASSRVSYMHWYQQKSGTSPKRWIYDT
SKLASGVPARFSGSGSGTSYSLTISSMEAEDAATYYCQQHLHIPYTFGAG
TKLELKR (SEQ ID NO: 194)
QIVLTQSPAIVSASPGEKVTMTCSARSSVSYMHWYQQKSGTSPKRWIYDT
SKLASGVPARFSGSGSGTSYSLTISSMEAEDAATYYCQQWSSNPFTFGAG
TKLELKR (SEQ ID NO: 195)
QIVLTQSPAIVSASPGEKVTMTCSARSSVSYMHWYQQKSGTSPKRWIYDT
SKLASGVPARFSGSGSGTSYSLTISSMEAEDAATYYCQQWSSNPLTFGAG
TKLELKR (SEQ ID NO: 196)
QIVLTQSPAIVSASPGEKVTMTCSARSSVSYMHWYQQKSGTSPKRWIYDT
SKLASGVPARFSGSGSGTSYSLTISSMEAEDAATYYCQQHLHIPYTFGAG
TKLELKR (SEQ ID NO: 197)
QIVLTQSPAIVSASPGEKVTMTCRASSSVSYMHWYQQKSGTSPKRWIYDT
SKLASGVPARFSGSGSGTSYSLTISSMEAEDAATYYCQQWSSNPFTFGAG
TKLELKR (SEQ ID NO: 198)
QIVLTQSPAIVSASPGEKVTMTCSARSSVSYMHWYQQKSGTSPKRWIYDT
SKLASGVPARFSGSGSGTSYSLTISSMEAEDAATYYCQQWSSNPLTFGAG
TKLELKR (SEQ ID NO: 199)
QIVLTQSPAIVSASPGEKVTMTCSARSSVSYMHWYQQKSGTSPKRWIYDT
SKLASGVPARFSGSGSGTSYSLTISSMEAEDAATYYCQQHLHIPYTFGAG
TKLELKR
```

In another embodiment, the isolated anti-Globo H antibody of the present invention is a humanized or chimeric antibody or fragment thereof capable of specifically binding to Globo H.

In a further embodiment, the present invention provides a humanized anti-Globo H antibody or an antigen-binding portion thereof, comprising (i) a heavy chain variable region comprising an amino acid sequence having at least 85% identical to any of the amino acid sequences of SEQ ID NOs: 20 to 43, and (ii) a light chain variable region comprising an amino acid sequence having at least 80% identical to any of the amino acid sequence of SEQ ID NO: 44 to 79 and 200 to 235. Preferably, the sequence identity as mentioned above is at least 90%, 91%, 91%, 92%, 93%, 94%, 95%, 96%, 97%, 98% or 99%.

In another further embodiment, the present invention provides a humanized anti-Globo H antibody or an antigen-binding portion thereof, comprising (i) a heavy chain variable region comprising an amino acid sequence selected from the group consisting of SEQ ID NOs: 20 to 43, and (ii) a light chain variable region comprising an amino acid sequence selected from the group consisting of SEQ ID NO: 44 to 79 and 200 to 235. In another embodiment, the humanized anti-Globo H antibody or an antigen-binding portion thereof comprises a heavy chain variable region comprising an amino acid sequence consisting of SEQ ID NO: 27, and a light chain variable region comprising an amino acid sequence consisting of SEQ ID NO: 75 (hMZ-2Lw antibody). In another embodiment, the humanized anti-Globo H antibody or an antigen-binding portion thereof comprises a heavy chain variable region comprising an amino acid sequence consisting of SEQ ID NO: 27, and a light chain variable region comprising an amino acid sequence consisting of SEQ ID NO: 231.

Heavy Chain Variable Region of hMZ-2 Series

```
(QITLKESGPTLVKPTQTLTLTCTFS************WIRQPPGKALEW
LA************LKSRLTITKDTSKNQVVLTMTNMDPVDTATYYCAR
*************WGQGTLVTVSS)

(SEQ ID NO: 20)
QITLKESGPTLVKPTQTLTLTCTFSGFSLSTFDMGVGWIRQPPGKALEWL
AHIWWDDDKYYNPALKSRLTITKDTSKNQVVLTMTNMDPVDTATYYCARL
YGNYLTSFYCDYWGQGTLVTVSS (SEQ ID NO: 21)
QITLKESGPTLVKPTQTLTLTCTFSGFSLSTFDMGVGWIRQPPGKALEWL
AHIWWDDDKYYNPALKSRLTITKDTSKNQVVLTMTNMDPVDTATYYCARL
SGNYLTSFYCDYWGQGTLVTVSS (SEQ ID NO: 22)
QITLKESGPTLVKPTQTLTLTCTFSGFSLSTFDMGVGWIRQPPGKALEWL
AHIWWDDDKYYNPALKSRLTITKDTSKNQVVLTMTNMDPVDTATYYCARL
YGNYLRSYYCDYWGQGTLVTVSS (SEQ ID NO: 23)
QITLKESGPTLVKPTQTLTLTCTFSGSSLSTFDVGVGWIRQPPGKALEWL
AHIWWDDDKYYNPALKSRLTITKDTSKNQVVLTMTNMDPVDTATYYCARL
YGNYLTSFYCDYWGQGTLVTVSS (SEQ ID NO: 24)
QITLKESGPTLVKPTQTLTLTCTFSGSSLSTFDVGVGWIRQPPGKALEWL
AHIWWDDDKYYNPALKSRLTITKDTSKNQVVLTMTNMDPVDTATYYCARL
SGNYLTSFYCDYWGQGTLVTVSS (SEQ ID NO: 25)
QITLKESGPTLVKPTQTLTLTCTFSGSSLSTFDVGVGWIRQPPGKALEWL
AHIWWDDDKYYNPALKSRLTITKDTSKNQVVLTMTNMDPVDTATYYCARL
SGNYLTSFYCDYWGQGTLVTVSS (SEQ ID NO: 26)
QITLKESGPTLVKPTQTLTLTCTFSGFSLGTFDLGIGWIRQPPGKALEWL
AHIWWDDDKYYNPALKSRLTITKDTSKNQVVLTMTNMDPVDTATYYCARL
YGNYLTSFYCDYWGQGTLVTVSS (SEQ ID NO: 27)
QITLKESGPTLVKPTQTLTLTCTFSGFSLGTFDLGIGWIRQPPGKALEWL
AHIWWDDDKYYNPALKSRLTITKDTSKNQVVLTMTNMDPVDTATYYCARL
SGNYLTSFYCDYWGQGTLVTVSS (SEQ ID NO: 28)
QITLKESGPTLVKPTQTLTLTCTFSGFSLGTFDLGIGWIRQPPGKALEWL
AHIWWDDDKYYNPALKSRLTITKDTSKNQVVLTMTNMDPVDTATYYCARL
YGNYLRSYYCDYWGQGTLVTVSS (SEQ ID NO: 29)
QITLKESGPTLVKPTQTLTLTCTFSGFSLSTFDLGIGWIRQPPGKALEWL
AHIWWDDDKYYNPALKSRLTITKDTSKNQVVLTMTNMDPVDTATYYCARL
YGNYLTSFYCDYWGQGTLVTVSS (SEQ ID NO: 30)
QITLKESGPTLVKPTQTLTLTCTFSGFSLSTFDLGIGWIRQPPGKALEWL
AHIWWDDDKYYNPALKSRLTITKDTSKNQVVLTMTNMDPVDTATYYCARL
SGNYLTSFYCDYWGQGTLVTVSS (SEQ ID NO: 31)
QITLKESGPTLVKPTQTLTLTCTFSGFSLSTFDLGIGWIRQPPGKALEWL
AHIWWDDDKYYNPALKSRLTITKDTSKNQVVLTMTNMDPVDTATYYCARL
YGNYLRSYYCDYWGQGTLVTVSS
```

```
                                                (SEQ ID NO: 32)
QITLKESGPTLVKPTQTLTLTCTFSGFSLSTFDMGVGWIRQPPGKALEWL
AHIWGDDDKYYNPALKSRLTITKDTSKNQVVLTMTNMDPVDTATYYCARL
YGNYLTSFYCDYWGQGTLVTVSS (SEQ ID NO: 33)
QITLKESGPTLVKPTQTLTLTCTFSGFSLSTFDMGVGWIRQPPGKALEWL
AHIWGDDDKYYNPALKSRLTITKDTSKNQVVLTMTNMDPVDTATYYCARL
SGNYLTSFYCDYWGQGTLVTVSS (SEQ ID NO: 34)
QITLKESGPTLVKPTQTLTLTCTFSGFSLSTFDMGVGWIRQPPGKALEWL
AHIWGDDDKYYNPALKSRLTITKDTSKNQVVLTMTNMDPVDTATYYCARL
YGNYLRSYYCDYWGQGTLVTVSS (SEQ ID NO: 35)
QITLKESGPTLVKPTQTLTLTCTFSGSSLSTFDVGVGWIRQPPGKALEWL
AHIWGDDDKYYNPALKSRLTITKDTSKNQVVLTMTNMDPVDTATYYCARL
YGNYLTSFYCDYWGQGTLVTVSS (SEQ ID NO: 36)
QITLKESGPTLVKPTQTLTLTCTFSGSSLSTFDVGVGWIRQPPGKALEWL
AHIWGDDDKYYNPALKSRLTITKDTSKNQVVLTMTNMDPVDTATYYCARL
SGNYLTSFYCDYWGQGTLVTVSS (SEQ ID NO: 37)
QITLKESGPTLVKPTQTLTLTCTFSGSSLSTFDVGVGWIRQPPGKALEWL
AHIWGDDDKYYNPALKSRLTITKDTSKNQVVLTMTNMDPVDTATYYCARL
YGNYLRSYYCDYWGQGTLVTVSS (SEQ ID NO: 38)
QITLKESGPTLVKPTQTLTLTCTFSGFSLGTFDLGIGWIRQPPGKALEWL
AHIWGDDDKYYNPALKSRLTITKDTSKNQVVLTMTNMDPVDTATYYCARL
YGNYLTSFYCDYWGQGTLVTVSS (SEQ ID NO: 39)
QITLKESGPTLVKPTQTLTLTCTFSGFSLGTFDLGIGWIRQPPGKALEWL
AHIWGDDDKYYNPALKSRLTITKDTSKNQVVLTMTNMDPVDTATYYCARL
SGNYLTSFYCDYWGQGTLVTVSS (SEQ ID NO: 40)
QITLKESGPTLVKPTQTLTLTCTFSGFSLGTFDLGIGWIRQPPGKALEWL
AHIWGDDDKYYNPALKSRLTITKDTSKNQVVLTMTNMDPVDTATYYCARL
YGNYLRSYYCDYWGQGTLVTVSS (SEQ ID NO: 41)
QITLKESGPTLVKPTQTLTLTCTFSGFSLSTFDLGIGWIRQPPGKALEWL
AHIWGDDDKYYNPALKSRLTITKDTSKNQVVLTMTNMDPVDTATYYCARL
YGNYLTSFYCDYWGQGTLVTVSS (SEQ ID NO: 42)
QITLKESGPTLVKPTQTLTLTCTFSGFSLSTFDLGIGWIRQPPGKALEWL
AHIWGDDDKYYNPALKSRLTITKDTSKNQVVLTMTNMDPVDTATYYCARL
SGNYLTSFYCDYWGQGTLVTVSS (SEQ ID NO: 43)
QITLKESGPTLVKPTQTLTLTCTFSGFSLSTFDLGIGWIRQPPGKALEWL
AHIWGDDDKYYNPALKSRLTITKDTSKNQVVLTMTNMDPVDTATYYCARL
YGNYLRSYYCDYWGQGTLVTVSS
```

Light Chain Variable Region of hMZ-2 Series

```
(EIVLTQSPSSLSASVGDRVTITC*********WYQQKPGKAPKLLIY
*******GVPSRFSGSGSGTDFTFTISSLQPEDIATYYC*********F
GGGTKLEIKR)

(SEQ ID NO: 44)
EIVLTQSPSSLSASVGDRVTITCSASSSVSYMHWYQQKPGKAPKLLIY
ATSNLASGVPSRFSGSGSGTDFTFTISSLQPEDIATYYCQQWSSNPFT
FGGGTKLEIKR (SEQ ID NO: 45)
EIVLTQSPSSLSASVGDRVTITCSASSSVSYMHWYQQKPGKAPKLLIY
ATSNLASGVPSRFSGSGSGTDFTFTISSLQPEDIATYYCQQWSSNPLT
FGGGTKLEIKR (SEQ ID NO: 46)
EIVLTQSPSSLSASVGDRVTITCSASSSVSYMHWYQQKPGKAPKLLIY
ATSNLASGVPSRFSGSGSGTDFTFTISSLQPEDIATYYCQQHLHIPYT
FGGGTKLEIKR (SEQ ID NO: 47)
EIVLTQSPSSLSASVGDRVTITCSASSRVSYMHWYQQKPGKAPKLLIY
ATSNLASGVPSRFSGSGSGTDFTFTISSLQPEDIATYYCQQWSSNPFT
FGGGTKLEIKR (SEQ ID NO: 48)
EIVLTQSPSSLSASVGDRVTITCSASSRVSYMHWYQQKPGKAPKLLIY
ATSNLASGVPSRFSGSGSGTDFTFTISSLQPEDIATYYCQQWSSNPLT
FGGGTKLEIKR (SEQ ID NO: 49)
EIVLTQSPSSLSASVGDRVTITCSASSRVSYMHWYQQKPGKAPKLLIY
ATSNLASGVPSRFSGSGSGTDFTFTISSLQPEDIATYYCQQHLHIPYT
FGGGTKLEIKR (SEQ ID NO: 50)
EIVLTQSPSSLSASVGDRVTITCSARSSVSYMHWYQQKPGKAPKLLIY
ATSNLASGVPSRFSGSGSGTDFTFTISSLQPEDIATYYCQQWSSNPFT
FGGGTKLEIKR (SEQ ID NO: 51)
EIVLTQSPSSLSASVGDRVTITCSARSSVSYMHWYQQKPGKAPKLLIY
ATSNLASGVPSRFSGSGSGTDFTFTISSLQPEDIATYYCQQWSSNPLT
FGGGTKLEIKR (SEQ ID NO: 52)
EIVLTQSPSSLSASVGDRVTITCSARSSVSYMHWYQQKPGKAPKLLIY
ATSNLASGVPSRFSGSGSGTDFTFTISSLQPEDIATYYCQQHLHIPYT
FGGGTKLEIKR (SEQ ID NO: 53)
EIVLTQSPSSLSASVGDRVTITCRASSSVSYMHWYQQKPGKAPKLLIY
ATSNLASGVPSRFSGSGSGTDFTFTISSLQPEDIATYYCQQWSSNPFT
FGGGTKLEIKR (SEQ ID NO: 54)
EIVLTQSPSSLSASVGDRVTITCRASSSVSYMHWYQQKPGKAPKLLIY
ATSNLASGVPSRFSGSGSGTDFTFTISSLQPEDIATYYCQQWSSNPLT
FGGGTKLEIKR (SEQ ID NO: 55)
EIVLTQSPSSLSASVGDRVTITCRASSSVSYMHWYQQKPGKAPKLLIY
ATSNLASGVPSRFSGSGSGTDFTFTISSLQPEDIATYYCQQHLHIPYT
FGGGTKLEIKR (SEQ ID NO: 56)
EIVLTQSPSSLSASVGDRVTITCSASSSVSYMHWYQQKPGKAPKLLIY
WTSDRYSGVPSRFSGSGSGTDFTFTISSLQPEDIATYYCQQWSSNPFT
FGGGTKLEIKR (SEQ ID NO: 57)
EIVLTQSPSSLSASVGDRVTITCSASSSVSYMHWYQQKPGKAPKLLIY
WTSDRYSGVPSRFSGSGSGTDFTFTISSLQPEDIATYYCQQWSSNPLT
FGGGTKLEIKR (SEQ ID NO: 58)
EIVLTQSPSSLSASVGDRVTITCSASSSVSYMHWYQQKPGKAPKLLIY
WTSDRYSGVPSRFSGSGSGTDFTFTISSLQPEDIATYYCQQHLHIPYT
FGGGTKLEIKR (SEQ ID NO: 59)
EIVLTQSPSSLSASVGDRVTITCSASSRVSYMHWYQQKPGKAPKLLIY
WTSDRYSGVPSRFSGSGSGTDFTFTISSLQPEDIATYYCQQWSSNPFT
FGGGTKLEIKR (SEQ ID NO: 60)
EIVLTQSPSSLSASVGDRVTITCSASSRVSYMHWYQQKPGKAPKLLIY
WTSDRYSGVPSRFSGSGSGTDFTFTISSLQPEDIATYYCQQWSSNPLT
FGGGTKLEIKR (SEQ ID NO: 61)
EIVLTQSPSSLSASVGDRVTITCSASSRVSYMHWYQQKPGKAPKLLIY
WTSDRYSGVPSRFSGSGSGTDFTFTISSLQPEDIATYYCQQHLHIPYT
FGGGTKLEIKR
```

(SEQ ID NO: 62)
EIVLTQSPSSLSASVGDRVTITCSARSSVSYMHWYQQKPGKAPKLLIY
WTSDRYSGVPSRFSGSGSGTDFTFTISSLQPEDIATYYCQQWSSNPFT
FGGGTKLEIKR (SEQ ID NO: 63)
EIVLTQSPSSLSASVGDRVTITCSARSSVSYMHWYQQKPGKAPKLLIY
WTSDRYSGVPSRFSGSGSGTDFTFTISSLQPEDIATYYCQQWSSNPLT
FGGGTKLEIKR (SEQ ID NO: 64)
EIVLTQSPSSLSASVGDRVTITCSARSSVSYMHWYQQKPGKAPKLLIY
WTSDRYSGVPSRFSGSGSGTDFTFTISSLQPEDIATYYCQQHLHIPYT
FGGGTKLEIKR (SEQ ID NO: 65)
EIVLTQSPSSLSASVGDRVTITCRASSSVSYMHWYQQKPGKAPKLLIY
WTSDRYSGVPSRFSGSGSGTDFTFTISSLQPEDIATYYCQQWSSNPFT
FGGGTKLEIKR (SEQ ID NO: 66)
EIVLTQSPSSLSASVGDRVTITCRASSSVSYMHWYQQKPGKAPKLLIY
WTSDRYSGVPSRFSGSGSGTDFTFTISSLQPEDIATYYCQQWSSNPLT
FGGGTKLEIKR (SEQ ID NO: 67)
EIVLTQSPSSLSASVGDRVTITCRASSSVSYMHWYQQKPGKAPKLLIY
WTSDRYSGVPSRFSGSGSGTDFTFTISSLQPEDIATYYCQQHLHIPYT
FGGGTKLEIKR (SEQ ID NO: 68)
EIVLTQSPSSLSASVGDRVTITCSASSSVSYMHWYQQKPGKAPKLLIY
DTSKLASGVPSRFSGSGSGTDFTFTISSLQPEDIATYYCQQWSSNPFT
FGGGTKLEIKR (SEQ ID NO: 69)
EIVLTQSPSSLSASVGDRVTITCSASSSVSYMHWYQQKPGKAPKLLIY
DTSKLASGVPSRFSGSGSGTDFTFTISSLQPEDIATYYCQQWSSNPLT
FGGGTKLEIKR (SEQ ID NO: 70)
EIVLTQSPSSLSASVGDRVTITCSASSSVSYMHWYQQKPGKAPKLLIY
DTSKLASGVPSRFSGSGSGTDFTFTISSLQPEDIATYYCQQHLHIPYT
FGGGTKLEIKR (SEQ ID NO: 71)
EIVLTQSPSSLSASVGDRVTITCSASSRVSYMHWYQQKPGKAPKLLIY
DTSKLASGVPSRFSGSGSGTDFTFTISSLQPEDIATYYCQQWSSNPLT
FGGGTKLEIKR (SEQ ID NO: 72)
EIVLTQSPSSLSASVGDRVTITCSASSRVSYMHWYQQKPGKAPKLLIY
DTSKLASGVPSRFSGSGSGTDFTFTISSLQPEDIATYYCQQWSSNPLT
FGGGTKLEIKR (SEQ ID NO: 73)
EIVLTQSPSSLSASVGDRVTITCSASSRVSYMHWYQQKPGKAPKLLIY
DTSKLASGVPSRFSGSGSGTDFTFTISSLQPEDIATYYCQQHLHIPYT
FGGGTKLEIKR (SEQ ID NO: 74)
EIVLTQSPSSLSASVGDRVTITCSARSSVSYMHWYQQKPGKAPKLLIY
DTSKLASGVPSRFSGSGSGTDFTFTISSLQPEDIATYYCQQWSSNPFT
FGGGTKLEIKR (SEQ ID NO: 75)
EIVLTQSPSSLSASVGDRVTITCSARSSVSYMHWYQQKPGKAPKLLIY
DTSKLASGVPSRFSGSGSGTDFTFTISSLQPEDIATYYCQQWSSNPLT
FGGGTKLEIKR (SEQ ID NO: 76)
EIVLTQSPSSLSASVGDRVTITCSARSSVSYMHWYQQKPGKAPKLLIY
DTSKLASGVPSRFSGSGSGTDFTFTISSLQPEDIATYYCQQHLHIPYT
FGGGTKLEIKR (SEQ ID NO: 77)
EIVLTQSPSSLSASVGDRVTITCRASSSVSYMHWYQQKPGKAPKLLIY
DTSKLASGVPSRFSGSGSGTDFTFTISSLQPEDIATYYCQQWSSNPFT
FGGGTKLEIKR (SEQ ID NO: 78)
EIVLTQSPSSLSASVGDRVTITCRASSSVSYMHWYQQKPGKAPKLLIY
DTSKLASGVPSRFSGSGSGTDFTFTISSLQPEDIATYYCQQWSSNPLT
FGGGTKLEIKR (SEQ ID NO: 79)
EIVLTQSPSSLSASVGDRVTITCRASSSVSYMHWYQQKPGKAPKLLIY
DTSKLASGVPSRFSGSGSGTDFTFTISSLQPEDIATYYCQQHLHIPYT
FGGGTKLEIKR (SEQ ID NO: 200)
EIQMTQSPSSLSASVGDRVTITCSASSSVSYMHWYQQKPGKAPKLLIY
ATSNLASGVPSRFSGSGSGTDFTLTISSLQPEDIATYYCQQWSSNPFT
FGGGTKLEIKR (SEQ ID NO: 201)
EIQMTQSPSSLSASVGDRVTITCSASSSVSYMHWYQQKPGKAPKLLIY
ATSNLASGVPSRFSGSGSGTDFTLTISSLQPEDIATYYCQQWSSNPLT
FGGGTKLEIKR (SEQ ID NO: 202)
EIQMTQSPSSLSASVGDRVTITCSASSSVSYMHWYQQKPGKAPKLLIY
ATSNLASGVPSRFSGSGSGTDFTLTISSLQPEDIATYYCQQHLHIPYT
FGGGTKLEIKR (SEQ ID NO: 203)
EIQMTQSPSSLSASVGDRVTITCSASSRVSYMHWYQQKPGKAPKLLIY
ATSNLASGVPSRFSGSGSGTDFTLTISSLQPEDIATYYCQQWSSNPFT
FGGGTKLEIKR (SEQ ID NO: 204)
EIQMTQSPSSLSASVGDRVTITCSASSRVSYMHWYQQKPGKAPKLLIY
ATSNLASGVPSRFSGSGSGTDFTLTISSLQPEDIATYYCQQWSSNPLT
FGGGTKLEIKR (SEQ ID NO: 205)
EIQMTQSPSSLSASVGDRVTITCSASSRVSYMHWYQQKPGKAPKLLIY
ATSNLASGVPSRFSGSGSGTDFTLTISSLQPEDIATYYCQQHLHIPYT
FGGGTKLEIKR (SEQ ID NO: 206)
EIQMTQSPSSLSASVGDRVTITCSARSSVSYMHWYQQKPGKAPKLLIY
ATSNLASGVPSRFSGSGSGTDFTLTISSLQPEDIATYYCQQWSSNPFT
FGGGTKLEIKR (SEQ ID NO: 207)
EIQMTQSPSSLSASVGDRVTITCSARSSVSYMHWYQQKPGKAPKLLIY
ATSNLASGVPSRFSGSGSGTDFTLTISSLQPEDIATYYCQQWSSNPLT
FGGGTKLEIKR (SEQ ID NO: 208)
EIQMTQSPSSLSASVGDRVTITCSARSSVSYMHWYQQKPGKAPKLLIY
ATSNLASGVPSRFSGSGSGTDFTLTISSLQPEDIATYYCQQHLHIPYT
FGGGTKLEIKR (SEQ ID NO: 209)
EIQMTQSPSSLSASVGDRVTITCRASSSVSYMHWYQQKPGKAPKLLIY
ATSNLASGVPSRFSGSGSGTDFTLTISSLQPEDIATYYCQQWSSNPFT
FGGGTKLEIKR (SEQ ID NO: 210)
EIQMTQSPSSLSASVGDRVTITCRASSSVSYMHWYQQKPGKAPKLLIY
ATSNLASGVPSRFSGSGSGTDFTLTISSLQPEDIATYYCQQWSSNPLT
FGGGTKLEIKR (SEQ ID NO: 211)
EIQMTQSPSSLSASVGDRVTITCRASSSVSYMHWYQQKPGKAPKLLIY
ATSNLASGVPSRFSGSGSGTDFTLTISSLQPEDIATYYCQQHLHIPYT
FGGGTKLEIKR (SEQ ID NO: 212)
EIQMTQSPSSLSASVGDRVTITCSASSSVSYMHWYQQKPGKAPKLLIY
WTSDRYSGVPSRFSGSGSGTDFTLTISSLQPEDIATYYCQQWSSNPFT
FGGGTKLEIKR (SEQ ID NO: 213)
EIQMTQSPSSLSASVGDRVTITCSASSSVSYMHWYQQKPGKAPKLLIY
WTSDRYSGVPSRFSGSGSGTDFTLTISSLQPEDIATYYCQQWSSNPLT
FGGGTKLEIKR (SEQ ID NO: 214)
EIQMTQSPSSLSASVGDRVTITC<u>SASSSVSYMH</u>WYQQKPGKAPKLLIY
<u>WTSDRYS</u>GVPSRFSGSGSGTDFTLTISSLQPEDIATYYC<u>QQHLHIPYT</u>
FGGGTKLEIKR (SEQ ID NO: 215)
EIQMTQSPSSLSASVGDRVTITC<u>SASSRVSYMH</u>WYQQKPGKAPKWY
<u>WTSDRYS</u>GVPSRFSGSGSGTDFTLTISSLQPEDIATYYC<u>QQWSSNPFT</u>
FGGGTKLEIKR (SEQ ID NO: 216)
EIQMTQSPSSLSASVGDRVTITC<u>SASSRVSYMH</u>WYQQKPGKAPKWY
<u>WTSDRYS</u>GVPSRFSGSGSGTDFTLTISSLQPEDIATYYC<u>QQWSSNPLT</u>
FGGGTKLEIKR (SEQ ID NO: 217)
EIQMTQSPSSLSASVGDRVTITC<u>SASSRVSYMH</u>WYQQKPGKAPKWY
<u>WTSDRYS</u>GVPSRFSGSGSGTDFTLTISSLQPEDIATYYC<u>QQHLHIPYT</u>
FGGGTKLEIKR (SEQ ID NO: 218)
EIQMTQSPSSLSASVGDRVTITC<u>SARSSVSYMH</u>WYQQKPGKAPKWY
<u>WTSDRYS</u>GVPSRFSGSGSGTDFTLTISSLQPEDIATYYC<u>QQWSSNPFT</u>
FGGGTKLEIKR (SEQ ID NO: 219)
EIQMTQSPSSLSASVGDRVTITC<u>SARSSVSYMH</u>WYQQKPGKAPKWY
<u>WTSDRYS</u>GVPSRFSGSGSGTDFTLTISSLQPEDIATYYC<u>QQWSSNPLT</u>
FGGGTKLEIKR (SEQ ID NO: 220)
EIQMTQSPSSLSASVGDRVTITC<u>SARSSVSYMH</u>WYQQKPGKAPKWY
<u>WTSDRYS</u>GVPSRFSGSGSGTDFTLTISSLQPEDIATYYC<u>QQHLHIPYT</u>
FGGGTKLEIKR (SEQ ID NO: 221)
EIQMTQSPSSLSASVGDRVTITC<u>RASSSVSYMH</u>WYQQKPGKAPKWY
<u>WTSDRYS</u>GVPSRFSGSGSGTDFTLTISSLQPEDIATYYC<u>QQWSSNPFT</u>
FGGGTKLEIKR (SEQ ID NO: 222)
EIQMTQSPSSLSASVGDRVTITC<u>RASSSVSYMH</u>WYQQKPGKAPKWY
<u>WTSDRYS</u>GVPSRFSGSGSGTDFTLTISSLQPEDIATYYC<u>QQWSSNPLT</u>
FGGGTKLEIKR (SEQ ID NO: 223)
EIQMTQSPSSLSASVGDRVTITC<u>RASSSVSYMH</u>WYQQKPGKAPKWY
<u>WTSDRYS</u>GVPSRFSGSGSGTDFTLTISSLQPEDIATYYC<u>QQHLHIPYT</u>
FGGGTKLEIKR (SEQ ID NO: 224)
EIQMTQSPSSLSASVGDRVTITC<u>SASSSVSYMH</u>WYQQKPGKAPKLLIY
<u>DTSKLAS</u>GVPSRFSGSGSGTDFTLTISSLQPEDIATYYC<u>QQWSSNPFT</u>
FGGGTKLEIKR (SEQ ID NO: 225)
EIQMTQSPSSLSASVGDRVTITC<u>SASSSVSYMH</u>WYQQKPGKAPKLLIY
<u>DTSKLAS</u>GVPSRFSGSGSGTDFTLTISSLQPEDIATYYC<u>QQWSSNPLT</u>
FGGGTKLEIKR (SEQ ID NO: 226)
EIQMTQSPSSLSASVGDRVTITC<u>SASSSVSYMH</u>WYQQKPGKAPKLLIY
<u>DTSKLAS</u>GVPSRFSGSGSGTDFTLTISSLQPEDIATYYC<u>QQHLHIPYT</u>
FGGGTKLEIKR (SEQ ID NO: 227)
EIQMTQSPSSLSASVGDRVTITC<u>SASSRVSYMH</u>WYQQKPGKAPKWY
<u>DTSKLAS</u>GVPSRFSGSGSGTDFTLTISSLQPEDIATYYC<u>QQWSSNPFT</u>
FGGGTKLEIKR (SEQ ID NO: 228)
EIQMTQSPSSLSASVGDRVTITC<u>SASSRVSYMH</u>WYQQKPGKAPKWY
<u>DTSKLAS</u>GVPSRFSGSGSGTDFTLTISSLQPEDIATYYC<u>QQWSSNPLT</u>
FGGGTKLEIKR (SEQ ID NO: 229)
EIQMTQSPSSLSASVGDRVTITC<u>SASSRVSYMH</u>WYQQKPGKAPKWY
<u>DTSKLAS</u>GVPSRFSGSGSGTDFTLTISSLQPEDIATYYC<u>QQHLHIPYT</u>
FGGGTKLEIKR (SEQ ID NO: 230)
EIQMTQSPSSLSASVGDRVTITC<u>SARSSVSYMH</u>WYQQKPGKAPKWY
<u>DTSKLAS</u>GVPSRFSGSGSGTDFTLTISSLQPEDIATYYC<u>QQWSSNPFT</u>
FGGGTKLEIKR (SEQ ID NO: 231)
EIQMTQSPSSLSASVGDRVTITC<u>SARSSVSYMH</u>WYQQKPGKAPKWY
<u>DTSKLAS</u>GVPSRFSGSGSGTDFTLTISSLQPEDIATYYC<u>QQWSSNPLT</u>
FGGGTKLEIKR (SEQ ID NO: 232)
EIQMTQSPSSLSASVGDRVTITC<u>SARSSVSYMH</u>WYQQKPGKAPKWY
<u>DTSKLAS</u>GVPSRFSGSGSGTDFTLTISSLQPEDIATYYC<u>QQHLHIPYT</u>
FGGGTKLEIKR (SEQ ID NO: 233)
EIQMTQSPSSLSASVGDRVTITC<u>RASSSVSYMH</u>WYQQKPGKAPKWY
<u>DTSKLAS</u>GVPSRFSGSGSGTDFTLTISSLQPEDIATYYC<u>QQWSSNPFT</u>
FGGGTKLEIKR (SEQ ID NO: 234)
EIQMTQSPSSLSASVGDRVTITC<u>RASSSVSYMH</u>WYQQKPGKAPKWY
<u>DTSKLAS</u>GVPSRFSGSGSGTDFTLTISSLQPEDIATYYC<u>QQWSSNPLT</u>
FGGGTKLEIKR (SEQ ID NO: 235)
EIQMTQSPSSLSASVGDRVTITC<u>RASSSVSYMH</u>WYQQKPGKAPKWY
<u>DTSKLAS</u>GVPSRFSGSGSGTDFTLTISSLQPEDIATYYC<u>QQHLHIPYT</u>
FGGGTKLEIKR

In a further embodiment, the present invention provides a humanized anti-Globo H antibody or an antigen-binding portion thereof, comprising (i) a heavy chain variable region comprising an amino acid sequence having at least 85% identical to any of the amino acid sequences of SEQ ID NOs: 80 to 103, and (ii) a light chain variable region comprising an amino acid sequence having at least 80% identical to any of the amino acid sequence of SEQ ID NOs: 104 to 139. Preferably, the sequence identity as mentioned above is at least 90%, 91%, 91%, 92%, 93%, 94%, 95%, 96%, 97%, 98% or 99%.

In another further embodiment, the present invention provides a humanized anti-Globo H antibody or an antigen-binding portion thereof, comprising (i) a heavy chain variable region comprising an amino acid sequence selected from the group consisting of SEQ ID NOs: 80 to 103, and (ii) a light chain variable region comprising an amino acid sequence selected from the group consisting of SEQ ID NO: 104 to 139.

In another embodiment, the humanized anti-Globo H antibody or an antigen-binding portion thereof comprises a heavy chain variable region comprising an amino acid sequence consisting of SEQ ID NO: 90, and a light chain variable region comprising an amino acid sequence consisting of SEQ ID NO: 135 (MK1 antibody).

Heavy Chain Variable Region of MK1 Series

<u>(QVTLKESGPALVKPTQTLTLTCTFS</u>\*\*\*\*\*\*\*\*\*\*\*\*<u>WIRQPPGKALE</u>
<u>WLA</u>\*\*\*\*\*\*\*\*\*\*\*\*\*<u>LKSRLTISKDTSKNQVVLTMTNMDPVDTATYYC</u>
<u>AR</u>\*\*\*\*\*\*\*\*\*\*\*\*\*<u>WGQGTLVTVSS)</u>

(SEQ ID NO: 80)
QVTLKESGPALVKPTQTLTLTCTFS<u>GFSLSTFDMGVG</u>WIRQPPGKALEW
LA<u>HIWWDDDKYYNPALKSRLTISKDTSKNQVVLTMTNMDPVDTATYYCA
R<u>LYGNYLTSFYCDY</u>WGQGTLVTVSS (SEQ ID NO: 81)
QVTLKESGPALVKPTQTLTLTCTFS<u>GFSLSTFDMGVG</u>WIRQPPGKALEW
LA<u>HIWWDDDKYYNPALKSRLTISKDTSKNQVVLTMTNMDPVDTATYYCA
R<u>LSGNYLTSFYCDY</u>WGQGTLVTVSS (SEQ ID NO: 82)
QVTLKESGPALVKPTQTLTLTCTFS<u>GFSLSTFDMGVG</u>WIRQPPGKALEW
LA<u>HIWWDDDKYYNPAL</u>KSRLTISKDTSKNQVVLTMTNMDPVDTATYYCA
R<u>LYGNYLRSYYCDY</u>WGQGTLVTVSS (SEQ ID NO: 83)
QVTLKESGPALVKPTQTLTLTCTFS<u>GSSLSTFDVGVG</u>WIRQPPGKALEW
LA<u>HIWWDDDKYYNPAL</u>KSRLTISKDTSKNQVVLTMTNMDPVDTATYYCA
R<u>LYGNYLTSFYCDY</u>WGQGTLVTVSS (SEQ ID NO: 84)
QVTLKESGPALVKPTQTLTLTCTFS<u>GSSLSTFDVGVG</u>WIRQPPGKALEW
LA<u>HIWWDDDKYYNPAL</u>KSRLTISKDTSKNQVVLTMTNMDPVDTATYYCA
R<u>LSGNYLTSFYCDY</u>WGQGTLVTVSS (SEQ ID NO: 85)
QVTLKESGPALVKPTQTLTLTCTFS<u>GSSLSTFDVGVG</u>WIRQPPGKALEW
LA<u>HIWWDDDKYYNPAL</u>KSRLTISKDTSKNQVVLTMTNMDPVDTATYYCA
R<u>LYGNYLRSYYCDY</u>WGQGTLVTVSS (SEQ ID NO: 86)
QVTLKESGPALVKPTQTLTLTCTFS<u>GFSLGTFDLGIG</u>WIRQPPGKALEW
LA<u>HIWWDDDKYYNPAL</u>KSRLTISKDTSKNQVVLTMTNMDPVDTATYYCA
R<u>LYGNYLTSFYCDY</u>WGQGTLVTVSS (SEQ ID NO: 87)
QVTLKESGPALVKPTQTLTLTCTFS<u>GFSLGTFDLGIG</u>WIRQPPGKALEW
LA<u>HIWWDDDKYYNPAL</u>KSRLTISKDTSKNQVVLTMTNMDPVDTATYYCA
R<u>LSGNYLTSFYCDY</u>WGQGTLVTVSS (SEQ ID NO: 88)
QVTLKESGPALVKPTQTLTLTCTFS<u>GFSLGTFDLGIG</u>WIRQPPGKALEW
LA<u>HIWWDDDKYYNPAL</u>KSRLTISKDTSKNQVVLTMTNMDPVDTATYYCA
R<u>LYGNYLRSYYCDY</u>WGQGTLVTVSS (SEQ ID NO: 89)
QVTLKESGPALVKPTQTLTLTCTFS<u>GFSLSTFDLGIG</u>WIRQPPGKALEW
LA<u>HIWGDDDKYYNPAL</u>KSRLTISKDTSKNQVVLTMTNMDPVDTATYYCA
R<u>LYGNYLTSFYCDY</u>WGQGTLVTVSS (SEQ ID NO: 90)
QVTLKESGPALVKPTQTLTLTCTFS<u>GFSLSTFDLGIG</u>WIRQPPGKALEW
LA<u>HIWWDDDKYYNPAL</u>KSRLTISKDTSKNQVVLTMTNMDPVDTATYYCA
R<u>LYGNYLTSFYCDY</u>WGQGTLVTVSS (SEQ ID NO: 91)
QVTLKESGPALVKPTQTLTLTCTFS<u>GFSLSTFDLGIG</u>WIRQPPGKALEW
LA<u>HIWWDDDKYYNPAL</u>KSRLTISKDTSKNQVVLTMTNMDPVDTATYYCA
R<u>LYGNYLRSYYCDY</u>WGQGTLVTVSS (SEQ ID NO: 92)
QVTLKESGPALVKPTQTLTLTCTFS<u>GFSLSTFDMGVG</u>WIRQPPGKALEW
LA<u>HIWGDDDKYYNPAL</u>KSRLTISKDTSKNQVVLTMTNMDPVDTATYYCA
R<u>LYGNYLTSFYCDY</u>WGQGTLVTVSS (SEQ ID NO: 93)
QVTLKESGPALVKPTQTLTLTCTFS<u>GFSLSTFDMGVG</u>WIRQPPGKALEW
LA<u>HIWGDDDKYYNPAL</u>KSRLTISKDTSKNQVVLTMTNMDPVDTATYYCA
R<u>LSGNYLTSFYCDY</u>WGQGTLVTVSS (SEQ ID NO: 94)
QVTLKESGPALVKPTQTLTLTCTFS<u>GFSLSTFDMGVG</u>WIRQPPGKALEW
LA<u>HIWGDDDKYYNPAL</u>KSRLTISKDTSKNQVVLTMTNMDPVDTATYYCA
R<u>LYGNYLRSYYCDY</u>WGQGTLVTVSS (SEQ ID NO: 95)
QVTLKESGPALVKPTQTLTLTCTFS<u>GSSLSTFDVGVG</u>WIRQPPGKALEW
LA<u>HIWGDDDKYYNPAL</u>KSRLTISKDTSKNQVVLTMTNMDPVDTATYYCA
R<u>LYGNYLTSFYCDY</u>WGQGTLVTVSS (SEQ ID NO: 96)
QVTLKESGPALVKPTQTLTLTCTFS<u>GSSLSTFDVGVG</u>WIRQPPGKALEW
LA<u>HIWGDDDKYYNPAL</u>KSRLTISKDTSKNQVVLTMTNMDPVDTATYYCA
R<u>LSGNYLTSFYCDY</u>WGQGTLVTVSS (SEQ ID NO: 97)
QVTLKESGPALVKPTQTLTLTCTFS<u>GSSLSTFDVGVG</u>WIRQPPGKALEW
LA<u>HIWGDDDKYYNPAL</u>KSRLTISKDTSKNQVVLTMTNMDPVDTATYYCA
R<u>LYGNYLRSYYCDY</u>WGQGTLVTVSS (SEQ ID NO: 98)
QVTLKESGPALVKPTQTLTLTCTFS<u>GFSLGTFDLGIG</u>WIRQPPGKALEW
LA<u>HIWGDDDKYYNPAL</u>KSRLTISKDTSKNQVVLTMTNMDPVDTATYYCA
R<u>LYGNYLTSFYCDY</u>WGQGTLVTVSS (SEQ ID NO: 99)
QVTLKESGPALVKPTQTLTLTCTFS<u>GFSLGTFDLGIG</u>WIRQPPGKALEW
LA<u>HIWGDDDKYYNPAL</u>KSRLTISKDTSKNQVVLTMTNMDPVDTATYYCA
R<u>LSGNYLTSFYCDY</u>WGQGTLVTVSS (SEQ ID NO: 100)
QVTLKESGPALVKPTQTLTLTCTFS<u>GFSLGTFDLGIG</u>WIRQPPGKALEW
LA<u>HIWGDDDKYYNPAL</u>KSRLTISKDTSKNQVVLTMTNMDPVDTATYYCA
R<u>LYGNYLRSYYCDY</u>WGQGTLVTVSS (SEQ ID NO: 101)
QVTLKESGPALVKPTQTLTLTCTFS<u>GFSLSTFDLGIG</u>WIRQPPGKALEW
LA<u>HIWGDDDKYYNPAL</u>KSRLTISKDTSKNQVVLTMTNMDPVDTATYYCA
R<u>LYGNYLTSFYCDY</u>WGQGTLVTVSS (SEQ ID NO: 102)
QVTLKESGPALVKPTQTLTLTCTFS<u>GFSLSTFDLGIG</u>WIRQPPGKALEW
LA<u>HIWGDDDKYYNPAL</u>KSRLTISKDTSKNQVVLTMTNMDPVDTATYYCA
R<u>LSGNYLTSFYCDY</u>WGQGTLVTVSS (SEQ ID NO: 103)
QVTLKESGPALVKPTQTLTLTCTFS<u>GFSLSTFDLGIG</u>WIRQPPGKALEW
LA<u>HIWGDDDKYYNPAL</u>KSRLTISKDTSKNQVVLTMTNMDPVDTATYYCA
R<u>LYGNYLRSYYCDY</u>WGQGTLVTVSS

Light Chain Variable Region of MK1 Series

<u>(DVVMTQSPAFLSVTPGEKVTITC</u>**********<u>WYQQKPDQAPKLLIK</u>
<u>*****GVPSRFSGSGSGTDFTFTISSLEAEDAATYYC</u>*******<u>F</u>
<u>GQGTKLEIKR)</u>

(SEQ ID NO: 104)
DVVMTQSPAFLSVTPGEKVTITC<u>SASSSVSYMH</u>WYQQKPDQAPKLLIK
<u>ATSNLAS</u>GVPSRFSGSGSGTDFTFTISSLEAEDAATYYC<u>QQWSSNPFT</u>
FGQGTKLEIKR (SEQ ID NO: 105)
DVVMTQSPAFLSVTPGEKVTITC<u>SASSSVSYMH</u>WYQQKPDQAPKLLIK
<u>ATSNLAS</u>GVPSRFSGSGSGTDFTFTISSLEAEDAATYYC<u>QQWSSNPLT</u>
FGQGTKLEIKR (SEQ ID NO: 106)
DVVMTQSPAFLSVTPGEKVTITC<u>SASSSVSYMH</u>WYQQKPDQAPKLLIK
<u>ATSNLAS</u>GVPSRFSGSGSGTDFTFTISSLEAEDAATYYC<u>QQHLHIPYT</u>
FGQGTKLEIKR (SEQ ID NO: 107)
DVVMTQSPAFLSVTPGEKVTITC<u>SASSRVSYMH</u>WYQQKPDQAPKLLIK
<u>ATSNLAS</u>GVPSRFSGSGSGTDFTFTISSLEAEDAATYYC<u>QQWSSNPFT</u>
FGQGTKLEIKR (SEQ ID NO: 108)
DVVMTQSPAFLSVTPGEKVTITC<u>SASSRVSYMH</u>WYQQKPDQAPKLLIK
<u>ATSNLAS</u>GVPSRFSGSGSGTDFTFTISSLEAEDAATYYC<u>QQWSSNPLT</u>
FGQGTKLEIKR (SEQ ID NO: 109)
DVVMTQSPAFLSVTPGEKVTITC<u>SASSRVSYMH</u>WYQQKPDQAPKLLIK
<u>ATSNLAS</u>GVPSRFSGSGSGTDFTFTISSLEAEDAATYYC<u>QQHLHIPYT</u>
FGQGTKLEIKR (SEQ ID NO: 110)
DVVMTQSPAFLSVTPGEKVTITC<u>SARSSVSYMH</u>WYQQKPDQAPKLLIK
<u>ATSNLAS</u>GVPSRFSGSGSGTDFTFTISSLEAEDAATYYC<u>QQWSSNPFT</u>
FGQGTKLEIKR (SEQ ID NO: 111)
DVVMTQSPAFLSVTPGEKVTITC<u>SARSSVSYMH</u>WYQQKPDQAPKLLIK
<u>ATSNLAS</u>GVPSRFSGSGSGTDFTFTISSLEAEDAATYYC<u>QQWSSNPLT</u>
FGQGTKLEIKR (SEQ ID NO: 112)
DVVMTQSPAFLSVTPGEKVTITC<u>SARSSVSYMH</u>WYQQKPDQAPKLLIK
<u>ATSNLAS</u>GVPSRFSGSGSGTDFTFTISSLEAEDAATYYC<u>QQHLHIPYT</u>
FGQGTKLEIKR (SEQ ID NO: 113)
DVVMTQSPAFLSVTPGEKVTITC<u>RASSSVSYMH</u>WYQQKPDQAPKLLIK
<u>ATSNLAS</u>GVPSRFSGSGSGTDFTFTISSLEAEDAATYYC<u>QQWSSNPFT</u>
FGQGTKLEIKR (SEQ ID NO: 114)
DVVMTQSPAFLSVTPGEKVTITC<u>RASSSVSYMH</u>WYQQKPDQAPKLLIK
<u>ATSNLAS</u>GVPSRFSGSGSGTDFTFTISSLEAEDAATYYC<u>QQWSSNPLT</u>
FGQGTKLEIKR (SEQ ID NO: 115)
DVVMTQSPAFLSVTPGEKVTITC<u>RASSSVSYMH</u>WYQQKPDQAPKLLIK
<u>ATSNLAS</u>GVPSRFSGSGSGTDFTFTISSLEAEDAATYYC<u>QQHLHIPYT</u>
FGQGTKLEIKR (SEQ ID NO: 116)
DVVMTQSPAFLSVTPGEKVTITC<u>SASSSVSYMH</u>WYQQKPDQAPKLLIK
<u>WTSDRYS</u>GVPSRFSGSGSGTDFTFTISSLEAEDAATYYC<u>QQWSSNPFT</u>
FGQGTKLEIKR (SEQ ID NO: 117)
DVVMTQSPAFLSVTPGEKVTITC<u>SASSSVSYMH</u>WYQQKPDQAPKLLIK
<u>WTSDRYS</u>GVPSRFSGSGSGTDFTFTISSLEAEDAATYYC<u>QQWSSNPLT</u>
FGQGTKLEIKR (SEQ ID NO: 118)
DVVMTQSPAFLSVTPGEKVTITC<u>SASSSVSYMH</u>WYQQKPDQAPKLLIK
<u>WTSDRYS</u>GVPSRFSGSGSGTDFTFTISSLEAEDAATYYC<u>QQHLHIPYT</u>
FGQGTKLEIKR (SEQ ID NO: 119)
DVVMTQSPAFLSVTPGEKVTITC<u>SASSRVSYMH</u>WYQQKPDQAPKLLIK
<u>WTSDRYS</u>GVPSRFSGSGSGTDFTFTISSLEAEDAATYYC<u>QQWSSNPFT</u>
FGQGTKLEIKR (SEQ ID NO: 120)
DVVMTQSPAFLSVTPGEKVTITC<u>SASSRVSYMH</u>WYQQKPDQAPKLLIK
<u>WTSDRYS</u>GVPSRFSGSGSGTDFTFTISSLEAEDAATYYC<u>QQWSSNPLT</u>
FGQGTKLEIKR (SEQ ID NO: 121)
DVVMTQSPAFLSVTPGEKVTITC<u>SASSRVSYMH</u>WYQQKPDQAPKLLIK
<u>WTSDRYS</u>GVPSRFSGSGSGTDFTFTISSLEAEDAATYYC<u>QQHLHIPYT</u>
FGQGTKLEIKR (SEQ ID NO: 122)
DVVMTQSPAFLSVTPGEKVTITC<u>SARSSVSYMH</u>WYQQKPDQAPKLLIK
<u>WTSDRYS</u>GVPSRFSGSGSGTDFTFTISSLEAEDAATYYC<u>QQWSSNPFT</u>
FGQGTKLEIKR (SEQ ID NO: 123)
DVVMTQSPAFLSVTPGEKVTITC<u>SARSSVSYMH</u>WYQQKPDQAPKLLIK
<u>WTSDRYS</u>GVPSRFSGSGSGTDFTFTISSLEAEDAATYYC<u>QQWSSNPLT</u>
FGQGTKLEIKR (SEQ ID NO: 124)
DVVMTQSPAFLSVTPGEKVTITC<u>SARSSVSYMH</u>WYQQKPDQAPKLLIK
<u>WTSDRYS</u>GVPSRFSGSGSGTDFTFTISSLEAEDAATYYC<u>QQHLHIPYT</u>
FGQGTKLEIKR (SEQ ID NO: 125)
DVVMTQSPAFLSVTPGEKVTITC<u>RASSSVSYMH</u>WYQQKPDQAPKLLIK
<u>WTSDRYS</u>GVPSRFSGSGSGTDFTFTISSLEAEDAATYYC<u>QQWSSNPFT</u>
FGQGTKLEIKR (SEQ ID NO: 126)
DVVMTQSPAFLSVTPGEKVTITC<u>RASSSVSYMH</u>WYQQKPDQAPKLLIK
<u>WTSDRYS</u>GVPSRFSGSGSGTDFTFTISSLEAEDAATYYC<u>QQWSSNPLT</u>
FGQGTKLEIKR (SEQ ID NO: 127)
DVVMTQSPAFLSVTPGEKVTITC<u>RASSSVSYMH</u>WYQQKPDQAPKLLIK
<u>WTSDRYS</u>GVPSRFSGSGSGTDFTFTISSLEAEDAATYYC<u>QQHLHIPYT</u>
FGQGTKLEIKR (SEQ ID NO: 128)
DVVMTQSPAFLSVTPGEKVTITC<u>SASSSVSYMH</u>WYQQKPDQAPKLLIK
<u>DTSKLAS</u>GVPSRFSGSGSGTDFTFTISSLEAEDAATYYC<u>QQWSSNPFT</u>
FGQGTKLEIKR (SEQ ID NO: 129)
DVVMTQSPAFLSVTPGEKVTITC<u>SASSSVSYMH</u>WYQQKPDQAPKLLIK
<u>DTSKLAS</u>GVPSRFSGSGSGTDFTFTISSLEAEDAATYYC<u>QQWSSNPLT</u>
FGQGTKLEIKR (SEQ ID NO: 130)
DVVMTQSPAFLSVTPGEKVTITC<u>SASSSVSYMH</u>WYQQKPDQAPKLLIK
<u>DTSKLAS</u>GVPSRFSGSGSGTDFTFTISSLEAEDAATYYC<u>QQHLHIPYT</u>
FGQGTKLEIKR (SEQ ID NO: 131)
DVVMTQSPAFLSVTPGEKVTITC<u>SASSRVSYMH</u>WYQQKPDQAPKLLIK
<u>DTSKLAS</u>GVPSRFSGSGSGTDFTFTISSLEAEDAATYYC<u>QQWSSNPFT</u>
FGQGTKLEIKR (SEQ ID NO: 132)
DVVMTQSPAFLSVTPGEKVTITC<u>SASSRVSYMH</u>WYQQKPDQAPKLLIK
<u>DTSKLAS</u>GVPSRFSGSGSGTDFTFTISSLEAEDAATYYC<u>QQWSSNPLT</u>
FGQGTKLEIKR (SEQ ID NO: 133)
DVVMTQSPAFLSVTPGEKVTITC<u>SASSRVSYMH</u>WYQQKPDQAPKLLIK
<u>DTSKLAS</u>GVPSRFSGSGSGTDFTFTISSLEAEDAATYYC<u>QQHLHIPYT</u>
FGQGTKLEIKR (SEQ ID NO: 134)
DVVMTQSPAFLSVTPGEKVTITC<u>SARSSVSYMH</u>WYQQKPDQAPKLLIK
<u>DTSKLAS</u>GVPSRFSGSGSGTDFTFTISSLEAEDAATYYC<u>QQWSSNPFT</u>
FGQGTKLEIKR (SEQ ID NO: 135)
DVVMTQSPAFLSVTPGEKVTITC<u>SARSSVSYMH</u>WYQQKPDQAPKLLIK
<u>DTSKLAS</u>GVPSRFSGSGSGTDFTFTISSLEAEDAATYYC<u>QQWSSNPLT</u>
FGQGTKLEIKR (SEQ ID NO: 136)
DVVMTQSPAFLSVTPGEKVTITC<u>SARSSVSYMH</u>WYQQKPDQAPKLLIK
<u>DTSKLAS</u>GVPSRFSGSGSGTDFTFTISSLEAEDAATYYC<u>QQHLHIPYT</u>
FGQGTKLEIKR (SEQ ID NO: 137)
DVVMTQSPAFLSVTPGEKVTITC<u>RASSSVSYMH</u>WYQQKPDQAPKLLIK
<u>DTSKLAS</u>GVPSRFSGSGSGTDFTFTISSLEAEDAATYYC<u>QQWSSNPFT</u>
FGQGTKLEIKR (SEQ ID NO: 138)
DVVMTQSPAFLSVTPGEKVTITC<u>RASSSVSYMH</u>WYQQKPDQAPKLLIK
<u>DTSKLAS</u>GVPSRFSGSGSGTDFTFTISSLEAEDAATYYC<u>QQWSSNPLT</u>
FGQGTKLEIKR (SEQ ID NO: 139)
DVVMTQSPAFLSVTPGEKVTITC<u>RASSSVSYMH</u>WYQQKPDQAPKLLIK
<u>DTSKLAS</u>GVPSRFSGSGSGTDFTFTISSLEAEDAATYYC<u>QQHLHIPYT</u>
FGQGTKLEIKR

A humanized antibody has one or more amino acid residues from a source that is non-human. The non-human amino acid residues are often referred to as "import" residues, and are typically taken from an "import" variable domain. Humanization can be performed generally following conventional method known in the art, by substituting rodent CDRs or CDR sequences for the corresponding sequences of a human antibody. Accordingly, such "humanized" antibodies are antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. The sequence of the variable domain of a rodent antibody is screened against the entire library of known human variable-domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

In one embodiment, the present invention provides a chimeric anti-Globo H antibody or an antigen-binding portion thereof, comprising (i) a heavy chain variable region comprising an amino acid sequence having at least 85% identical to any of the amino acid sequences of SEQ ID NOs: 140-163 wherein the last third sequence V of the amino acid sequences is changed as I, and (ii) a light chain variable region comprising an amino acid sequence having at least 80% identical to any of the amino acid sequence of SEQ ID NO:164-199. Preferably, the sequence identity as mentioned above is at least 90%, 91%, 91%, 92%, 93%, 94%, 95%, 96%, 97%, 98% or 99%.

In one embodiment, the present invention provides a chimeric anti-Globo H antibody, comprising (i) a heavy chain variable region comprising an amino acid sequence having at least 85% identical to the amino acid sequences of SEQ ID NO: 147 wherein the last third sequence V of the amino acid sequence is changed as I, and (ii) a light chain variable region comprising an amino acid sequence having at least 85% identical to the amino acid sequence of SEQ ID NO: 195. In a further embodiment, the present invention provides an isolated anti-Globo H antibody (cMZ-2), comprising (i) a heavy chain variable region comprising an amino acid sequence consisting of SEQ ID NO: 147 wherein the last third sequence V of the amino acid sequences is changed as I, and (ii) a light chain variable region comprising an amino acid sequence consisting of SEQ ID NO: 195.

The production of the chimeric antibody can be produced according to conventional methods known in the art. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

Compositions of Antibodies of the Invention

In another aspect, the present invention provides a pharmaceutical composition comprising an anti-Globo H antibody or an antigen-binding portion thereof. The present antibody can also be formulated into a pharmaceutical composition. In addition to the antibody or an antigen-binding portion thereof, the pharmaceutical composition further comprises a pharmaceutically acceptable carrier.

Administration of the anti-Globo H antibody or an antigen-binding portion thereof described herein, can include formulation into pharmaceutical compositions or pharmaceutical formulations for parenteral administration, e.g., intravenous; mucosal, e.g., intranasal; ocular, or other mode of administration. In some embodiments, the anti-Globo H antibody or an antigen-binding portion thereof described herein can be administered along with any pharmaceutically acceptable carrier compound, material, or composition which results in an effective treatment in the subject. Thus, a pharmaceutical formulation/composition for use in the methods described herein can contain an anti-Globo H antibody or an antigen-binding portion thereof as described herein in combination with one or more pharmaceutically acceptable carriers.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an anti-Globo H antibody or an antigen-binding portion thereof as described herein. Each carrier must be "acceptable" in the sense of being compatible with the other ingredients of the formulation and not injurious to the patient. The terms "excipient", "carrier", "pharmaceutically acceptable carrier", or the like are used interchangeably herein.

The anti-Globo H antibody or an antigen-binding portion thereof as described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a anti-Globo H antibody or an antigen-binding portion thereof as described herein can be implanted into a patient or injected using a drug delivery system.

According to various working examples presented below, adult C57BL/6 mice (weight 20-25 grams) administered with the present antibody twice a week achieved reduced tumor size on 3 to 21 days after inoculation. Hence, in certain embodiments of the present disclosure, the therapeutically effective amount of the antibody for mice could be expressed as 0.8-100 mg/kg body weight. HED of the above-mentioned murine effective amount is about 0.65-81.5 mg/kg body weight. According to various embodiments of the present disclosure, when the subject is human, the therapeutically effective amount of the antibody can be at least 1 mg/kg. Depending on the type and severity of the disease, about 1 mg/kg to 150 mg/kg (e.g., 0.1-20 mg/kg) of an anti-Globo H antibody or an antigen-binding portion thereof as described herein is an initial candidate dosage for administration to a subject, whether, for example, by one or more separate administrations, or by continuous infusion. A typical daily dosage might range from about 1 mg/kg to about 100 mg/kg or more, depending on the factors mentioned above. Typical dosages include, for example, 5 mg/kg, 10 mg/kg, 20 mg/kg, and 30 mg/kg. For repeated administrations over several days or longer, depending on the condition, the treatment is sustained until, for example, the cancer is treated, as measured by the methods described above or known in the art.

Modes of Administration

In another aspect, the invention provides a method of treating and/or preventing a cancer, comprising administering to a subject in need thereof a therapeutically effective amount of an anti-Globo H antibody or an antigen-binding portion thereof as described herein or a pharmaceutical composition comprising an anti-Globo H antibody or an antigen-binding portion thereof as described herein.

The administration of the antibody or the pharmaceutical composition comprising the same to a subject confers passive protection to the subject and thereby provides the intended therapeutic effect to a cancer, such as tumor-associated carbohydrate-expressing cancer; preferably, breast cancer, ovarian cancer, pancreatic cancer, prostate cancer, colorectal cancer and lung cancer.

In some embodiments, the anti-Globo H antibody or an antigen-binding portion thereof as described herein or a pharmaceutical composition comprising an anti-Globo H antibody or an antigen-binding portion thereof as described herein is administered to a subject having a cancer to be inhibited by any mode of administration that delivers the agent systemically or to a desired surface or target, and can include, but is not limited to, injection, infusion, instillation, and inhalation administration. To the extent that anti-Globo H antibody or an antigen-binding portion thereof as described herein or a pharmaceutical composition comprising an anti-Globo H antibody or an antigen-binding portion thereof as described herein can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In preferred embodiments, the anti-Globo H antibody or an antigen-binding portion thereof as described herein or a pharmaceutical composition comprising an anti-Globo H antibody or an antigen-binding portion thereof as described herein for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

The methods provided herein for inhibiting or treating cancer in subject having or at risk for cancer by administering to the subject a therapeutically effective amount of an anti-Globo H antibody or an antigen-binding portion thereof as described herein or a pharmaceutical composition comprising an anti-Globo H antibody or an antigen-binding portion thereof as described herein, can, in some embodiments, further comprise administration one or more additional treatments such as angiogenic inhibitors, chemotherapy, radiation, surgery, or other treatments known to those of skill in the art to prevent and/or treat cancer.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Example 1 Production of Monoclonal Antibody, Chimeric Antibody and Humanized Antibody Against Globo H Adult female C57BL/6 mice (n=3 each group; 5 weeks old; average weight 16-20 grams; purchased from Biolasco, Taiwan) were immunized by subcutaneous injection with 6 μg of Globo H-PADRE glycopeptide wherein PARDE represents a polypeptide of AKXVAAWTLKAAA (SEQ ID NO:238), and 50 μl of complete Freund's adjuvant (CFA; from Sigma). Four immunizations were given at a 2-week interval. Three days after the fourth immunization, immunized splenocytes were harvest and washed with serum-free medium. Subsequently, $1 \times 10^8$ of single cell suspended splenocytes were mixed with $2 \times 10^7$ of FO cells, and cell fusion was performed in 1 ml of 50% PEG 1500 solution (Roche) at 37° C. followed by drop-wise addition of 13 ml of warmed RPMI medium (Gibco). Fused cells were centrifuged and washed twice with complete medium. Cells were then re-suspended in complete medium with 1× BM-Conditioned H1 Hybridoma cloning supplement (Roche) and seeded into 96-well plates. For target specific B cell-myeloma cells fusion, immunized splenocytes were incubated with Globo H-biotin (10 μg/ml) in serum-free RPMI medium for 3 hours at 4° C. After being washed three times with the same medium, Globo H-binotin-bearing cells were resuspended at a concentration of $1 \times 10^8$ cells/ml and incubated with streptavidin (50 μg/ml) for 30 minutes at 4° C.

Meanwhile, FO cells were incubated with 50 µg/ml of NHS-biotin for 1 hour at 4° C. Both treated cells were then washed three times with serum-free RPMI medium. Then, $1 \times 10^8$ splenocytes and $2 \times 10^7$ FO cells were mixed together, and chemical cell fusion was performed as describe above. After cell fusion, cells were cultured in RPMI 1640 medium containing 1×HAT medium (Gibco) for further selection.

Monoclonal antibody-producing hybridoma cell lines were screened through limited dilution by ELISA assay on plate coated with Globo H-biotin antigen. Five clones (named MZ-1 to MZ-5, respectively) capable of secreting high-titers of anti-Globo H IgG or IgM antibodies were obtained.

Supernatants from these hybridoma lines were also subjected to cell binding assay. Briefly, 100 µl of the supernatant from the hybridoma culture was incubated with 2×105 of MCF-7 cells and then analyzed by flow cytometry with appropriate fluorescent secondary antibody mentioned below. The cells were washed once with 2 ml of 1×PBS. After centrifugation, the wash buffer was discarded and cells were resuspended in 100 µl of 1:100 diluted PE anti-mouse IgG-Fc (Jackson immunoresearch) or 100 µl of 1:100 diluted PE anti-mouse IgM (eBioscience) and incubated again at room temperature for 20 minutes. The cells were washed with PBS and resuspended in 200 µl of 1×PBS after centrifugation. The binding of antibodies with cells were detected by flow cytometry. The results provided in FIGS. 1A to E reveal that the monoclonal antibody produced by MZ-2 hybridoma (see FIG. 1C) (hereinafter, the MZ-2 antibody) had good binding affinity to MCF-7 cells. For comparison purpose, a commercially available anti-Globo H IgG3 antibody (see FIG. E), VK9 antibody (see FIG. B) (eBioscience), was also analyzed.

Variable regions of heavy and light chains of MZ-2 antibody were first cloned to human IgG1 and kappa chain conserved region expression vectors to form mouse-human chimeric MZ-2 (cMZ-2). The cMZ-2 antibody has been gone through humanization by CDR-grafting based on structure analysis and sequence homology. The humanized MZ-2 antibody (hMZ-2) could be readily expressed as a recombinant IgG in mammalian cells and retains the antigen-binding affinity and specificity of the parent mouse antibody. We further improved its binding affinity with selective mutations of CDR and framework sequences that flank the CDR. The humanized construct was further transfected into FO cells by electroporation and selected by associated antibiotics to generate stable expression clones. Antibodies produced from the FO cells were checked by flow cytometry analysis. To obtain large-scale hMZ-2 antibodies for anti-tumor assay in vivo, 1×106 of hMZ-2 expression FO cells were first i.p. injected into NOD/SCID mice. Ascites from these mice were harvest after 2 weeks and passed through protein G agarose column to purify the generated antibody. The thus-obtained hMZ-2 antibodies were sequenced. The hMZ-2 antibody, hMz-2Lw (variable region of heavy chain: SEQ ID No. 27; variable region of light chain: SEQ ID No. 75 and MK1 (variable region of heavy chain: SEQ ID No. 290; variable region of light chain: SEQ ID No. 135), were used in the following examples.

Figure 2:
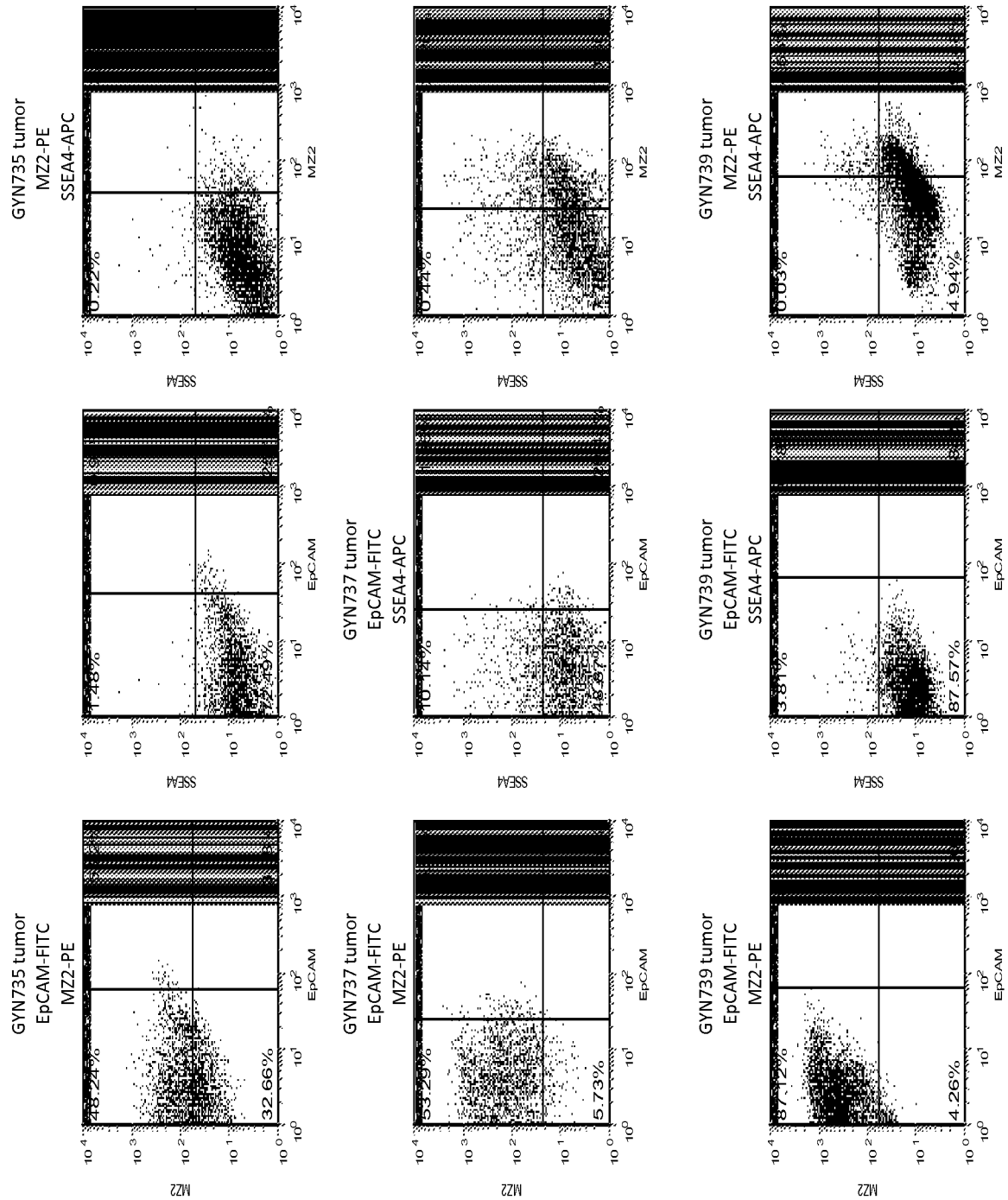
FIG. 2 illustrate the binding affinity of anti-Globo H IgG antibody to primary ovarian cancer cells according to a few working examples of the present disclosure.

Example 2 Binding Affinity of MZ-2 Monoclonal Antibody to Primary Ovarian Cancer Cells Primary human ovarian cancer tissues were obtained under the approval of IRB and patient consent. Ovarian cancer tissues were digested by MASC Tumor Dissociation kit (MASC, 130-095-929). The single cell suspension was stained with MZ-2 monoclonal antibody (10 µg/ml; 100 µl) for 30 minutes at 4° C., and stained with secondary antibody anti-mouse IgG1 PE (1:50; eBioscience, 2-405-82), then fixed with 4% paraformaldehyde for 1 min at RT. The cell were then stained with FITC-conjugated mouse anti-human EpCAM (1:50; biolegend, 324204), and mouse anti-human SSEA4 (1:50; biolegend, 330408) for 30 min at 4° C. Flow cytometric analysis was conducted on a Becton Dickinson FACScan (BD FACSCalibur). FIG. 2 demonstrate that the present MZ-2 monoclonal antibody exhibited good binding to primary ovarian cancer cells. Most epithelial primary cancer cells were stained with either MZ-2 or SSEA4 antibody showing by representative flow cytometry. EpCAM staining here represents a marker of epithelial cell.

Example 3 Specificity Assay of MZ-2 Antibody

Biotinylated-carbohydrates were conjugated on BD Cytometric Beads via Avidin by Functional Bead Conjugation Buffer Set (BD). First, 75 µL of the functional beads were sonicated and incubated with 1.9 µL of 1M DTT at room temperature for 1 hr. At the same time, 20 uL of each biotin-carbohydrate (0.2 mg/mL) was mixed with 90 µg of maleimide activated neutrAvidin (1 mg/mL in coupling buffer; Pierce) and incubated at room temperature for 1 hr. The beads were washed 3 times with 1 mL of coupling buffer and resuspended in 20 µL of coupling buffer. The carbohydrate were then mixed with designed beads and incubated with further one hour. 2 µL of N-Ethylmaleimide (2 mg/mL on DMSO, Pierce) was then added into the conjugated beads and incubated for further 15 min. After 3 time wash, the beads were suspended in 500 µL of storage buffer and ready for use.

Figure 3:
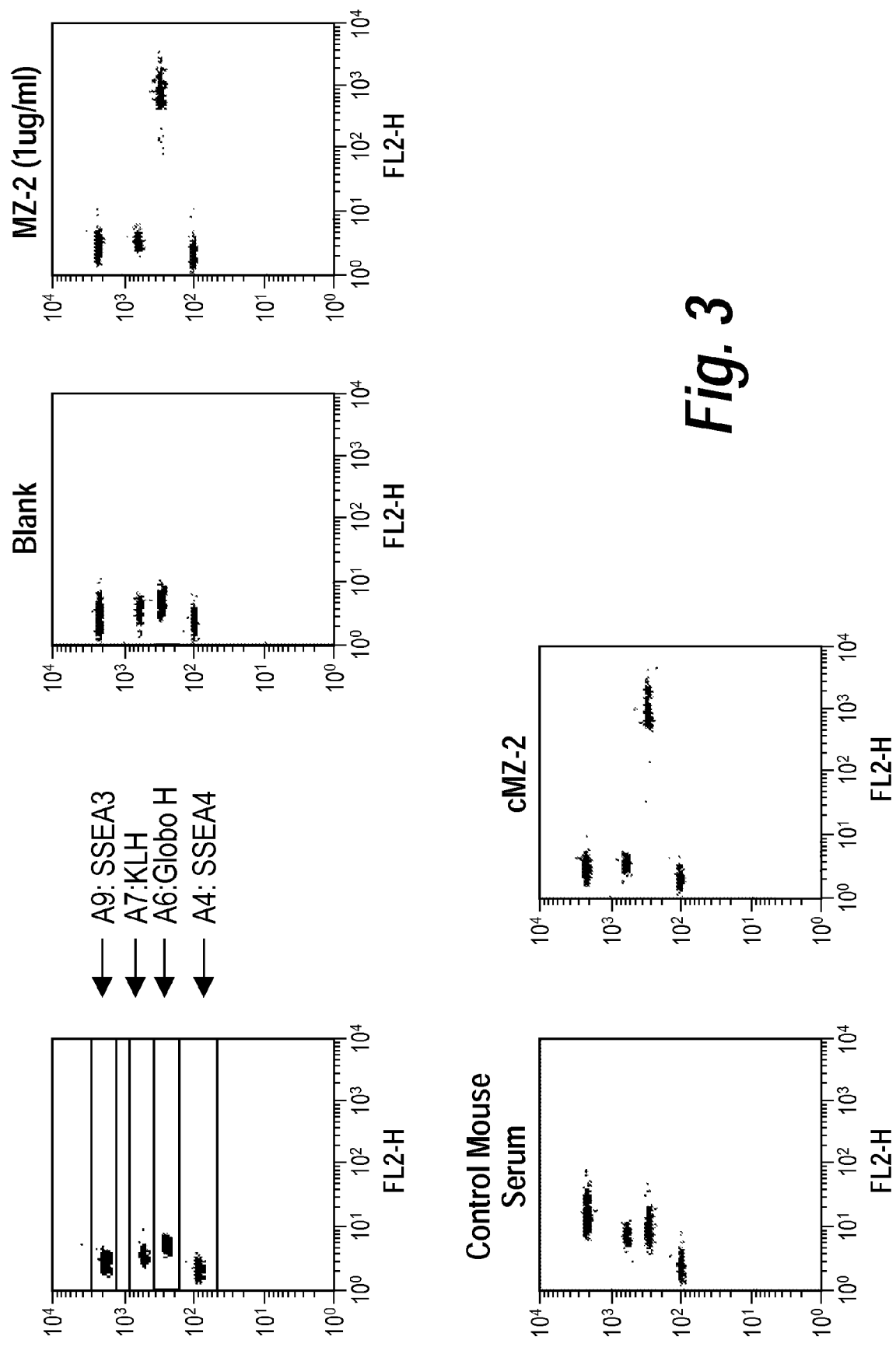
FIG. 3 is a FACS graph illustrating the result of a serial glycan-bead binding analysis, according to one working example of the present disclosure.

For detecting the specificity and relative titer of anti-Globo H antibody, each set of carbohydrate-conjugated beads were mixed and diluted to 1:50 of each. 50 µL of bead mixture was then transfer to V bottom 96-well plate, and mixed with 50 µL of 1:1000 diluted serum or 1 µg/mL of MZ-2 antibody. After incubation for 30 min, the beads were washed with 150 µL of wash buffer and further stained with 100 µL of PE-conjugated 2Ab (Jackson Immunoresearch). The binding of anti-Globo H antibody were detected by FACS. FIG. 3 show the specificity of MZ-2 antibody is indicated by the fact that MZ-2 and chimeric MZ-2 antibodies only bind to Globo H-conjugated beads, but not SSEA3- or SSEA4-conjugated beads.

Figure 4:
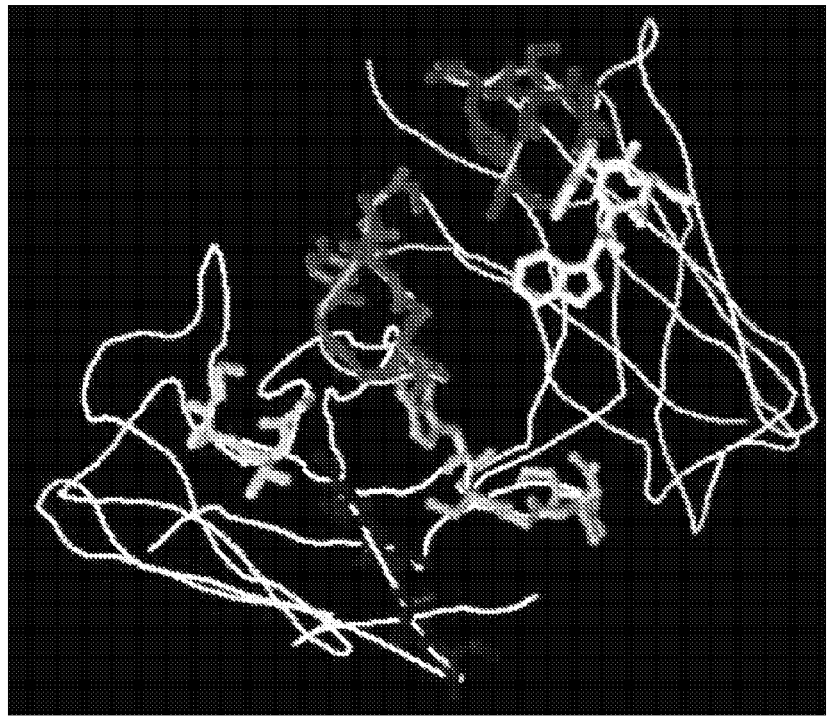
FIGS. 4A and B shows the simulation of protein folding of anti-Globo H IgG antibody, according to one working example of the present disclosure (A: Mouse MZ-2 monoclonal antibody; B: Humanized MZ-2 monoclonal antibody).
Figure 4:
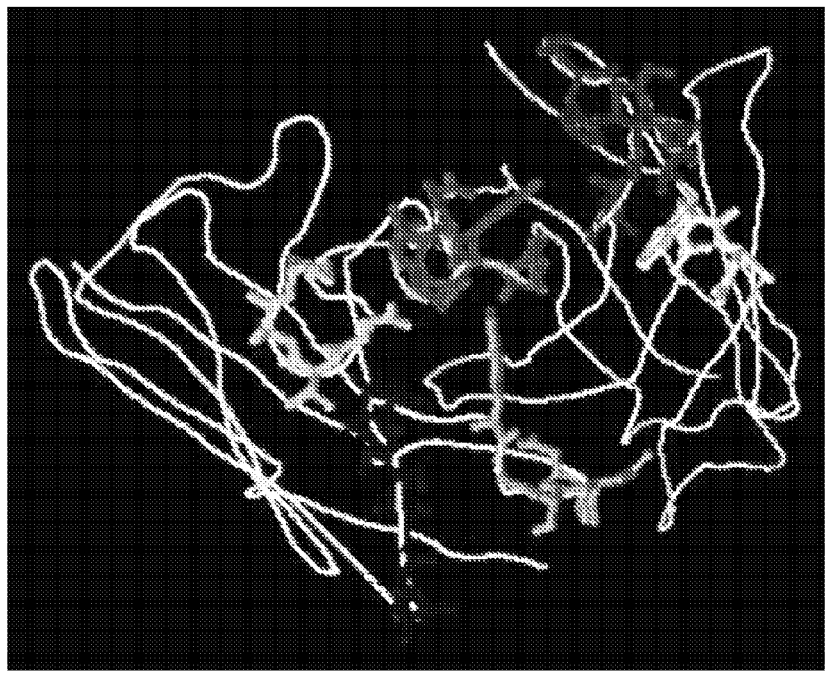

Example 4 Simulation of Protein Folding in Mouse and Humanized MZ-2 Monoclonal Antibody The 3-D structure of variable regions in original and humanized MZ-2 clones were simulated by Prediction of Immunoglobulin Structure online program. FIGS. 4A and B show the simulation of protein folding of mouse MZ-2 monoclonal antibody (FIG. 4A) and humanized MZ-2 monoclonal antibodies (FIG. 4B).

Figure 5:
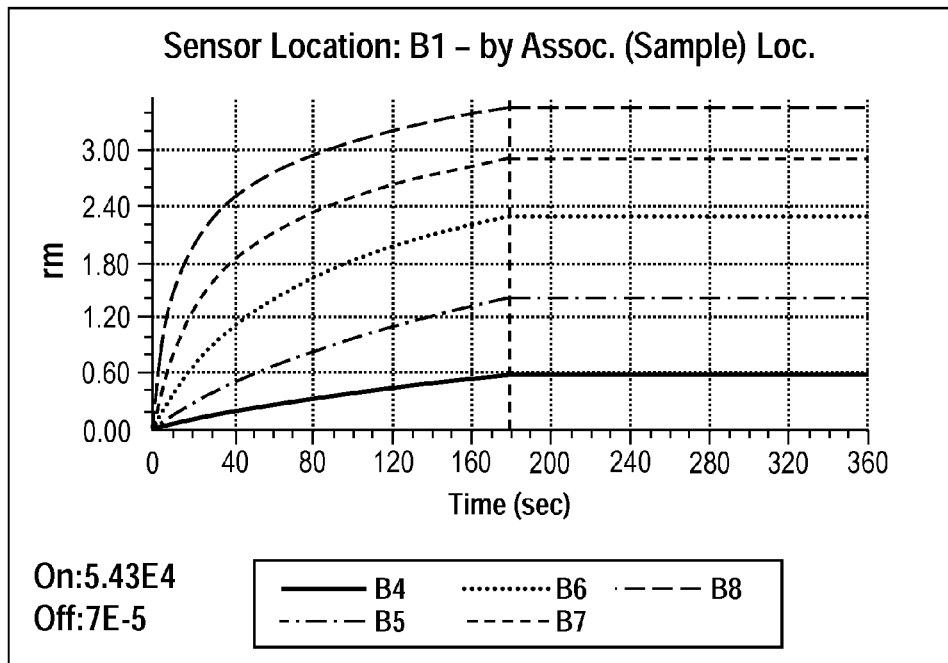
FIGS. 5A to E show the binding affinity of anti-Globo H IgG antibody, representing the association and Dissociation curve fitting and dissociation constant, according to one working example of the present disclosure (A: mMZ-2; B: cMZ-2; C:hMZ-2L; D: MK-1; E: hMZ-2Lw).
Figure 5:
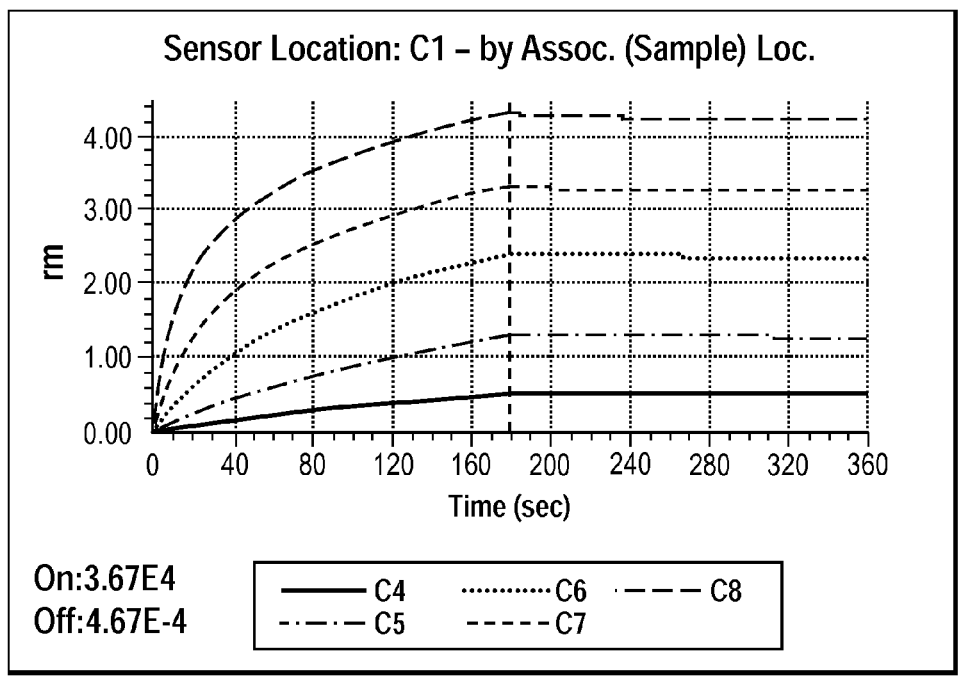
Figure 5:
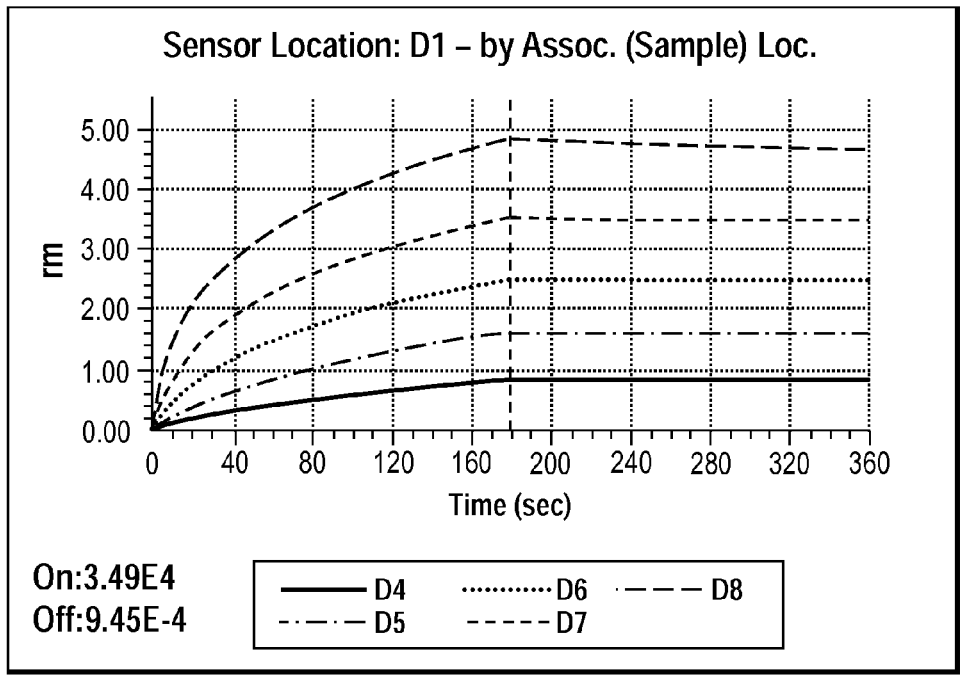
Figure 5:
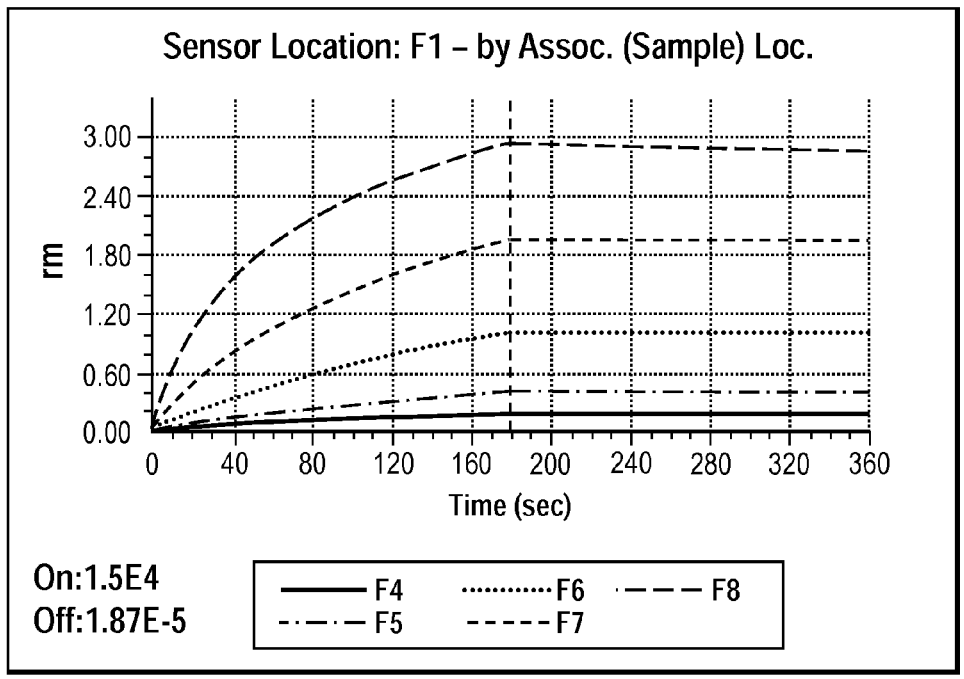
Figure 5:
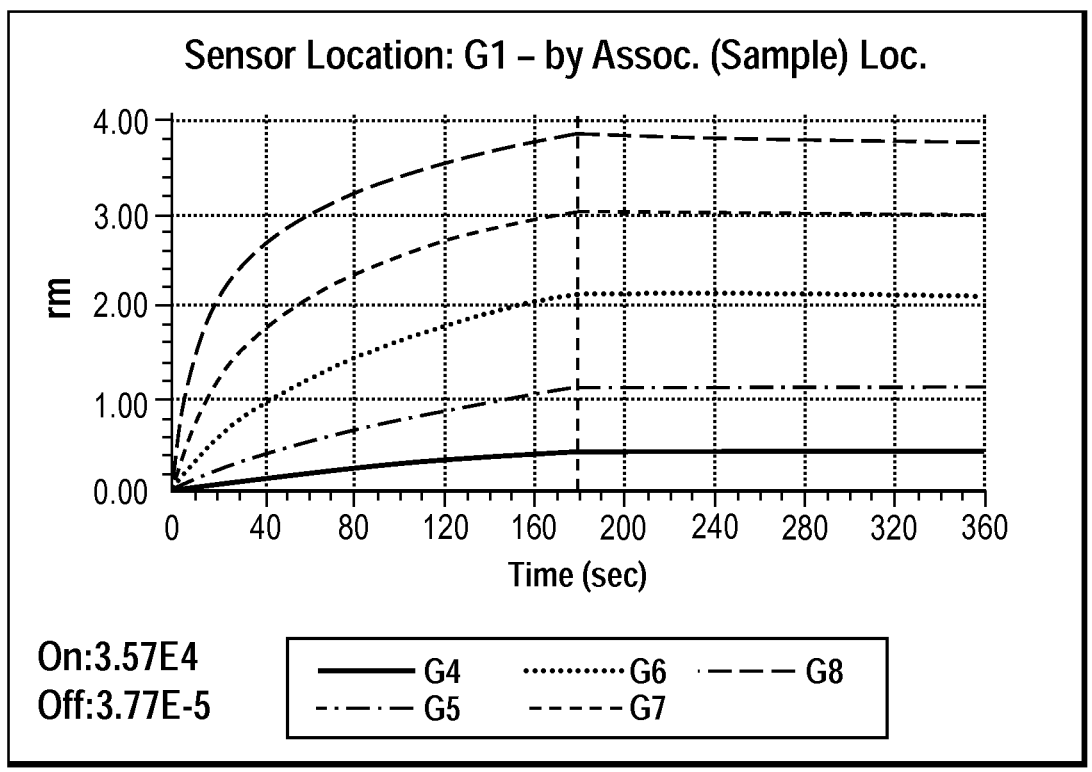

Example 5 Association and Dissociation Curve Fitting and KD Calculation of Antibodies of the Invention The binding affinity of anti-Globo H antibody was detected by Biolayer interferometry using FortrBio OcTet system. Briefly, the sensors were first soaked in 20 µM of biotinylated Globo H to coat Globo H on their surface. The MZ-2 clone (mMZ-2), mouse-human chimerical MZ-2 clone (cMZ-2), and humanized MZ-2 clones (hMZ-2L, MK-1 or hMZ-2Lw) were serially diluted into 1333, 444.4, 148.1, 49.4 and 16.5 nM, and incubated with Globo H coated sensors separately. 10 mM of Glycine (pH 1.5) was used as Regeneration buffer. FIGS. 5A and B show biacore full binding kinetic analysis of MZ-2 antibodies were carried out. Detailed binding kinetic parameters (association rate, ka, dissociation rate, kd, and affinity constant, KD) were determined by full kinetic analysis. Sensograms for each antibody are shown. The KD values of three humanized MZ-2 antibodies (hMZ-2L (see FIG. 5C), MK-1 (see FIG. 5D) and hMZ-2Lw (see FIG. 5E)) and chimeric MZ-2 (cMZ-2) antibody (see FIG. 5B) are similar.

Example 6 CDC Assay of Chimeric MZ-2 (IgG1 Kappa) on Breast MCF-7 Cells

MCF-7, TOV21G Globo H(+), and HPAC cells were adjusted to 2×106 cells/mL in RPMI 1640 medium and aliquot 50 µL of diluted cells into flow tubes. The chimeric MZ-2 antibody was diluted to 2× designed concentration in RPMI 1640 medium and aliquot 50 µL to each flow tube with cancer cells. Human IgG (Fitzgerald, 31-AI06) was diluted into the same concentration as a control. After 15 min, 100 µL of normal human serum from healthy human donor was added into each tube and incubated at 37° C. for 2 hr. The cells were washed once with complete medium and resuspended in 200 µL of complete medium with 0.5 µg/mL propidium iodide. The percentage of dead cells was analyzed using FACS.

Figure 6:
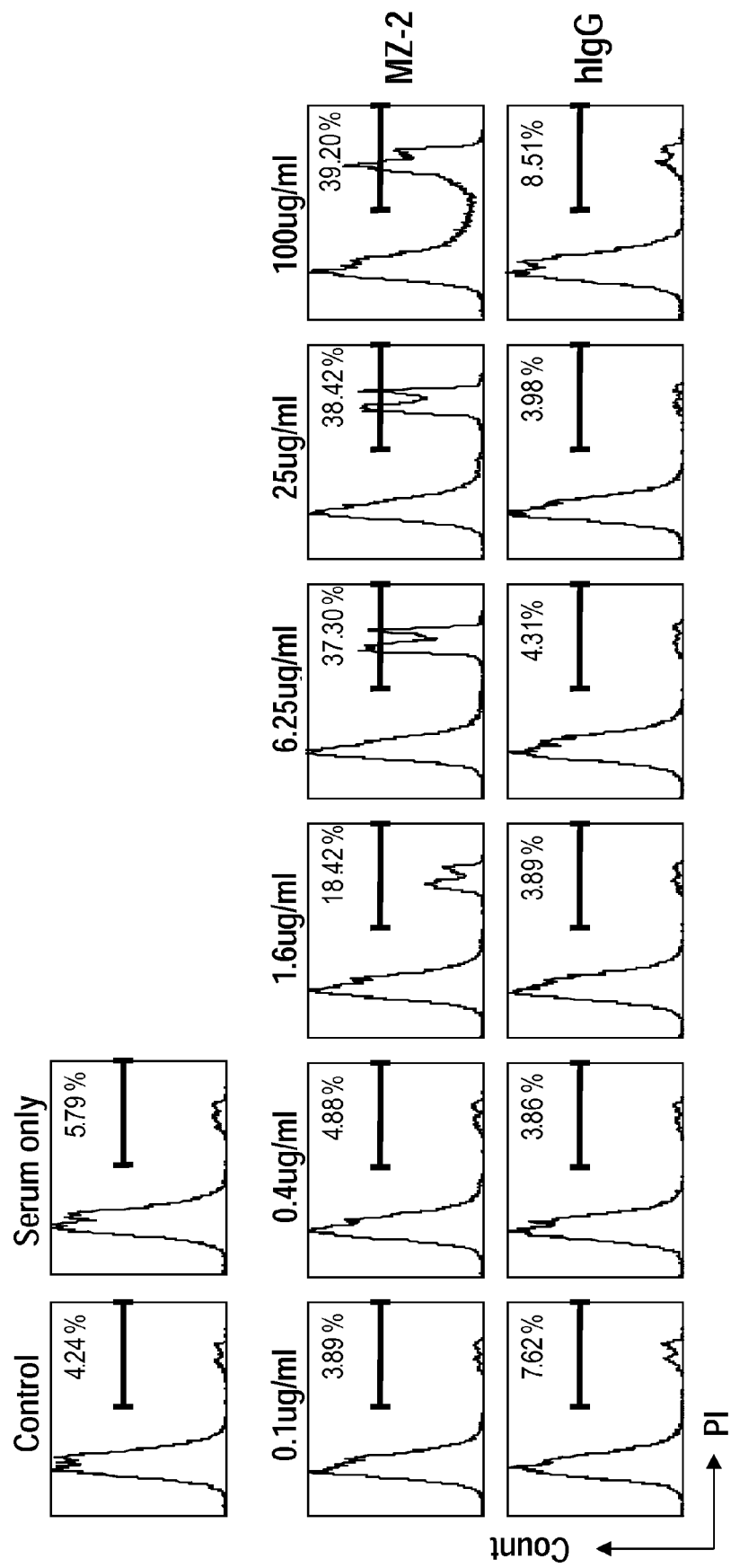
FIG. 6 shows that the human serum containing more than 1.6 μg/ml of hMZ-2Lw antibody elicited complement-dependent cytotoxicity in breast cancer, MCF-7 cells.
Figure 7:
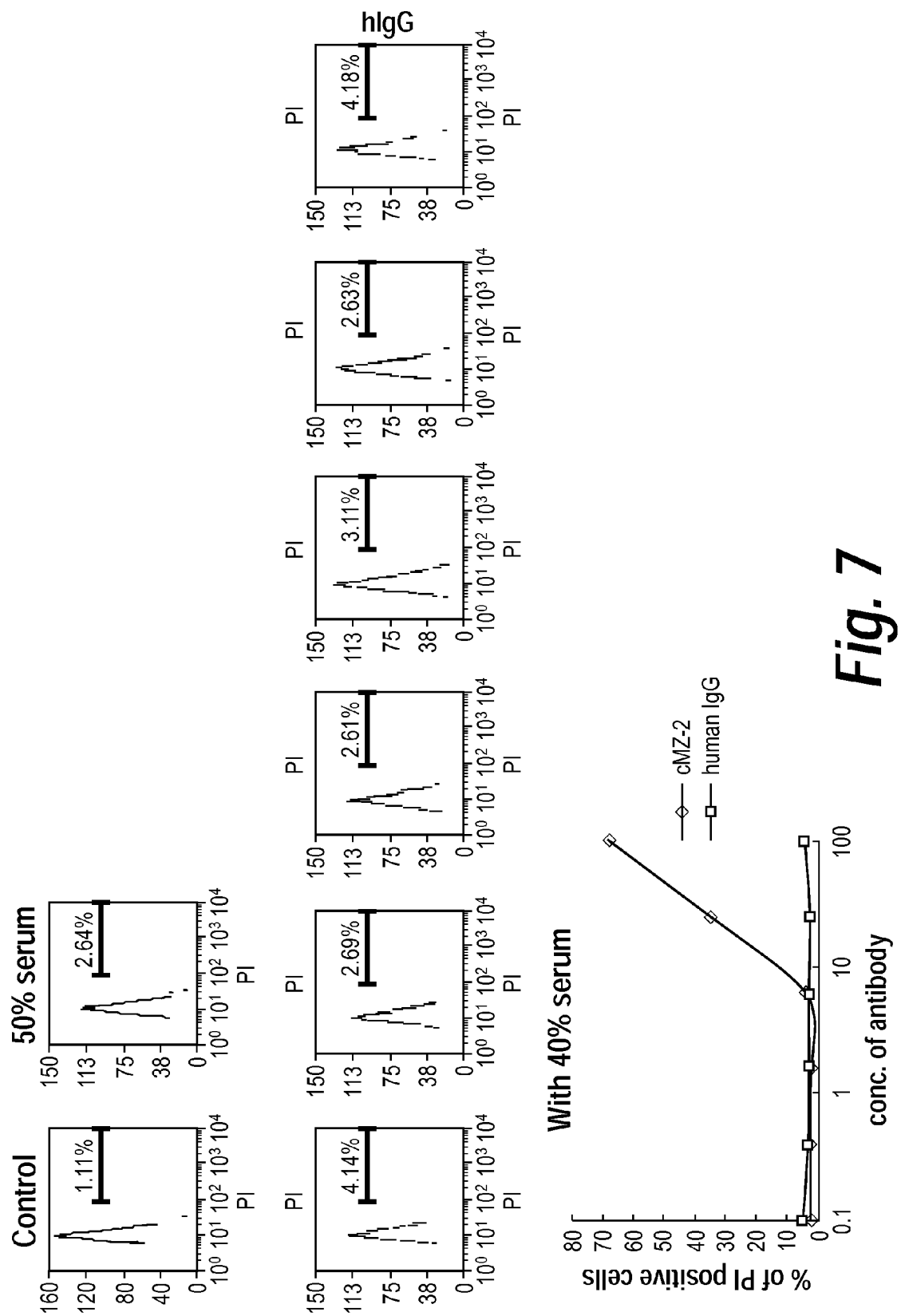
FIG. 7 shows that hMZ-2Lw antibody in a concentration higher than about 10 and 20 μg/ml resulted in a dose-dependent cytotoxicity in human ovarian cancer cell line TOV21G.
Figure 8:
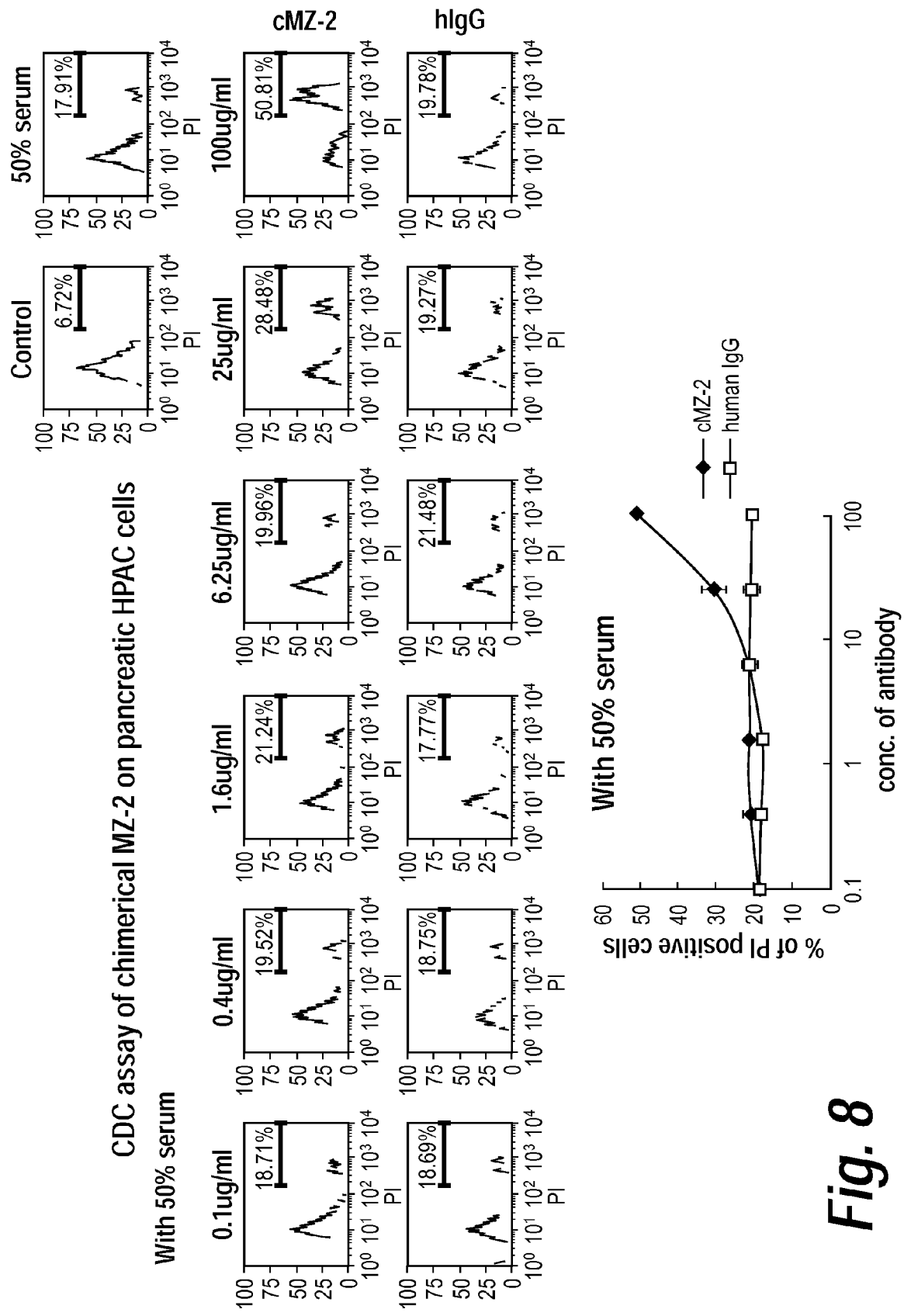
FIG. 8 shows that hMZ-2Lw antibody in a concentration higher than about 10 and 20 μg/ml resulted in a dose-dependent cytotoxicity in human pancreatic cancer cell line, HPAC.

Results of complement-dependent cytotoxicity (CDC) assay, as reported in FIG. 6, indicate that the human serum containing more than 1.6 µg/ml of hMZ-2Lw antibody elicited complement-dependent cytotoxicity in breast cancer, MCF-7 cells. The CDC increased in a dose-dependent manner. Similar trends were also observed in ovarian and pancreatic cancer cells in which hMZ-2Lw antibody in a concentration higher than about 10 and 20 µg/ml resulted in a dose-dependent cytotoxicity in human ovarian cancer cell line TOV21G (FIG. 7), or the pancreatic cancer cell line, HPAC (see FIG. 8).

Example 7 ADCC Assay of hMZ-2Lw and MK1 Antibody on MCF-7 Cells

Briefly, $7.5 \times 10^3$ (100 uL) of each cells were pre-seeded into the designed wells of 96-well assay plate (Corning Cat. #3917) and incubated overnight in a CO2 incubator at 37° C. The humanized anti-Globo H antibody clone hMZ-2Lw or MK1 was diluted into 3× highest concentration of assay and 4× serial dilution by 8 times. Noraml human IgG in the same concentration was used as control. ADCC assay was performed by ADCC Reporter Bioassay kit (Promega Cat. #G7010) at a E/T ratio of 10:1 and detected by chemoluminescent reader (EnSpire 2300, PerkinElmer). The folds of induced ADCC response were calculated as equation below:

Calculate Fold of Induction=RLU (induced-background)/RLU (no antibody control-background)

Figure 9:
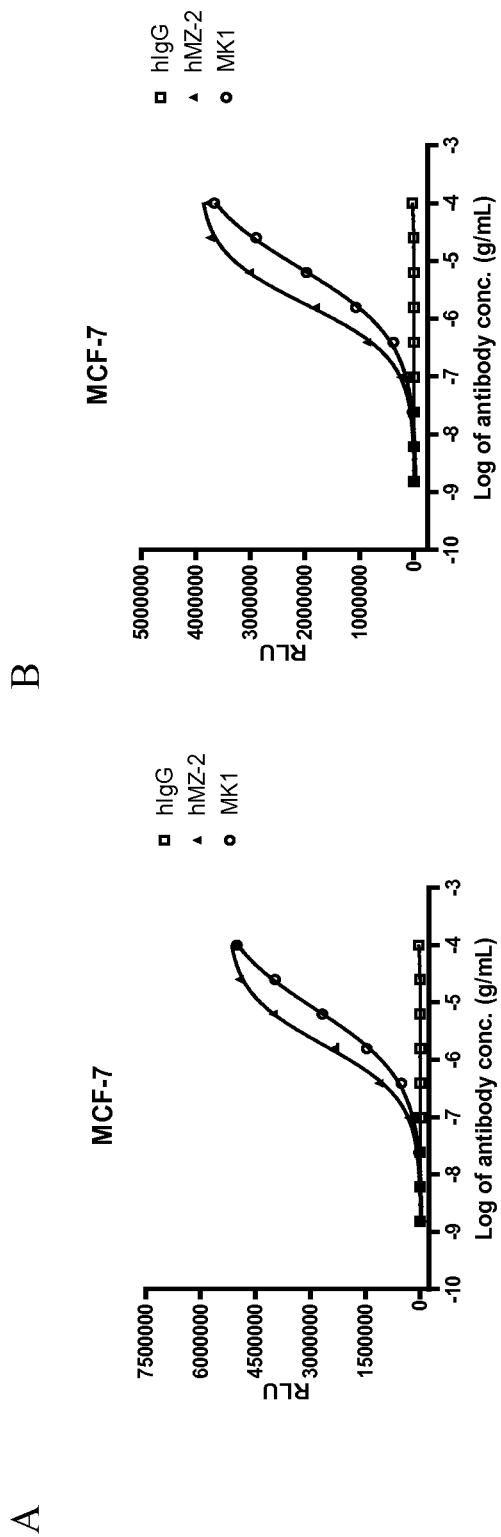
FIGS. 9A and B show antigen-dependent cell-mediated cytotoxicity (ADCC) activity of the present hMZ-2Lw and MK1 antibodies on MCF-7 cells (breast cancer cell line).
Figure 10:
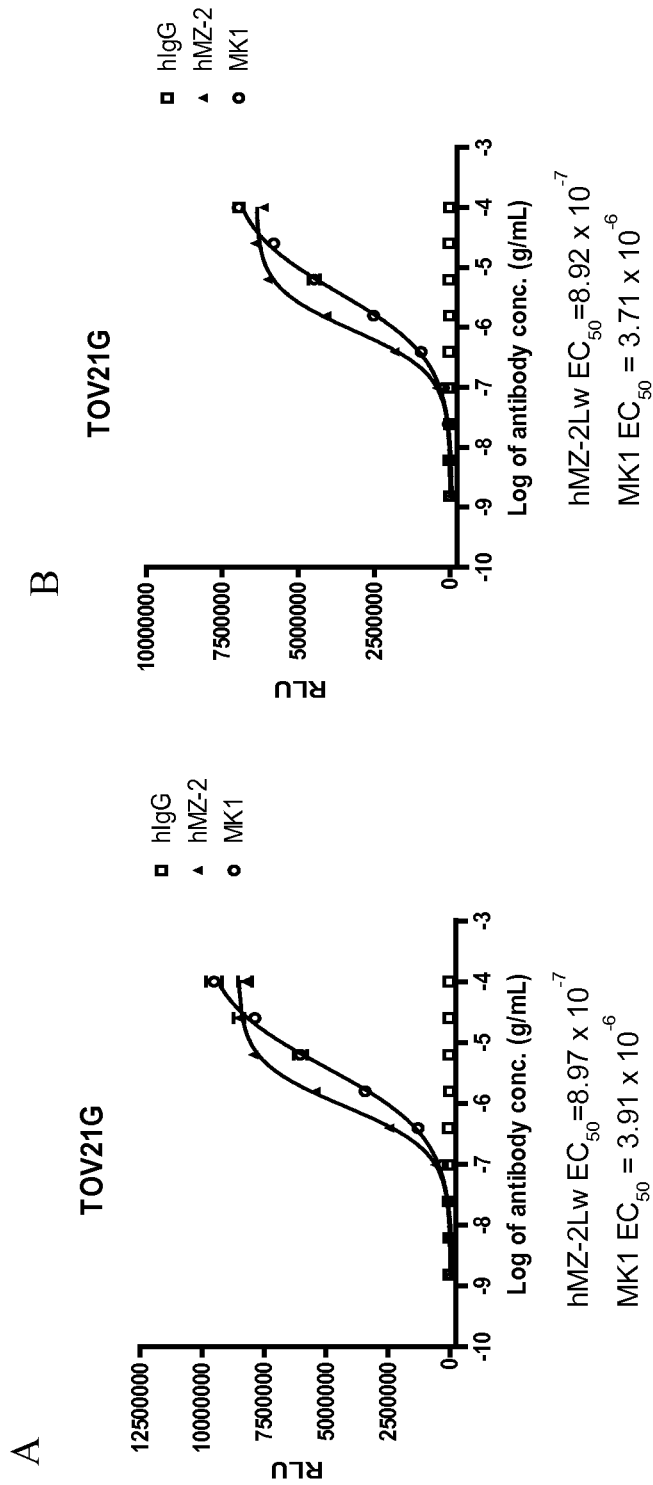
FIGS. 10A and B show antigen-dependent cell-mediated cytotoxicity (ADCC) activity of the present hMZ-2Lw and MK1 antibodies on TOV21G cells (ovarian cancer cell line).

FIGS. 9A and B and FIGS. 10A and B respectively summarizes the antigen-dependent cell-mediated cytotoxicity (ADCC) activity of the present hMZ-2Lw and MK1 antibodies on MCF-7 cells (breast cancer cell line) and TOV21G cells (ovarian cancer cell line). In general, these results demonstrate that the present humanized MZ-2 antibody may elicit efficient and dose-dependent ADCC in MCF-7 and TOV21G cells.

Example 8 Anti-Tumor Effect of Humanized MZ-2 Antibody, hMZ-2Lw and MK1

Figure 11:
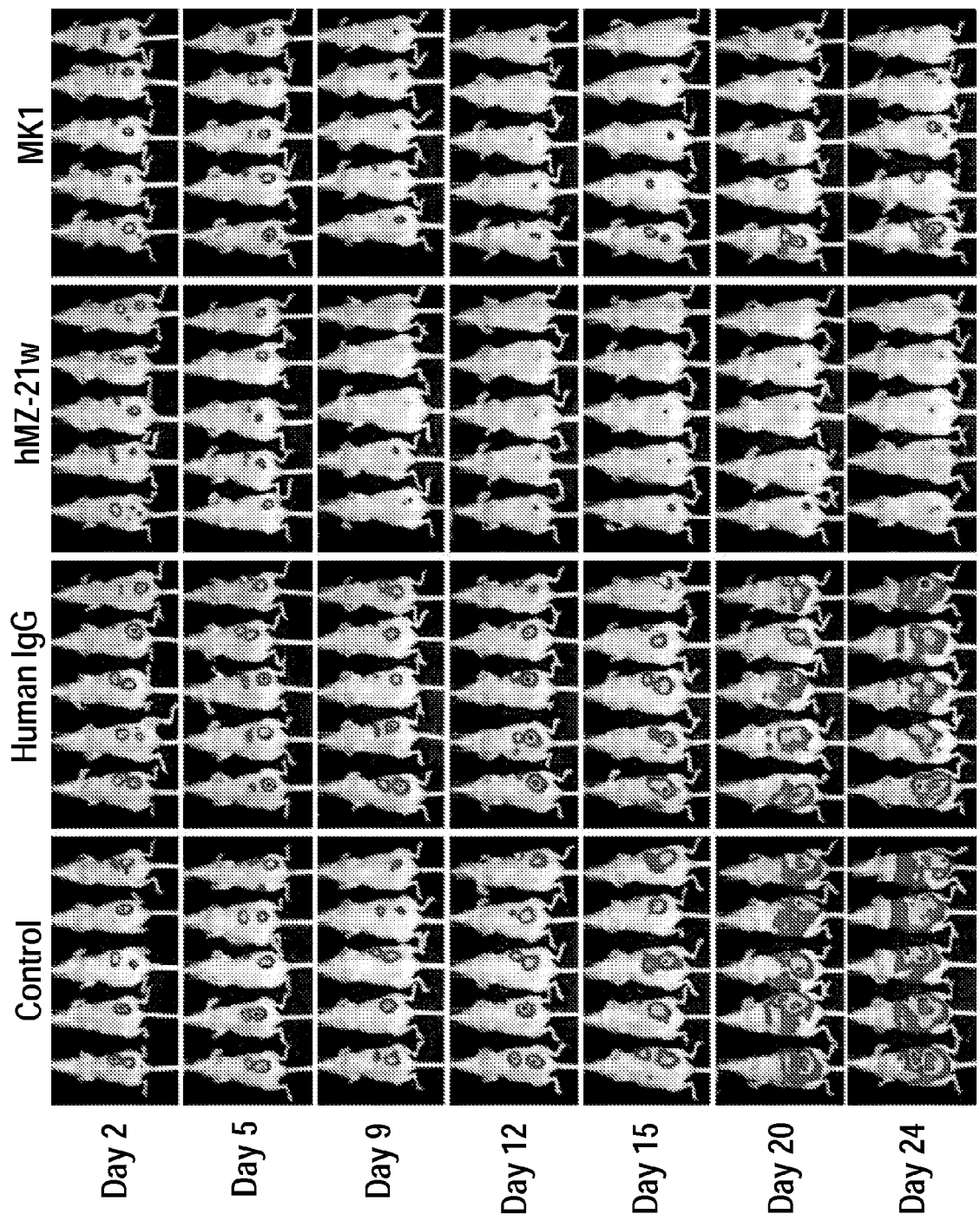
FIG. 11 shows administration of both hMZ-2Lw and MK1 antibodies significantly inhibit the tumor growth, while control IgG antibody did not substantially affect the tumor growth.

For establishing an intra-peritoneal ovarian tumor model, $1 \times 10^6$ of TOV21G cells were intraperitoneally (i.p.) injected into 5-week-old female NU/NU mice (BioLASCO Taiwan). Two days later, mice were divided into 4 groups and administered with either 100 µg (at a therapeutic dose of 5 mg/kg) of Human IgG, anti-GloboH antibodies hMZ-2Lw or MK1 twice a week through tail vein (i.v.) route. Untreated mice were set as control. To monitor the tumor growth, tumor bearing mice were i.p. injected 200 µL of luciferin (3.9 mg/ml) and the chemoluminance intensity of each mouse was detected by a non-invasive IVIS system (Xenogen) with fixed exposure condition in each different batch of experiment. Representative photograph in FIG. 11 illustrates administration of both hMZ-2Lw and MK1 antibodies significantly inhibit the tumor growth, while control IgG antibody did not substantially affect the tumor growth. However, the present hMZ-2 antibody significantly reduced the tumor size. By 24 days after treatment, tumor was nearly eliminated in mice given hMZ-2Lw antibody.

Figure 12:
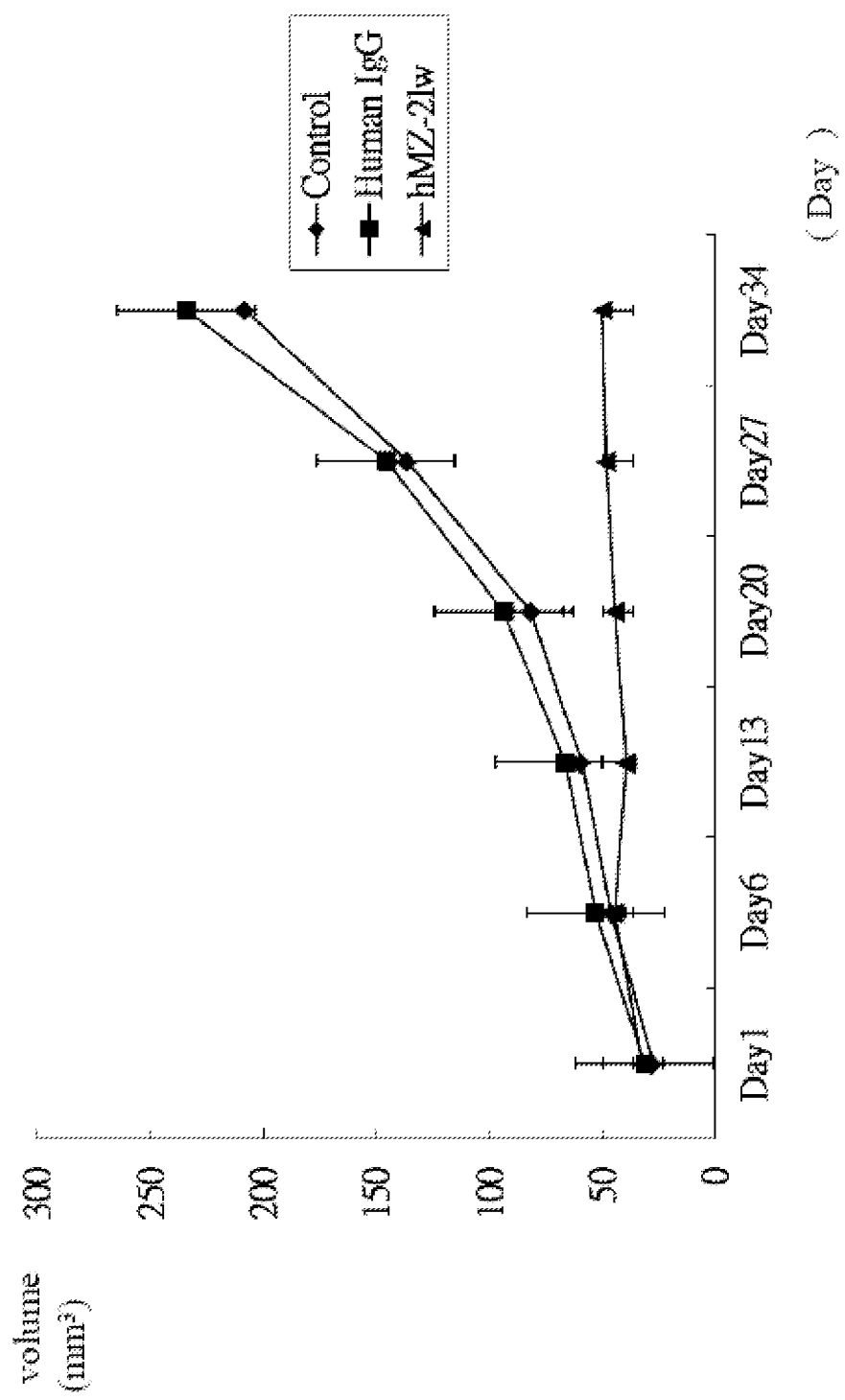
FIG. 12 shows results of hMZ-2 antibody in breast cancer subcutaneous model MCF-7 cell.
Figure 13:
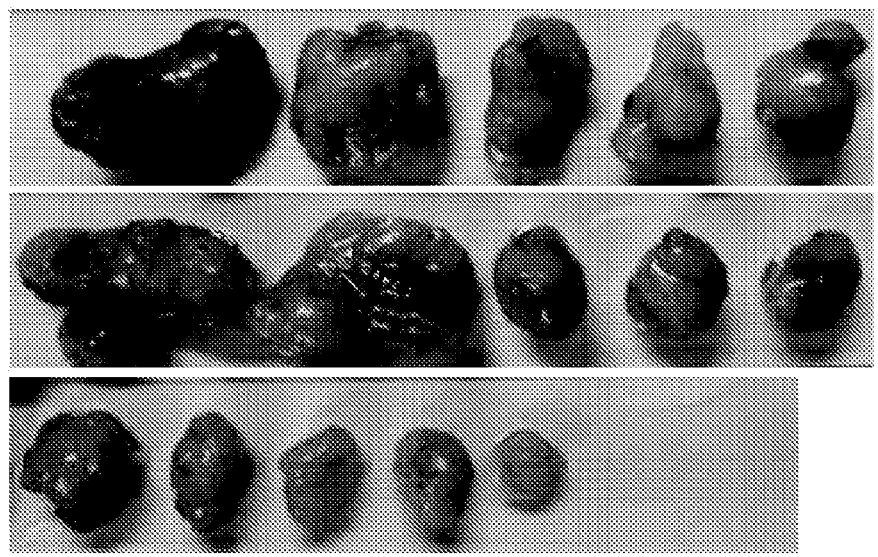
FIGS. 13A and B shows the results of hMZ-2 antibody in pancreatic cancer subcutaneous model HPAC cell. (A: Photographs of tumors; B: Reduction of tumor size)
Figure 13:
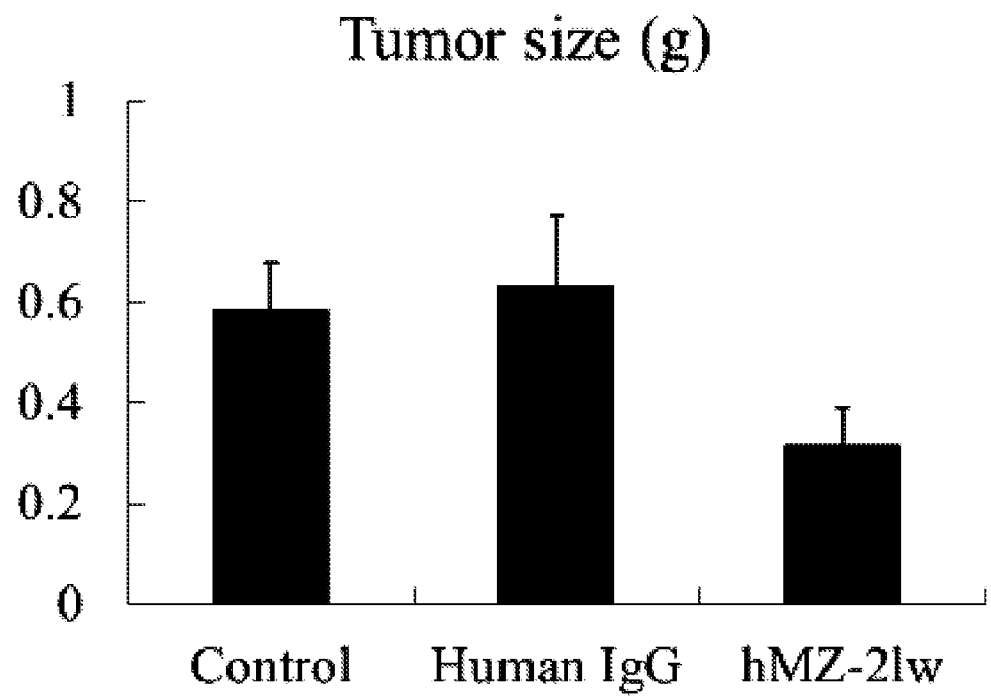

For establishing a subcutaneous breast tumor model, 17b-estradiol (Innovative Research of America, SE-121) was first subcutaneously (s.c.) implanted into NU/NU mice (BioLASCO Taiwan). Three days later, $3 \times 10^6$ MCF-7 cells mixed with matrigel were s.c. implanted (xenograft) into mice. Eighteen days after tumor challenge, mice were divided into 3 groups (n=7), and treated by a therapeutic dose (5 mg/kg) of human IgG (100 µg/mouse) or 100 µg/mouse of hMZ-2Lw antibody i.v. (through tail vein) twice a week. Mice without treatment were set as control. Tumor size was measured weekly by calipers. The results of hMZ-2 antibody in breast cancer subcutaneous model MCF-7 cell are shown in FIG. 12. FIGS. 13A and B shows the results of hMZ-2 antibody in pancreatic cancer subcutaneous model HPAC cell.

Example 9 MZ-2 Antibody Inhibits Migration of Globo H-Expressing TOV21G Cells (I)

Figure 14:
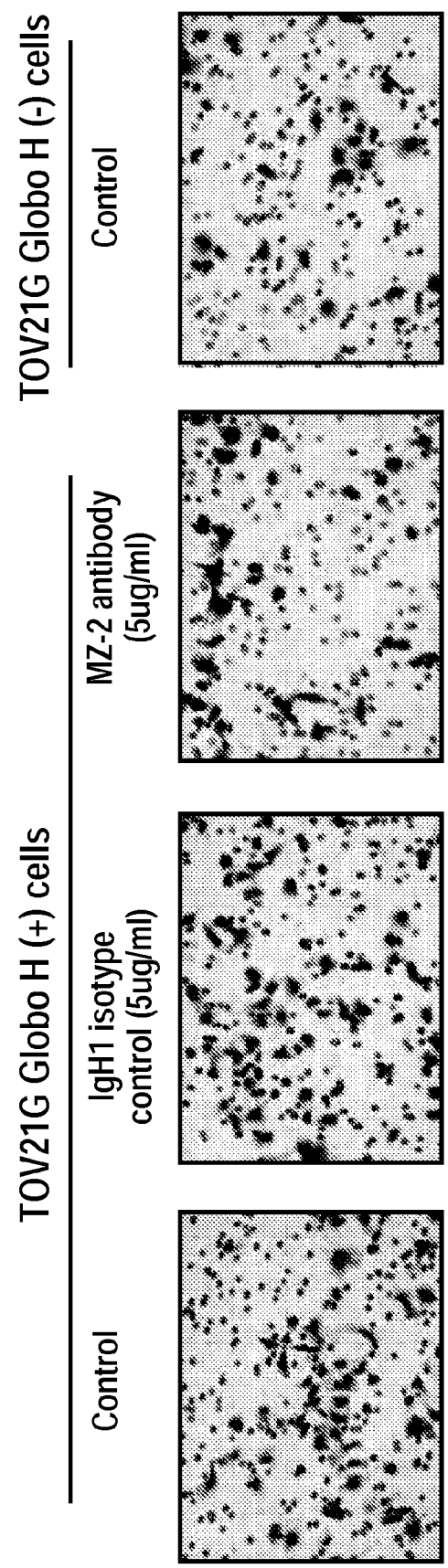
FIG. 14 shows that MZ-2 antibody inhibits migration of Globo H-expressing TOV21G cells.

Briefly, $2 \times 10^5$ of Globo H-positive TOV21G cells were mixed with 5 µg of mouse IgG1 isotype or MZ-2 antibody (hMZ-2Lw) in 1 mL of culture medium in and incubated at 37° C. for 15 min. These cells were then washed three times with 1×PBS and resuspended to $2 \times 10^5$ cells/mL in culture medium. One hundred micro liters of cells were transferred into the inserts of transwell (Corning) and incubated in $CO_2$ incubator for 24 hr. Cells without antibody treatment, or Globo H-negative TOV21G cells were used as controls. Those cells on the top side of transwell membrane were removed by cotton rod. Migrated cells through the membrane (bottom side) were fixed with 4% formaldehyde and stained with crystal violet. The numbers of migrated cells were counted by tissue scanner (TissueGnostics). FIG. 14 shows that MZ-2 antibody inhibits migration of Globo H-expressing TOV21G cells.

Example 10 MZ-2 Antibody Inhibits Migration of Globo H-Expressing TOV21G Cells (II)

Figure 15:
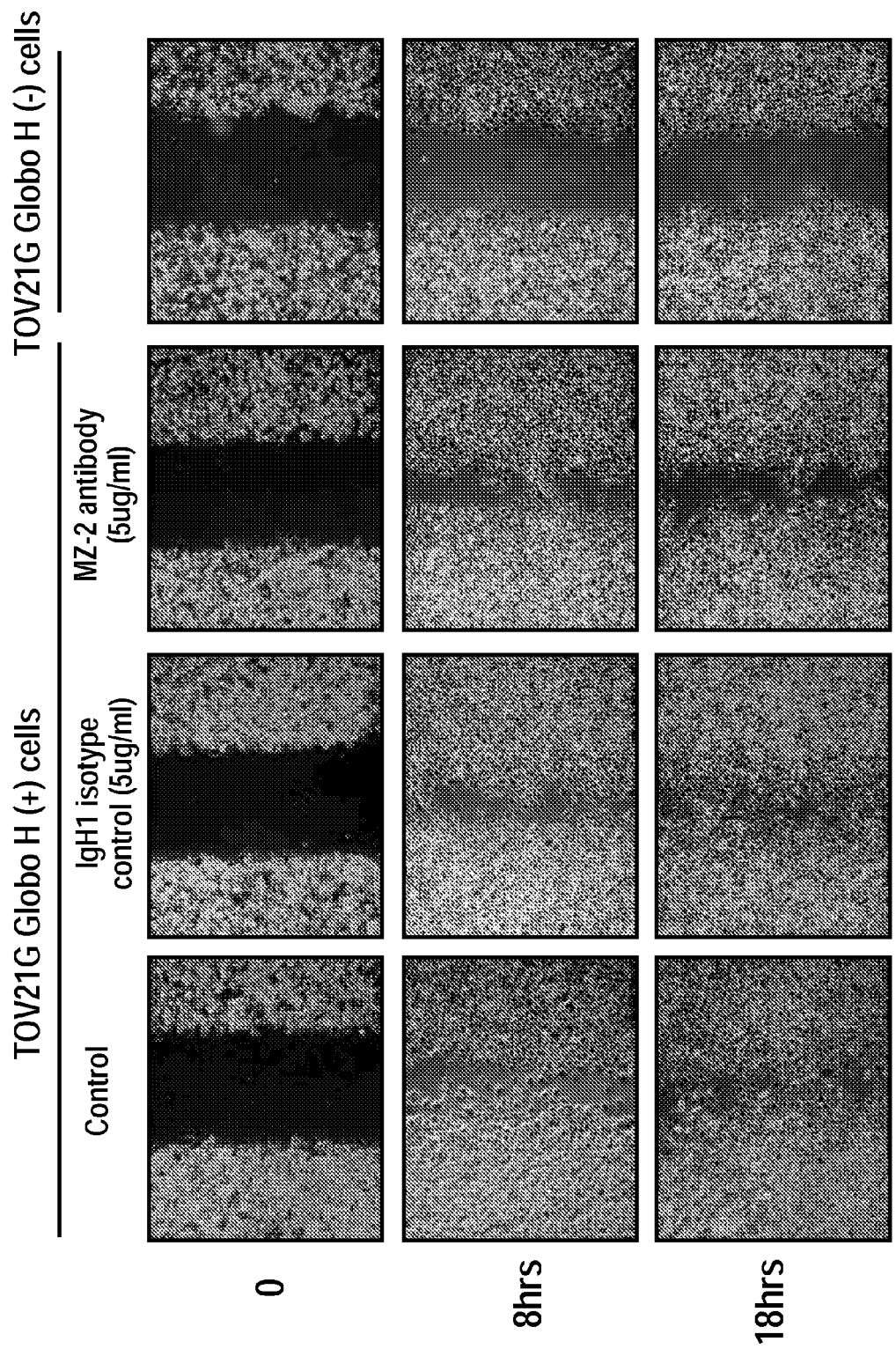
FIG. 15 shows that MZ-2 antibody inhibits migration of Globo H-expressing TOV21G cells.

Briefly, $2 \times 10^5$ of Globo H-expressing TOV21G cells were mixed with 5 µg of mouse IgG1 isotype (eBioscience) or MZ-2 antibody (hMZ-2Lw) in 0.5 mL of culture medium and incubated at 37° C. for 15 min. Those cells were then washed three times with 1× PBS, and resuspended to 4×10⁵ cells/mL in culture medium. One hundred micro liters of cells were transferred into a well of wound healing culture-inserts (Ibid Cat #80241) in a 24-well plate and incubated for 8 hours in $CO_2$ incubator. Cells without antibody treatment, or Globo H-negative TOV21G cells were used as controls. The insert were then removed and the cells were kept cultured for another 18 hours. Cell images were took by CCD camera from 0 hr to 18 hr after insert removal. Note that the gap of cells treated by MZ-2 antibody is larger than that treated by IgG1 isotype control. FIG. 15 shows that MZ-2 antibody inhibits migration of Globo H-expressing TOV21G cells.

Example 11 Assays of Other Antibodies of the Invention

The antibodies of the invention having the heavy chain variable regions and the light chain variable regions as described herein were subjected to the binding affinity assay of Example 2, association and dissociation assay of Example 5, CDC assay of Example 6, ADCC assay of Example 7 and anti-tumor assay of Example 8 and show similar results to cMZ-2 antibody, hMZ-2Lw antibody and MK-1 antibody. For example, the KD value of the antibody having a heavy chain variable region of SEQ ID NO: 27, and a light chain variable region of SEQ ID NO: 231 is in the range of $1 \times 10^{-7}$ to $1 \times 10^{-10}$ nM.

What is claimed is:

1. A method of treating a cancer, comprising administering to a subject in need thereof a therapeutically effective amount of an anti-Globo H antibody or antigen-binding portion thereof comprising:
   (a) H-CDR1 comprising an amino acid sequence selected from the group consisting of SEQ ID NO: 1, 2, 3, and 4;
   (b) H-CDR2 comprising an amino acid sequence selected from the group consisting of SEQ ID NO: 5, and 6;
   (c) H-CDR3 comprising an amino acid sequence selected from the group consisting of SEQ ID NO: 7, 8, and 9;
   (d) L-CDR1 comprising an amino acid sequence selected from the group consisting of SEQ ID NO: 10, 11, 12, and 13;
   (e) L-CDR2 comprising an amino acid sequence selected from the group consisting of SEQ ID NO: 14, 15, and 16; and
   (f) L-CDR3 comprising an amino acid sequence selected from the group consisting of SEQ ID NO: 17, 18, and 19.

2. The method of claim 1, wherein the cancer is a tumor-associated carbohydrate-expressing cancer.

3. The method of claim 2, wherein the cancer is ovarian cancer, breast cancer, pancreatic cancer, prostate cancer, colorectal cancer, or lung cancer.

4. The method of claim 1, wherein the cancer is a migration cancer.

5. The method of claim 1, further comprising administration of one or more additional treatments selected from angiogenic inhibitor treatment, chemotherapy, radiation, and surgery.

6. The method of claim 1, wherein the antibody or antigen-binding portion thereof is a monoclonal antibody, a chimeric antibody, or a humanized antibody.

7. The method of claim 1, wherein H-CDR1 comprises SEQ ID NO: 3; H-CDR2 comprises SEQ ID NO: 5; H-CDR3 comprises SEQ ID NO: 8; L-CDR1 comprises SEQ ID NO:12; L-CDR2 comprises SEQ ID NO:16; and L-CDR3 comprises SEQ ID NO: 18.

8. The method of claim 1, wherein the antibody or antigen-binding portion thereof comprises: (i) a heavy chain variable region comprising an amino acid sequence at least 85% identical to an amino acid sequence selected from SEQ ID NO: 140-163; and (ii) a light chain variable region comprising an amino acid sequence at least 80% identical to an amino acid sequence selected from SEQ ID NO: 164-199.

9. The method of claim 1, wherein the antibody or antigen-binding portion thereof comprises: (i) a heavy chain variable region comprising an amino acid sequence having at least 85% identical to the amino acid sequences of SEQ ID NO: 147, and (ii) a light chain variable region comprising an amino acid sequence having at least 80% identical to the amino acid sequence of SEQ ID NO: 195.

10. The method of claim 1, wherein the antibody or antigen-binding portion thereof comprises (i) a heavy chain variable region comprising an amino acid sequence consisting of SEQ ID NO: 147; and (ii) a light chain variable region comprising an amino acid sequence consisting of SEQ ID NO: 195.

11. The method of claim 1, wherein the antibody or antigen-binding portion thereof comprises (i) a heavy chain variable region comprising an amino acid sequence at least 85% identical to an amino acid sequence selected from SEQ ID NO: 20-43; and (ii) a light chain variable region comprising an amino acid sequence at least 80% identical to an amino acid sequence selected from SEQ ID NO: 44-79, and 200-235.

12. The method of claim 1, wherein the antibody or antigen-binding portion thereof comprises (i) a heavy chain variable region comprising an amino acid sequence selected from SEQ ID NO: 20-43; and (ii) a light chain variable region comprising an amino acid sequence selected from SEQ ID NO: 44-79, and 200-235.

13. The method of claim 1, wherein the antibody or antigen-binding portion thereof comprises (i) a heavy chain variable region comprising an amino acid sequence consisting of SEQ ID NO: 27; and (ii) a light chain variable region comprising an amino acid sequence consisting of SEQ ID NO: 75.

14. The method of claim 1, wherein the antibody or antigen-binding portion thereof comprises (i) a heavy chain variable region comprising an amino acid sequence consisting of SEQ ID NO: 27; and (ii) a light chain variable region comprising an amino acid sequence consisting of SEQ ID NO: 231.

15. The method of claim 1, wherein the antibody or antigen-binding portion thereof comprises (i) a heavy chain variable region comprising an amino acid sequence at least 85% identical to an amino acid sequence selected from SEQ ID NOs: 80-103; and (ii) a light chain variable region comprising an amino acid sequence at least 85% identical to an amino acid sequence of SEQ ID NOs: 104-139.

16. The method of claim 1, wherein the antibody or antigen-binding portion thereof comprises (i) a heavy chain variable region comprising an amino acid sequence selected from SEQ ID NO: 80-103; and (ii) a light chain variable region comprising an amino acid sequence selected from SEQ ID NO: 104-139.

17. The method of claim 1, wherein the antibody or antigen-binding portion thereof comprises (i) a heavy chain variable region comprising an amino acid sequence consisting of SEQ ID NO: 90; and (ii) a light chain variable region comprising an amino acid sequence consisting of SEQ ID NO: 135.

18. The method of claim 1, wherein the antibody or antigen-binding portion thereof comprises: (i) a heavy chain variable region comprising an amino acid sequence at least 85% identical to an amino acid sequence selected from SEQ ID NO: 140-163, wherein the third from last amino acid of the amino acid sequence, "V," is changed to "I"; and (ii) a light chain variable region comprising an amino acid sequence at least 80% identical to an amino acid sequence selected from SEQ ID NO: 164-199.

19. The method of claim 1, wherein the antibody or antigen-binding portion thereof comprises: (i) a heavy chain variable region comprising an amino acid sequence having at least 85% identical to the amino acid sequences of SEQ ID NO: 147, wherein the third from last amino acid of the amino acid sequence, "V," is changed to "I"; and (ii) a light chain variable region comprising an amino acid sequence having at least 80% identical to the amino acid sequence of SEQ ID NO: 195.

20. The method of claim 1, wherein the antibody or antigen-binding portion thereof comprises (i) a heavy chain variable region comprising an amino acid sequence consisting of SEQ ID NO: 147, wherein the third from last amino acid of the amino acid sequence, "V," is changed to "I"; and (ii) a light chain variable region comprising an amino acid sequence consisting of SEQ ID NO: 195.

* * * * *

SEQUENCE LISTING

```
<160> NUMBER OF SEQ ID NOS: 242

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain complementarity determining region
      1 (H-CDR1)

<400> SEQUENCE: 1

Gly Phe Ser Leu Ser Thr Phe Asp Met Gly Val Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain complementarity determining region
      1 (H-CDR1)

<400> SEQUENCE: 2

Gly Ser Ser Leu Ser Thr Phe Asp Val Gly Val Gly
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain complementarity determining region
      1 (H-CDR1)

<400> SEQUENCE: 3

Gly Phe Ser Leu Gly Thr Phe Asp Leu Gly Ile Gly
1               5                   10

<210> SEQ ID NO 4
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: heavy chain complementarity determining region
      1 (H-CDR1)

<400> SEQUENCE: 4

Gly Phe Ser Leu Ser Thr Phe Asp Leu Gly Ile Gly
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2 (H-CDR2)

<400> SEQUENCE: 5

His Ile Trp Trp Asp Asp Asp Lys Tyr Tyr Asn Pro Ala
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2 (H-CDR2)

<400> SEQUENCE: 6

His Ile Trp Gly Asp Asp Asp Lys Tyr Tyr Asn Pro Ala
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3 (H-CDR3)

<400> SEQUENCE: 7

Leu Tyr Gly Asn Tyr Leu Thr Ser Phe Tyr Cys Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3 (H-CDR3)

<400> SEQUENCE: 8

Leu Ser Gly Asn Tyr Leu Thr Ser Phe Tyr Cys Asp Tyr
1               5                   10

<210> SEQ ID NO 9
<211> LENGTH: 13
<212> TYPE: PRT
```

<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: heavy chain CDR3 (H-CDR3)

<400> SEQUENCE: 9

Leu Tyr Gly Asn Tyr Leu Arg Ser Tyr Tyr Cys Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: light chain CDR1 (L-CDR1)

<400> SEQUENCE: 10

Ser Ala Ser Ser Ser Val Ser Tyr Met His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: light chain CDR1 (L-CDR1)

<400> SEQUENCE: 11

Ser Ala Ser Ser Arg Val Ser Tyr Met His
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: light chain CDR1 (L-CDR1)

<400> SEQUENCE: 12

Ser Ala Arg Ser Ser Val Ser Tyr Met His
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
     peptide
<220> FEATURE:
<223> OTHER INFORMATION: light chain CDR1 (L-CDR1)

<400> SEQUENCE: 13

Arg Ala Ser Ser Ser Val Ser Tyr Met His
1               5                   10

<210> SEQ ID NO 14
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2 (L-CDR2)

<400> SEQUENCE: 14

Ala Thr Ser Asn Leu Ala Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2 (L-CDR2)

<400> SEQUENCE: 15

Trp Thr Ser Asp Arg Tyr Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2 (L-CDR2)

<400> SEQUENCE: 16

Asp Thr Ser Lys Leu Ala Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3 (L-CDR3)

<400> SEQUENCE: 17

Gln Gln Trp Ser Ser Asn Pro Phe Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3 (L-CDR3)

<400> SEQUENCE: 18

Gln Gln Trp Ser Ser Asn Pro Leu Thr
1               5

<210> SEQ ID NO 19
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3 (L-CDR3)

<400> SEQUENCE: 19

Gln Gln His Leu His Ile Pro Tyr Thr
1               5

<210> SEQ ID NO 20
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 20

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 21

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80
```

```
Val Leu Thr Met Thr Asn Met Asp Pro Val Asp Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 22

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
                20                  25                  30

Asp Met Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120
```

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 23

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ser Ser Leu Ser Thr Phe
                20                  25                  30

Asp Val Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Ala Thr Tyr Tyr
                85                  90                  95

Cys Ala Arg Leu Tyr Gly Asn Tyr Leu Thr Ser Phe Tyr Cys Asp Tyr
            100                 105                 110
```

Trp Gly Gln Gly Thr Leu Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 24

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 25

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 26

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 27
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 27

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 28
<211> LENGTH: 123
<212> TYPE: PRT
<213> ORGANISM: Artificial Sequence
<220> FEATURE:

<223> OTHER INFORMATION: Description of Artificial Sequence: Synthetic
     polypeptide
<220> FEATURE:
<223> OTHER INFORMATION: Heavy chain variable region of hMZ-2 series

<400> SEQUENCE: 28

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 29
<211> LENGTH: 123
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Heavy chain variable region of hMZ-2 series

<400> SEQUENCE: 29

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: Heavy chain variable region of hMZ-2 series -continued

```
<400> SEQUENCE: 30

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 31
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 31

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 32
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 32

Gln Ile Thr Leu Lys Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
            115                 120
```

<210> SEQ ID NO 33
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Heavy chain variable region of hMZ-2 series

<400> SEQUENCE: 33

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
            115                 120
```

<210> SEQ ID NO 34
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Heavy chain variable region of hMZ-2 series

<400> SEQUENCE: 34

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45
```

```
Trp Leu Ala His Ile Trp Gly Asp Asp Lys Tyr Tyr Asn Pro Ala
        50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
            115                 120
```

<210> SEQ ID NO 35
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 35

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Ser Ser Leu Ser Thr Phe
                 20                  25                  30

Asp Val Gly Val Gly Trp Ile Arg Gln Pro Pro Gly Lys Ala Leu Glu
             35                  40                  45

Trp Leu Ala His Ile Trp Gly Asp Asp Lys Tyr Tyr Asn Pro Ala
        50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
            115                 120
```

<210> SEQ ID NO 36
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 36

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Ser Ser Leu Ser Thr Phe
                 20                  25                  30

Asp Val Gly Val Gly Trp Ile Arg Gln Pro Pro Gly Lys Ala Leu Glu
             35                  40                  45

Trp Leu Ala His Ile Trp Gly Asp Asp Lys Tyr Tyr Asn Pro Ala
        50                  55                  60

Leu Lys Ser Arg Leu Thr Ile Thr Lys Asp Thr Ser Lys Asn Gln Val
```

Val Leu Thr Met Thr Asn Met Asp Pro Val Asp Thr Ala Thr Tyr Tyr
            85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
            115                 120

<210> SEQ ID NO 37
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 37

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
            35                  40                  45

Trp Leu Ala His Ile Trp Gly Asp Asp Asp Lys Tyr Tyr Asn Pro Ala
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
            115                 120

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 38

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
            35                  40                  45

Trp Leu Ala His Ile Trp Gly Asp Asp Asp Lys Tyr Tyr Asn Pro Ala
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

```
Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 39

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 40
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 40

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120
```

```
<210> SEQ ID NO 41
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 41

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 42
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 42

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 43
<211> LENGTH: 123
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of hMZ-2 series

<400> SEQUENCE: 43

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
            115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 44

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 45
```

```
Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Asn Pro Leu Thr
                85                  90                  95

Phe Gly Gly Gly Thr Lys Leu Glu Ile Lys Arg
            100                 105
```

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 46

```
Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105
```

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 47

```
Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
                35                  40                  45

Ala Thr Ser Asn Leu Ala Ser Gly Val Pro Ser Arg Phe Ser Gly Ser
```

```
                    50                  55                  60
Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gly Gly Thr Lys Leu Glu Ile Lys Arg
            100                 105

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 48

Glu Ile Val Leu Thr Gln Ser Pro Ser Ser Leu Ser Ala Ser Val Gly
 1               5                  10                  15

Asp Arg Val Thr Ile Thr Cys Ser Ala Ser Ser Arg Val Ser Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
         50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Leu Thr
                 85                  90                  95

Phe Gly Gly Gly Thr Lys Leu Glu Ile Lys Arg
            100                 105

<210> SEQ ID NO 49
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 49

Glu Ile Val Leu Thr Gln Ser Pro Ser Ser Leu Ser Ala Ser Val Gly
 1               5                  10                  15

Asp Arg Val Thr Ile Thr Cys Ser Ala Ser Ser Arg Val Ser Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
         50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln His Leu His Ile Pro Tyr Thr
                 85                  90                  95

Phe Gly Gly Gly Thr Lys Leu Glu Ile Lys Arg
            100                 105
```

```
<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 50

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 51

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series
```

<400> SEQUENCE: 52

Glu Ile Val Leu Thr Gln Ser Pro Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 53

Glu Ile Val Leu Thr Gln Ser Pro Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 54

Glu Ile Val Leu Thr Gln Ser Pro Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

```
Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Leu Thr
                 85                  90                  95

Phe Gly Gly Gly Thr Lys Leu Glu Ile Lys Arg
                100                 105

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 55

Glu Ile Val Leu Thr Gln Ser Pro Ser Ser Leu Ser Ala Ser Val Gly
 1               5                  10                  15

Asp Arg Val Thr Ile Thr Cys Arg Ala Ser Ser Ser Val Ser Tyr Met
                 20                  25                  30

His Trp Tyr Gln Gln Lys Pro Gly Lys Ala Pro Lys Leu Leu Ile Tyr
             35                  40                  45

Ala Thr Ser Asn Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln His Leu His Ile Pro Tyr Thr
                 85                  90                  95

Phe Gly Gly Gly Thr Lys Leu Glu Ile Lys Arg
                100                 105

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 56

Glu Ile Val Leu Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
                 20                  25                  30

His Trp Tyr Gln Gln Lys Pro Gly Lys Ala Pro Lys Leu Leu Ile Tyr
             35                  40                  45

Trp Thr Ser Asp Arg Tyr Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gly Gly Thr Lys Leu Glu Ile Lys Arg
                100                 105
```

-continued

```
<210> SEQ ID NO 57
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 57

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 58

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series
```

-continued

<400> SEQUENCE: 59

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 60

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 61

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

```
Trp Thr Ser Asp Arg Tyr Ser Gly Val Pro Ser Arg Phe Ser Gly Ser
        50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln His Leu His Ile Pro Tyr Thr
                 85                  90                  95

Phe Gly Gly Gly Thr Lys Leu Glu Ile Lys Arg
            100                 105

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 62

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
                 20                  25                  30

His Trp Tyr Gln Gln Lys Pro Gly Lys Ala Pro Lys Leu Leu Ile Tyr
             35                  40                  45

Trp Thr Ser Asp Arg Tyr Ser Gly Val Pro Ser Arg Phe Ser Gly Ser
        50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gly Gly Thr Lys Leu Glu Ile Lys Arg
            100                 105

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 63

Glu Ile Val Leu Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
                 20                  25                  30

His Trp Tyr Gln Gln Lys Pro Gly Lys Ala Pro Lys Leu Leu Ile Tyr
             35                  40                  45

Trp Thr Ser Asp Arg Tyr Ser Gly Val Pro Ser Arg Phe Ser Gly Ser
        50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Leu Thr
                 85                  90                  95

Phe Gly Gly Gly Thr Lys Leu Glu Ile Lys Arg
```

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable region of hMZ-2 series

<400> SEQUENCE: 64

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 65
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable region of hMZ-2 series

<400> SEQUENCE: 65

Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:

<223> OTHER INFORMATION: Light chain variable region of hMZ-2 series

<400> SEQUENCE: 66

Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 67

Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 68

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr

```
                35                  40                  45

Asp Thr Ser Lys Leu Ala Ser Gly Val Pro Ser Arg Phe Ser Gly Ser
        50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 69

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 70
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 70

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95
```

```
Phe Gly Gly Gly Thr Lys Leu Glu Ile Lys Arg
            100                 105

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 71

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 72

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: Light chain variable region of hMZ-2 series

<400> SEQUENCE: 73

Glu Ile Val Leu Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 74

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 75
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 75

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

```
His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Leu Thr
                 85                  90                  95

Phe Gly Gly Gly Thr Lys Leu Glu Ile Lys Arg
                100                 105

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 76

Glu Ile Val Leu Thr Gln Ser Pro Ser Ser Leu Ser Ala Ser Val Gly
  1               5                  10                  15

Asp Arg Val Thr Ile Thr Cys Ser Ala Arg Ser Ser Val Ser Tyr Met
                 20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln His Leu His Ile Pro Tyr Thr
                 85                  90                  95

Phe Gly Gly Gly Thr Lys Leu Glu Ile Lys Arg
                100                 105

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 77

Glu Ile Val Leu Thr Gln Ser Pro Ser Ser Leu Ser Ala Ser Val Gly
  1               5                  10                  15

Asp Arg Val Thr Ile Thr Cys Arg Ala Ser Ser Val Ser Tyr Met
                 20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95
```

```
Phe Gly Gly Gly Thr Lys Leu Glu Ile Lys Arg
            100                 105
```

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 78

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105
```

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 79

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105
```

<210> SEQ ID NO 80
<211> LENGTH: 123
<212> TYPE: PRT
<213> ORGANISM: Artificial Sequence
<220> FEATURE:
<223> OTHER INFORMATION: Description of Artificial Sequence: Synthetic

```
polypeptide
<220> FEATURE:
<223> OTHER INFORMATION: Heavy chain variable region of MK1 series

<400> SEQUENCE: 80

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 81
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 81

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 82
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 82
```

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
                20                  25                  30

Asp Met Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
                100                 105                 110

Trp Gly Gln Gly Thr Leu Val Thr Val Ser Ser
            115                 120
```

<210> SEQ ID NO 83
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 83

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
                20                  25                  30

Asp Val Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
                100                 105                 110

Trp Gly Gln Gly Thr Leu Val Thr Val Ser Ser
            115                 120
```

<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 84

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
```

```
                    20                  25                  30

Asp Val Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Leu Ser Gly Asn Tyr Leu Thr Ser Phe Tyr Cys Asp Tyr
                100                 105                 110

Trp Gly Gln Gly Thr Leu Val Thr Val Ser Ser
            115                 120

<210> SEQ ID NO 85
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 85

Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
                    20                  25                  30

Asp Val Gly Val Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Leu Tyr Gly Asn Tyr Leu Arg Ser Tyr Tyr Cys Asp Tyr
                100                 105                 110

Trp Gly Gln Gly Thr Leu Val Thr Val Ser Ser
            115                 120

<210> SEQ ID NO 86
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 86

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Gly Thr Phe
                    20                  25                  30

Asp Leu Gly Ile Gly Trp Ile Arg Gln Pro Pro Gly Lys Ala Leu Glu
            35                  40                  45
```

```
Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
            115                 120
```

<210> SEQ ID NO 87
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 87

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Gly Thr Phe
                20                  25                  30

Asp Leu Gly Ile Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
            115                 120
```

<210> SEQ ID NO 88
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 88

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Gly Thr Phe
                20                  25                  30

Asp Leu Gly Ile Gly Trp Ile Arg Gln Pro Pro Gly Lys Ala Leu Glu
            35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80
```

```
Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 89

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 90
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 90

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
```

```
                 100                 105                 110

Trp Gly Gln Gly Thr Leu Val Thr Val Ser Ser
        115                 120

<210> SEQ ID NO 91
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 91

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 92
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 92

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120
```

<210> SEQ ID NO 93
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 93

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 94
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 94

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Met Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 95

Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
            115                 120

<210> SEQ ID NO 96
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 96

Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
            115                 120

<210> SEQ ID NO 97
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series -continued

<400> SEQUENCE: 97

Gln Val Thr Leu Lys Glu Ser Gly Pro Ala Leu Val Lys Pro Thr Gln
1               5                   10                  15

Thr Leu Thr Leu Thr Cys Thr Phe Ser Gly Ser Ser Leu Ser Thr Phe
            20                  25                  30

Asp Val Gly Val Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 98

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 99
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 99

Gln Val Thr Leu Lys Glu Ser Gly Pro Ala Leu Val Lys Pro Thr Gln
1               5                   10                  15

```
Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 100
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 100

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Gly Thr Phe
            20                  25                  30

Asp Leu Gly Ile Gly Trp Ile Arg Gln Pro Pro Gly Lys Ala Leu Glu
        35                  40                  45

Trp Leu Ala His Ile Trp Gly Asp Asp Asp Lys Tyr Tyr Asn Pro Ala
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
        115                 120

<210> SEQ ID NO 101
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 101

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Asp Leu Gly Ile Gly Trp Ile Arg Gln Pro Pro Gly Lys Ala Leu Glu
```

```
                      35                  40                  45

Trp Leu Ala His Ile Trp Gly Asp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Leu Tyr Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 102
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 102

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
                    20                  25                  30

Asp Leu Gly Ile Gly Trp Ile Arg Gln Pro Pro Gly Lys Ala Leu Glu
            35                  40                  45

Trp Leu Ala His Ile Trp Gly Asp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Leu Ser Gly Asn Tyr Leu Thr Ser Phe Tyr Cys Asp Tyr
            100                 105                 110

Trp Gly Gln Gly Thr Leu Val Thr Val Ser Ser
        115                 120

<210> SEQ ID NO 103
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MK1 series

<400> SEQUENCE: 103

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
                    20                  25                  30

Asp Leu Gly Ile Gly Trp Ile Arg Gln Pro Pro Gly Lys Ala Leu Glu
            35                  40                  45

Trp Leu Ala His Ile Trp Gly Asp Asp Asp Lys Tyr Tyr Asn Pro Ala
        50                  55                  60
```

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Leu Tyr Gly Asn Tyr Leu Arg Ser Tyr Tyr Cys Asp Tyr
            100                 105                 110

Trp Gly Gln Gly Thr Leu Val Thr Val Ser Ser
            115                 120
```

<210> SEQ ID NO 104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 104

```
Asp Val Val Met Thr Gln Ser Pro Ala Phe Leu Ser Val Thr Pro Gly
 1               5                  10                  15

Glu Lys Val Thr Ile Thr Cys Ser Ala Ser Ser Val Ser Tyr Met
             20                  25                  30

His Trp Tyr Gln Gln Lys Pro Asp Gln Ala Pro Lys Leu Leu Ile Lys
             35                  40                  45

Ala Thr Ser Asn Leu Ala Ser Gly Val Pro Ser Arg Phe Ser Gly Ser
         50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Gln Gly Thr Lys Leu Glu Ile Lys Arg
            100                 105
```

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 105

```
Asp Val Val Met Thr Gln Ser Pro Ala Phe Leu Ser Val Thr Pro Gly
 1               5                  10                  15

Glu Lys Val Thr Ile Thr Cys Ser Ala Ser Ser Val Ser Tyr Met
             20                  25                  30

His Trp Tyr Gln Gln Lys Pro Asp Gln Ala Pro Lys Leu Leu Ile Lys
             35                  40                  45

Ala Thr Ser Asn Leu Ala Ser Gly Val Pro Ser Arg Phe Ser Gly Ser
         50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Gln Gly Thr Lys Leu Glu Ile Lys Arg
            100                 105
```

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 106

```
Asp Val Val Met Thr Gln Ser Pro Ala Phe Leu Ser Val Thr Pro Gly
1               5                   10                  15

Glu Lys Val Thr Ile Thr Cys Ser Ala Ser Ser Val Ser Tyr Met
            20                  25                  30

His Trp Tyr Gln Gln Lys Pro Asp Gln Ala Pro Lys Leu Leu Ile Lys
            35                  40                  45

Ala Thr Ser Asn Leu Ala Ser Gly Val Pro Ser Arg Phe Ser Gly Ser
50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105
```

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 107

```
Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30

His Trp Tyr Gln Gln Lys Pro Asp Gln Ala Pro Lys Leu Leu Ile Lys
            35                  40                  45

Ala Thr Ser Asn Leu Ala Ser Gly Val Pro Ser Arg Phe Ser Gly Ser
50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105
```

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 108

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 109

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 110
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 110

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
            50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 111

Asp Val Val Met Thr Gln Ser Pro Ala Phe Leu Ser Val Thr Pro Gly
 1               5                  10                  15

Glu Lys Val Thr Ile Thr Cys Ser Ala Arg Ser Ser Val Ser Tyr Met
                20                  25                  30

His Trp Tyr Gln Gln Lys Pro Asp Gln Ala Pro Lys Leu Leu Ile Lys
            35                  40                  45

Ala Thr Ser Asn Leu Ala Ser Gly Val Pro Ser Arg Phe Ser Gly Ser
            50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 112

Asp Val Val Met Thr Gln Ser Pro Ala Phe Leu Ser Val Thr Pro Gly
 1               5                  10                  15

Glu Lys Val Thr Ile Thr Cys Ser Ala Arg Ser Ser Val Ser Tyr Met
                20                  25                  30

His Trp Tyr Gln Gln Lys Pro Asp Gln Ala Pro Lys Leu Leu Ile Lys
            35                  40                  45

Ala Thr Ser Asn Leu Ala Ser Gly Val Pro Ser Arg Phe Ser Gly Ser
            50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Light chain variable region of MK1 series

<400> SEQUENCE: 113

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Light chain variable region of MK1 series

<400> SEQUENCE: 114

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: Light chain variable region of MK1 series

<400> SEQUENCE: 115

Asp Val Val Met Thr Gln Ser Pro Ala Phe Leu Ser Val Thr Pro Gly
1               5                   10                  15

Glu Lys Val Thr Ile Thr Cys Arg Ala Ser Ser Val Ser Tyr Met
            20                  25                  30

His Trp Tyr Gln Gln Lys Pro Asp Gln Ala Pro Lys Leu Leu Ile Lys
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 116

Asp Val Val Met Thr Gln Ser Pro Ala Phe Leu Ser Val Thr Pro Gly
1               5                   10                  15

Glu Lys Val Thr Ile Thr Cys Ser Ala Ser Ser Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 117
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 117

Asp Val Val Met Thr Gln Ser Pro Ala Phe Leu Ser Val Thr Pro Gly
1               5                   10                  15

Glu Lys Val Thr Ile Thr Cys Ser Ala Ser Ser Val Ser Tyr Met
            20                  25                  30

His Trp Tyr Gln Gln Lys Pro Asp Gln Ala Pro Lys Leu Leu Ile Lys

```
                35                  40                  45
Trp Thr Ser Asp Arg Tyr Ser Gly Val Pro Ser Arg Phe Ser Gly Ser
    50                  55                  60
Gly Ser Gly Thr Asp Phe Thr Phe Thr Ile Ser Ser Leu Glu Ala Glu
65                  70                  75                  80
Asp Ala Ala Thr Tyr Tyr Cys Gln Gln Trp Ser Ser Asn Pro Leu Thr
                85                  90                  95
Phe Gly Gln Gly Thr Lys Leu Glu Ile Lys Arg
            100                 105
```

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 118

```
Asp Val Val Met Thr Gln Ser Pro Ala Phe Leu Ser Val Thr Pro Gly
1               5                   10                  15
Glu Lys Val Thr Ile Thr Cys Ser Ala Ser Ser Ser Val Ser Tyr Met
                20                  25                  30
His Trp Tyr Gln Gln Lys Pro Asp Gln Ala Pro Lys Leu Leu Ile Lys
            35                  40                  45
Trp Thr Ser Asp Arg Tyr Ser Gly Val Pro Ser Arg Phe Ser Gly Ser
    50                  55                  60
Gly Ser Gly Thr Asp Phe Thr Phe Thr Ile Ser Ser Leu Glu Ala Glu
65                  70                  75                  80
Asp Ala Ala Thr Tyr Tyr Cys Gln Gln His Leu His Ile Pro Tyr Thr
                85                  90                  95
Phe Gly Gln Gly Thr Lys Leu Glu Ile Lys Arg
            100                 105
```

<210> SEQ ID NO 119
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 119

```
Asp Val Val Met Thr Gln Ser Pro Ala Phe Leu Ser Val Thr Pro Gly
1               5                   10                  15
Glu Lys Val Thr Ile Thr Cys Ser Ala Ser Ser Arg Val Ser Tyr Met
                20                  25                  30
His Trp Tyr Gln Gln Lys Pro Asp Gln Ala Pro Lys Leu Leu Ile Lys
            35                  40                  45
Trp Thr Ser Asp Arg Tyr Ser Gly Val Pro Ser Arg Phe Ser Gly Ser
    50                  55                  60
Gly Ser Gly Thr Asp Phe Thr Phe Thr Ile Ser Ser Leu Glu Ala Glu
65                  70                  75                  80
Asp Ala Ala Thr Tyr Tyr Cys Gln Gln Trp Ser Ser Asn Pro Phe Thr
                85                  90                  95
```

```
Phe Gly Gln Gly Thr Lys Leu Glu Ile Lys Arg
            100                 105

<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 120

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 121
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 121

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: Light chain variable region of MK1 series

<400> SEQUENCE: 122

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 123

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 124

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
                35                  40                  45

Trp Thr Ser Asp Arg Tyr Ser Gly Val Pro Ser Arg Phe Ser Gly Ser
 50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
                100                 105

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 125

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
                20                  25                  30

His Trp Tyr Gln Gln Lys Pro Asp Gln Ala Pro Lys Leu Leu Ile Lys
                35                  40                  45

Trp Thr Ser Asp Arg Tyr Ser Gly Val Pro Ser Arg Phe Ser Gly Ser
 50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
                100                 105

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 126

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
                20                  25                  30

His Trp Tyr Gln Gln Lys Pro Asp Gln Ala Pro Lys Leu Leu Ile Lys
                35                  40                  45

Trp Thr Ser Asp Arg Tyr Ser Gly Val Pro Ser Arg Phe Ser Gly Ser
 50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

```
Phe Gly Gln Gly Thr Lys Leu Glu Ile Lys Arg
            100                 105

<210> SEQ ID NO 127
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 127

Asp Val Val Met Thr Gln Ser Pro Ala Phe Leu Ser Val Thr Pro Gly
1               5                   10                  15

Glu Lys Val Thr Ile Thr Cys Arg Ala Ser Ser Val Ser Tyr Met
            20                  25                  30

His Trp Tyr Gln Gln Lys Pro Asp Gln Ala Pro Lys Leu Leu Ile Lys
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 128
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 128

Asp Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 129
<211> LENGTH: 107
<212> TYPE: PRT
<213> ORGANISM: Artificial Sequence
<220> FEATURE:
<223> OTHER INFORMATION: Description of Artificial Sequence: Synthetic
```

```
                     polypeptide
<220> FEATURE:
<223> OTHER INFORMATION: Light chain variable region of MK1 series

<400> SEQUENCE: 129

Asp Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 130
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 130

Asp Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 131

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
            20                  25                  30
```

His Trp Tyr Gln Gln Lys Pro Asp Gln Ala Pro Lys Leu Leu Ile Lys
            35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
                100                 105

<210> SEQ ID NO 132
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 132

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
                20                  25                  30

His Trp Tyr Gln Gln Lys Pro Asp Gln Ala Pro Lys Leu Leu Ile Lys
            35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
                100                 105

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 133

Asp Val Val Met Thr Gln Ser Pro Ala Phe Leu Ser Val Thr Pro Gly
1               5                   10                  15

Glu Lys Val Thr Ile Thr Cys Ser Ala Ser Ser Arg Val Ser Tyr Met
                20                  25                  30

His Trp Tyr Gln Gln Lys Pro Asp Gln Ala Pro Lys Leu Leu Ile Lys
            35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr

-continued

```
                85                  90                  95

Phe Gly Gln Gly Thr Lys Leu Glu Ile Lys Arg
            100                 105

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 134

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 135

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
            100                 105

<210> SEQ ID NO 136
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Light chain variable region of MK1 series

<400> SEQUENCE: 136

Asp Val Val Met Thr Gln Ser Pro Ala Phe Leu Ser Val Thr Pro Gly
1               5                   10                  15

Glu Lys Val Thr Ile Thr Cys Ser Ala Arg Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
            100                 105

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 137

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
            20                  25                  30

His Trp Tyr Gln Gln Lys Pro Asp Gln Ala Pro Lys Leu Leu Ile Lys
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Phe Thr
                85                  90                  95

Phe Gly Gln Gly Thr Lys Leu Glu Ile Lys Arg
            100                 105

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 138

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met

```
                20                  25                  30

His Trp Tyr Gln Gln Lys Pro Asp Gln Ala Pro Lys Leu Leu Ile Lys
            35                  40                  45

Asp Thr Ser Lys Leu Ala Ser Gly Val Pro Ser Arg Phe Ser Gly Ser
        50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys Arg
                100                 105

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MK1 series

<400> SEQUENCE: 139

Asp Val Val Met Thr Gln Ser Pro Ala Phe Leu Ser Val Thr Pro Gly
1               5                   10                  15

Glu Lys Val Thr Ile Thr Cys Arg Ala Ser Ser Ser Val Ser Tyr Met
                20                  25                  30

His Trp Tyr Gln Gln Lys Pro Asp Gln Ala Pro Lys Leu Leu Ile Lys
            35                  40                  45

Asp Thr Ser Lys Leu Ala Ser Gly Val Pro Ser Arg Phe Ser Gly Ser
        50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln His Leu His Ile Pro Tyr Thr
                85                  90                  95

Phe Gly Gln Gly Thr Lys Leu Glu Ile Lys Arg
                100                 105

<210> SEQ ID NO 140
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 140

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
                20                  25                  30

Asp Met Gly Val Gly Trp Ile Arg Gln Pro Ser Gly Lys Gly Leu Glu
            35                  40                  45

Trp Leu Ala His Ile Trp Trp Asp Asp Lys Tyr Tyr Asn Pro Ala
        50                  55                  60

Leu Lys Ser Arg Leu Thr Ile Ser Lys Asp Thr Ser Lys Asn Gln Val
65                  70                  75                  80
```

```
Phe Leu Lys Ile Ala Asn Val Asp Thr Ala Asp Ser Ala Thr Tyr Tyr
                85                  90                  95
Cys Ala Arg Leu Tyr Gly Asn Tyr Leu Thr Ser Phe Tyr Cys Asp Tyr
            100                 105                 110
Trp Gly Gln Gly Thr Thr Leu Thr Val Ser Ser
        115                 120

<210> SEQ ID NO 141
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 141

Gln Val Thr Leu Lys Glu Ser Gly Pro Gly Ile Leu Gln Thr Ser Gln
1               5                   10                  15
Thr Leu Ser Leu Thr Cys Ser Phe Ser Gly Phe Ser Leu Ser Thr Phe
            20                  25                  30
Asp Met Gly Val Gly Trp Ile Arg Gln Pro Ser Gly Lys Gly Leu Glu
        35                  40                  45
Trp Leu Ala His Ile Trp Trp Asp Asp Asp Lys Tyr Tyr Asn Pro Ala
    50                  55                  60
Leu Lys Ser Arg Leu Thr Ile Ser Lys Asp Thr Ser Lys Asn Gln Val
65                  70                  75                  80
Phe Leu Lys Ile Ala Asn Val Asp Thr Ala Asp Ser Ala Thr Tyr Tyr
                85                  90                  95
Cys Ala Arg Leu Ser Gly Asn Tyr Leu Thr Ser Phe Tyr Cys Asp Tyr
            100                 105                 110
Trp Gly Gln Gly Thr Thr Leu Thr Val Ser Ser
        115                 120

<210> SEQ ID NO 142
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 142

Gln Val Thr Leu Lys Glu Ser Gly Pro Gly Ile Leu Gln Thr Ser Gln
1               5                   10                  15
Thr Leu Ser Leu Thr Cys Ser Phe Ser Gly Phe Ser Leu Ser Thr Phe
            20                  25                  30
Asp Met Gly Val Gly Trp Ile Arg Gln Pro Ser Gly Lys Gly Leu Glu
        35                  40                  45
Trp Leu Ala His Ile Trp Trp Asp Asp Asp Lys Tyr Tyr Asn Pro Ala
    50                  55                  60
Leu Lys Ser Arg Leu Thr Ile Ser Lys Asp Thr Ser Lys Asn Gln Val
65                  70                  75                  80
Phe Leu Lys Ile Ala Asn Val Asp Thr Ala Asp Ser Ala Thr Tyr Tyr
                85                  90                  95
Cys Ala Arg Leu Tyr Gly Asn Tyr Leu Arg Ser Tyr Tyr Cys Asp Tyr
            100                 105                 110
```

Trp Gly Gln Gly Thr Thr Leu Thr Val Ser Ser
        115                 120

<210> SEQ ID NO 143
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 143

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Ser Ser Leu Ser Thr Phe
            20                  25                  30

Asp Val Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 144
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 144

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Ser Ser Leu Ser Thr Phe
            20                  25                  30

Asp Val Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
        115                 120

```
<210> SEQ ID NO 145
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 145

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Ser Ser Leu Ser Thr Phe
            20                  25                  30

Asp Val Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 146
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 146

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 147
<211> LENGTH: 123
<212> TYPE: PRT
<213> ORGANISM: Artificial Sequence
<220> FEATURE:
```

-continued

<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 147

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 148
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 148

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Thr Leu Thr Val Ser Ser
        115                 120

<210> SEQ ID NO 149
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 149

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 150
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 150

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
        115                 120

<210> SEQ ID NO 151
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 151

Gln Val Thr Leu Lys Glu Ser Gly Pro Gly Ile Leu Gln Thr Ser Gln
1               5                   10                  15

```
Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ala
 50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Arg Ser Tyr Tyr Cys Asp Tyr
                100                 105                 110

Trp Gly Gln Gly Thr Thr Leu Thr Val Ser Ser
            115                 120

<210> SEQ ID NO 152
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 152

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Met Gly Val Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
 50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
                100                 105                 110

Trp Gly Gln Gly Thr Thr Leu Thr Val Ser Ser
            115                 120

<210> SEQ ID NO 153
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 153

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Met Gly Val Gly Trp Ile Arg Gln Pro Ser Gly Lys Gly Leu Glu
        35                  40                  45
```

```
Trp Leu Ala His Ile Trp Gly Asp Asp Lys Tyr Tyr Asn Pro Ala
        50                  55                  60

Leu Lys Ser Arg Leu Thr Ile Ser Lys Asp Thr Ser Lys Asn Gln Val
 65                  70                  75                  80

Phe Leu Lys Ile Ala Asn Val Asp Thr Ala Asp Ser Ala Thr Tyr Tyr
                 85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
            115                 120

<210> SEQ ID NO 154
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 154

Gln Val Thr Leu Lys Glu Ser Gly Pro Gly Ile Leu Gln Thr Ser Gln
 1               5                  10                  15

Thr Leu Ser Leu Thr Cys Ser Phe Ser Gly Phe Ser Leu Ser Thr Phe
                20                  25                  30

Asp Met Gly Val Gly Trp Ile Arg Gln Pro Ser Gly Lys Gly Leu Glu
            35                  40                  45

Trp Leu Ala His Ile Trp Gly Asp Asp Lys Tyr Tyr Asn Pro Ala
        50                  55                  60

Leu Lys Ser Arg Leu Thr Ile Ser Lys Asp Thr Ser Lys Asn Gln Val
 65                  70                  75                  80

Phe Leu Lys Ile Ala Asn Val Asp Thr Ala Asp Ser Ala Thr Tyr Tyr
                 85                  90                  95

Cys Ala Arg Leu Tyr Gly Asn Tyr Leu Arg Ser Tyr Tyr Cys Asp Tyr
            100                 105                 110

Trp Gly Gln Gly Thr Thr Leu Thr Val Ser Ser
            115                 120

<210> SEQ ID NO 155
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 155

Gln Val Thr Leu Lys Glu Ser Gly Pro Gly Ile Leu Gln Thr Ser Gln
 1               5                  10                  15

Thr Leu Ser Leu Thr Cys Ser Phe Ser Gly Ser Ser Leu Ser Thr Phe
                20                  25                  30

Asp Val Gly Val Gly Trp Ile Arg Gln Pro Ser Gly Lys Gly Leu Glu
            35                  40                  45

Trp Leu Ala His Ile Trp Gly Asp Asp Lys Tyr Tyr Asn Pro Ala
        50                  55                  60

Leu Lys Ser Arg Leu Thr Ile Ser Lys Asp Thr Ser Lys Asn Gln Val
```

```
                65                  70                  75                  80
Phe Leu Lys Ile Ala Asn Val Asp Thr Ala Asp Ser Ala Thr Tyr Tyr
                    85                  90                  95

Cys Ala Arg Leu Tyr Gly Asn Tyr Leu Thr Ser Phe Tyr Cys Asp Tyr
                100                 105                 110

Trp Gly Gln Gly Thr Thr Leu Thr Val Ser Ser
        115                 120

<210> SEQ ID NO 156
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 156

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Ser Ser Leu Ser Thr Phe
            20                  25                  30

Asp Val Gly Val Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                    85                  90                  95

Cys Ala Arg Leu Ser Gly Asn Tyr Leu Thr Ser Phe Tyr Cys Asp Tyr
                100                 105                 110

Trp Gly Gln Gly Thr Thr Leu Thr Val Ser Ser
        115                 120

<210> SEQ ID NO 157
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 157

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Ser Ser Leu Ser Thr Phe
            20                  25                  30

Asp Val Gly Val Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                    85                  90                  95
```

```
Cys Ala Arg Leu Tyr Gly Asn Tyr Leu Arg Ser Tyr Tyr Cys Asp Tyr
            100                 105                 110

Trp Gly Gln Gly Thr Thr Leu Thr Val Ser Ser
        115                 120
```

<210> SEQ ID NO 158
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 158

```
Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
            100                 105                 110

Trp Gly Gln Gly Thr Thr Leu Thr Val Ser Ser
        115                 120
```

<210> SEQ ID NO 159
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 159

```
Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
        115                 120
```

<210> SEQ ID NO 160
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 160

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Gly Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Arg Ser Tyr Tyr Cys Asp Tyr
                100                 105                 110

Trp Gly Gln Gly Thr Thr Leu Thr Val Ser Ser
            115                 120

<210> SEQ ID NO 161
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy chain variable region of MZ-2 series

<400> SEQUENCE: 161

Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Thr Ser Phe Tyr Cys Asp Tyr
                100                 105                 110

Trp Gly Gln Gly Thr Thr Leu Thr Val Ser Ser
            115                 120

<210> SEQ ID NO 162
<211> LENGTH: 123
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Heavy chain variable region of MZ-2 series

<400> SEQUENCE: 162

```
Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Ser Gly Asn Tyr Leu Thr Ser Phe Tyr Cys Asp Tyr
            100                 105                 110

Trp Gly Gln Gly Thr Thr Leu Thr Val Ser Ser
        115                 120
```

<210> SEQ ID NO 163
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Heavy chain variable region of MZ-2 series

<400> SEQUENCE: 163

```
Gln Val Thr Leu Lys Glu Ser Gly Pro Gly Ile Leu Gln Thr Ser Gln
1               5                   10                  15

Thr Leu Ser Leu Thr Cys Ser Phe Ser Gly Phe Ser Leu Ser Thr Phe
            20                  25                  30

Asp Leu Gly Ile Gly Trp Ile Arg Gln Pro Ser Gly Lys Gly Leu Glu
        35                  40                  45

Trp Leu Ala His Ile Trp Gly Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Ser Ala Thr Tyr Tyr
                85                  90                  95

Cys Ala Arg Leu Tyr Gly Asn Tyr Leu Arg Ser Tyr Tyr Cys Asp Tyr
            100                 105                 110

Trp Gly Gln Gly Thr Thr Leu Thr Val Ser Ser
        115                 120
```

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide
<220> FEATURE:

<223> OTHER INFORMATION: Light chain variable region of MZ-2 series

<400> SEQUENCE: 164

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 165

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 166
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 166

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr

```
                    35                  40                  45

Ala Thr Ser Asn Leu Ala Ser Gly Val Pro Ala Arg Phe Gly Ser
                50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
                100                 105

<210> SEQ ID NO 167
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 167

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
                20                  25                  30

His Trp Tyr Gln Gln Lys Ser Gly Thr Ser Pro Lys Arg Trp Ile Tyr
                35                  40                  45

Ala Thr Ser Asn Leu Ala Ser Gly Val Pro Ala Arg Phe Ser Gly Ser
                50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
                100                 105

<210> SEQ ID NO 168
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 168

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
                20                  25                  30

His Trp Tyr Gln Gln Lys Ser Gly Thr Ser Pro Lys Arg Trp Ile Tyr
                35                  40                  45

Ala Thr Ser Asn Leu Ala Ser Gly Val Pro Ala Arg Phe Ser Gly Ser
                50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95
```

```
Phe Gly Ala Gly Thr Lys Leu Glu Leu Lys Arg
            100                 105
```

<210> SEQ ID NO 169
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 169

```
Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105
```

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 170

```
Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105
```

<210> SEQ ID NO 171
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Light chain variable region of MZ-2 series

<400> SEQUENCE: 171

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 172
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 172

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 173

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Ser Gly Thr Ser Pro Lys Arg Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 174
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 174

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Ser Gly Thr Ser Pro Lys Arg Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 175
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 175

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Ser Gly Thr Ser Pro Lys Arg Trp Ile Tyr
            35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

```
Phe Gly Ala Gly Thr Lys Leu Glu Leu Lys Arg
            100                 105

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 176

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
            35                  40                  45

Trp Thr Ser Asp Arg Tyr Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 177

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
            35                  40                  45

Trp Thr Ser Asp Arg Tyr Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 178
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued

```
        polypeptide
<220> FEATURE:
<223> OTHER INFORMATION: Light chain variable region of MZ-2 series

<400> SEQUENCE: 178

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 179
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 179

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 180

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30
```

```
His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 181
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 181

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 182
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 182

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
```

```
                85                  90                  95

Phe Gly Ala Gly Thr Lys Leu Glu Leu Lys Arg
            100                 105

<210> SEQ ID NO 183
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 183

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 184
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 184

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 185
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 185

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 186

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Ser Gly Thr Ser Pro Lys Arg Trp Ile Tyr
        35                  40                  45

Trp Thr Ser Asp Arg Tyr Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 187
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 187

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Ser Val Ser Tyr Met

```
                20                  25                  30
His Trp Tyr Gln Gln Lys Ser Gly Thr Ser Pro Lys Arg Trp Ile Tyr
            35                  40                  45

Trp Thr Ser Asp Arg Tyr Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 188
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 188

Gln Ile Val Leu Thr Gln Ser Pro Ala Ile Val Ser Ala Ser Pro Gly
 1               5                  10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Asn Pro Phe Thr
                85                  90                  95

Phe Gly Ala Gly Thr Lys Leu Glu Leu Lys Arg
            100                 105

<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 189

Gln Ile Val Leu Thr Gln Ser Pro Ala Ile Val Ser Ala Ser Pro Gly
 1               5                  10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80
```

-continued

```
Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 190
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 190

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 191
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 191

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ala Gly Thr Lys Leu Glu Leu Lys Arg
            100                 105

<210> SEQ ID NO 192
<211> LENGTH: 107
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 192

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 193
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 193

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Arg Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 194

Gln Ile Val Leu Thr Gln Ser Pro Ala Ile Val Ser Ala Ser Pro Gly
1               5                   10                  15
```

```
Glu Lys Val Thr Met Thr Cys Ser Ala Arg Ser Ser Val Ser Tyr Met
             20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Phe Thr
                 85                  90                  95

Phe Gly Ala Gly Thr Lys Leu Glu Leu Lys Arg
            100                 105
```

<210> SEQ ID NO 195
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 195

```
Gln Ile Val Leu Thr Gln Ser Pro Ala Ile Val Ser Ala Ser Pro Gly
 1               5                   10                  15

Glu Lys Val Thr Met Thr Cys Ser Ala Arg Ser Ser Val Ser Tyr Met
             20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Arg
            100                 105
```

<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 196

```
Gln Ile Val Leu Thr Gln Ser Pro Ala Ile Val Ser Ala Ser Pro Gly
 1               5                   10                  15

Glu Lys Val Thr Met Thr Cys Ser Ala Arg Ser Ser Val Ser Tyr Met
             20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80
```

Asp Ala Ala Thr Tyr Tyr Cys Gln Gln His Leu His Ile Pro Tyr Thr
            85                  90                  95

Phe Gly Ala Gly Thr Lys Leu Glu Leu Lys Arg
            100                 105

<210> SEQ ID NO 197
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 197

Gln Ile Val Leu Thr Gln Ser Pro Ala Ile Val Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Phe Thr
            85                  90                  95

Phe Gly Ala Gly Thr Lys Leu Glu Leu Lys Arg
            100                 105

<210> SEQ ID NO 198
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 198

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys Arg
            100                 105

<210> SEQ ID NO 199
<211> LENGTH: 107
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of MZ-2 series

<400> SEQUENCE: 199

Gln Ile Val Leu Thr Gln Ser Pro Ala Ile Val Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln His Leu His Ile Pro Tyr Thr
                85                  90                  95

Phe Gly Ala Gly Thr Lys Leu Glu Leu Lys Arg
            100                 105

<210> SEQ ID NO 200
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 200

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 201
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 201

Glu Ile Gln Met Thr Gln Ser Pro Ser Ser Leu Ser Ala Ser Val Gly
1               5                   10                  15
```

-continued

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 202
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 202

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 203
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 203

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
50                  55                  60

Gly Ser Gly Thr Asp Phe Thr Leu Thr Ile Ser Ser Leu Gln Pro Glu

```
                65                  70                  75                  80
Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
                100                 105

<210> SEQ ID NO 204
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 204

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
                100                 105

<210> SEQ ID NO 205
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 205

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
                100                 105

<210> SEQ ID NO 206
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 206

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 207
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 207

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 208
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 208

Glu Ile Gln Met Thr Gln Ser Pro Ser Ser Leu Ser Ala Ser Val Gly
```

```
                1               5                  10                 15
Asp Arg Val Thr Ile Thr Cys Ser Ala Arg Ser Ser Val Ser Tyr Met
                20                     25                 30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
                100                 105
```

<210> SEQ ID NO 209
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 209

```
Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
                20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
                100                 105
```

<210> SEQ ID NO 210
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 210

```
Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
                20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60
```

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 211
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 211

Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
                20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 212
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 212

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Gln Gln Lys Pro Gly Lys Ala Pro Lys Leu Leu Ile Tyr
            35                  40                  45

Trp Thr Ser Asp Arg Tyr Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 213

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 213

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 214
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 214

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 215
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 215
```

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 216

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 217
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 217

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 218

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Tyr Gln Gln Lys Pro Gly Lys Ala Pro Lys Leu Leu Ile Tyr
            35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 219
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 219

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
                20                  25                  30

His Trp Tyr Gln Gln Lys Pro Gly Lys Ala Pro Lys Leu Leu Ile Tyr
            35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

```
<210> SEQ ID NO 220
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 220

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 221
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 221

Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 222
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 222
```

```
Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
                35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Asn Pro Leu Thr
                85                  90                  95

Phe Gly Gly Gly Thr Lys Leu Glu Ile Lys Arg
            100                 105
```

<210> SEQ ID NO 223
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 223

```
Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
                35                  40                  45

Trp Thr Ser Asp Arg Tyr Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105
```

<210> SEQ ID NO 224
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 224

```
Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
```

```
                50                  55                  60
Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gly Gly Thr Lys Leu Glu Ile Lys Arg
                100                 105

<210> SEQ ID NO 225
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 225

Glu Ile Gln Met Thr Gln Ser Pro Ser Ser Leu Ser Ala Ser Val Gly
  1               5                  10                  15

Asp Arg Val Thr Ile Thr Cys Ser Ala Ser Ser Val Ser Tyr Met
                 20                  25                  30

His Trp Tyr Gln Gln Lys Pro Gly Lys Ala Pro Lys Leu Leu Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln Trp Ser Ser Asn Pro Leu Thr
                 85                  90                  95

Phe Gly Gly Gly Thr Lys Leu Glu Ile Lys Arg
                100                 105

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 226

Glu Ile Gln Met Thr Gln Ser Pro Ser Ser Leu Ser Ala Ser Val Gly
  1               5                  10                  15

Asp Arg Val Thr Ile Thr Cys Ser Ala Ser Ser Val Ser Tyr Met
                 20                  25                  30

His Trp Tyr Gln Gln Lys Pro Gly Lys Ala Pro Lys Leu Leu Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln His Leu His Ile Pro Tyr Thr
                 85                  90                  95

Phe Gly Gly Gly Thr Lys Leu Glu Ile Lys Arg
                100                 105
```

<210> SEQ ID NO 227
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable region of hMZ-2 series

<400> SEQUENCE: 227

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 228
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable region of hMZ-2 series

<400> SEQUENCE: 228

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 229
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Light chain variable region of hMZ-2 series

<400> SEQUENCE: 229

Glu Ile Gln Met Thr Gln Ser Pro Ser Ser Leu Ser Ala Ser Val Gly
1               5                   10                  15

Asp Arg Val Thr Ile Thr Cys Ser Ala Ser Ser Arg Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 230
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 230

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
            100                 105

<210> SEQ ID NO 231
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 231

Glu Ile Gln Met Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

```
Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
                100                 105

<210> SEQ ID NO 232
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 232

Glu Ile Gln Met Thr Gln Ser Pro Ser Ser Leu Ser Ala Ser Val Gly
 1               5                  10                  15

Asp Arg Val Thr Ile Thr Cys Ser Ala Arg Ser Ser Val Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
                100                 105

<210> SEQ ID NO 233
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 233

Glu Ile Gln Met Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Ile Ala Thr Tyr Tyr Cys Gln Gln Trp Ser Ser Asn Pro Phe Thr
                85                  90                  95

Phe Gly Gly Gly Thr Lys Leu Glu Ile Lys Arg
                100                 105
```

<210> SEQ ID NO 234
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 234

Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65              70                  75                  80

Asp Ile Ala Thr Tyr Tyr Cys Gln Gln Trp Ser Ser Asn Pro Leu Thr
                85                  90                  95

Phe Gly Gly Gly Thr Lys Leu Glu Ile Lys Arg
            100                 105

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light chain variable region of hMZ-2 series

<400> SEQUENCE: 235

Glu Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Leu Leu Ile Tyr
                35                  40                  45

Asp Thr Ser Lys Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65              70                  75                  80

Asp Ile Ala Thr Tyr Tyr Cys Gln Gln His Leu His Ile Pro Tyr Thr
                85                  90                  95

Phe Gly Gly Gly Thr Lys Leu Glu Ile Lys Arg
            100                 105

<210> SEQ ID NO 236
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Nucleotides of MZ-2 heavy chain variable region

<400> SEQUENCE: 236

```
caggttactc tgaaagagtc tggccctggg atattgcaga cctcccagac cctcagtctg    60
acttgttctt tctctgggtt ttcactgggc acttttgatt tgggtatagg ctggattcgt   120
cagccttcag ggaagggtct ggagtggctg gcgcacatct ggtgggatga tgataagtac   180
tataatccag ccctgaagag tcggctcaca atctccaagg atacctccaa aaaccaggta   240
ttcctcaaga tcgccaatgt ggacactgca gactctgcca catattactg tgctcggctc   300
tctggaaaact acctcacgtc gttctactgt gactactggg gccaaggcac cactctcaca   360
gtgtcctca                                                           369
```

<210> SEQ ID NO 237
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Nucleotides of light chain variable region

<400> SEQUENCE: 237

```
caaattgttc tcacccagtc tccagcaatc gtgtctgcat ctccagggga aaggtcacc    60
atgacctgca gtgccagatc aagtgtaagt tatatgcact ggtaccagca gaagtcaggc   120
acctccccca aaagatggat ttatgacaca tccaaactgg cttctggagt ccctgctcgc   180
ttcagtggca gtgggtctgg gacctcttat tctctcacaa tcagcagcat ggaggctgaa   240
gacgctgcca cttattactg ccagcagtgg agtagtaatc cactcacgtt cggtgctggg   300
accaagctgg aactgaaacg g                                            321
```

<210> SEQ ID NO 238
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: Any naturally occurring amino acid

<400> SEQUENCE: 238

```
Ala Lys Xaa Val Ala Ala Trp Thr Leu Lys Ala Ala Ala
1               5                   10
```

<210> SEQ ID NO 239
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: misc_feature
<222> LOCATION: (26)..(37)
<223> OTHER INFORMATION: This region may encompass "Gly Phe Ser Leu Ser Thr Phe Asp Met Gly Val Gly," "Gly Ser Ser Leu Ser Thr Phe Asp Val Gly Val Gly," "Gly Phe Ser Leu Gly Thr Phe Asp Leu Gly Ile Gly" or "Gly Phe Ser Leu Ser Thr Phe Asp Leu Gly Ile Gly"
<220> FEATURE:
<221> NAME/KEY: misc_feature
<222> LOCATION: (52)..(64)
<223> OTHER INFORMATION: This region may encompass "His Ile Trp Trp Asp

```
        Asp Asp Lys Tyr Tyr Asn Pro Ala" or "His Ile Trp Gly Asp Asp Asp
        Lys Tyr Tyr Asn Pro Ala"
<220> FEATURE:
<221> NAME/KEY: misc_feature
<222> LOCATION: (100)..(112)
<223> OTHER INFORMATION: This region may encompass "Leu Tyr Gly Asn Tyr
        Leu Thr Ser Phe Tyr Cys Asp Tyr," "Leu Ser Gly Asn Tyr Leu Thr Ser
        Phe Tyr Cys Asp Tyr" or "Leu Tyr Gly Asn Tyr Leu Arg Ser Tyr Tyr
        Cys Asp Tyr"

<400> SEQUENCE: 239

Gln Ile Thr Leu Lys Glu Ser Gly Pro Thr Leu Val Lys Pro Thr Gln
1               5                   10                  15

Thr Leu Thr Leu Thr Cys Thr Phe Ser Xaa Xaa Xaa Xaa Xaa Xaa Xaa
            20                  25                  30

Xaa Xaa Xaa Xaa Xaa Trp Ile Arg Gln Pro Pro Gly Lys Ala Leu Glu
        35                  40                  45

Trp Leu Ala Xaa Xaa Xaa Xaa Xaa Xaa Xaa Xaa Xaa Xaa Xaa Xaa Xaa
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Xaa Xaa Xaa Xaa Xaa Xaa
            100                 105                 110

Trp Gly Gln Gly Thr Leu Val Thr Val Ser Ser
            115                 120

<210> SEQ ID NO 240
<211> LENGTH: 107
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: misc_feature
<222> LOCATION: (24)..(33)
<223> OTHER INFORMATION: This region may encompass "Ser Ala Ser Ser Ser
        Val Ser Tyr Met His," "Ser Ala Ser Ser Arg Val Ser Tyr Met His,"
        "Ser Ala Arg Ser Ser Val Ser Tyr Met His" or "Arg Ala Ser Ser Ser
        Val Ser Tyr Met His"
<220> FEATURE:
<221> NAME/KEY: misc_feature
<222> LOCATION: (49)..(55)
<223> OTHER INFORMATION: This region may encompass "Ala Thr Ser Asn Leu
        Ala Ser," "Trp Thr Ser Asp Arg Tyr Ser" or "Asp Thr Ser Lys Leu
        Ala Ser"
<220> FEATURE:
<221> NAME/KEY: misc_feature
<222> LOCATION: (88)..(96)
<223> OTHER INFORMATION: This region may encompass "Gln Gln Trp Ser Ser
        Asn Pro Phe Thr," "Gln Gln Trp Ser Ser Asn Pro Leu Thr" or "Gln
        Gln His Leu His Ile Pro Tyr Thr"

<400> SEQUENCE: 240

Glu Ile Val Leu Thr Gln Ser Pro Ser Ser Leu Ser Ala Ser Val Gly
1               5                   10                  15

Asp Arg Val Thr Ile Thr Cys Xaa Xaa Xaa Xaa Xaa Xaa Xaa Xaa Xaa
            20                  25                  30

Xaa Trp Tyr Gln Gln Lys Pro Gly Lys Ala Pro Lys Leu Leu Ile Tyr
        35                  40                  45

Xaa Xaa Xaa Xaa Xaa Xaa Xaa Gly Val Pro Ser Arg Phe Ser Gly Ser
50                  55                  60

Gly Ser Gly Thr Asp Phe Thr Phe Thr Ile Ser Ser Leu Gln Pro Glu
```

```
                65                  70                  75                  80
Asp Ile Ala Thr Tyr Tyr Cys Xaa Xaa Xaa Xaa Xaa Xaa Xaa Xaa
                    85                  90                  95

Phe Gly Gly Gly Thr Lys Leu Glu Ile Lys Arg
            100                 105
```

<210> SEQ ID NO 241
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (26)..(37)
<223> OTHER INFORMATION: This region may encompass "Gly Phe Ser Leu Ser
      Thr Phe Asp Met Gly Val Gly," "Gly Ser Ser Leu Ser Thr Phe Asp Val
      Gly Val Gly," "Gly Phe Ser Leu Gly Thr Phe Asp Leu Gly Ile Gly" or
      "Gly Phe Ser Leu Ser Thr Phe Asp Leu Gly Ile Gly"
<220> FEATURE:
<221> NAME/KEY: misc_feature
<222> LOCATION: (52)..(64)
<223> OTHER INFORMATION: This region may encompass "His Ile Trp Trp Asp
      Asp Asp Lys Tyr Tyr Asn Pro Ala" or "His Ile Trp Gly Asp Asp Asp
      Lys Tyr Tyr Asn Pro Ala"
<220> FEATURE:
<221> NAME/KEY: misc_feature
<222> LOCATION: (100)..(112)
<223> OTHER INFORMATION: This region may encompass "Leu Tyr Gly Asn Tyr
      Leu Thr Ser Phe Tyr Cys Asp Tyr," "Leu Ser Gly Asn Tyr Leu Thr Ser
      Phe Tyr Cys Asp Tyr" or "Leu Tyr Gly Asn Tyr Leu Arg Ser Tyr Tyr
      Cys Asp Tyr"

<400> SEQUENCE: 241

```
Gln Val Thr Leu Lys Glu Ser Gly Pro Ala Leu Val Lys Pro Thr Gln
1               5                   10                  15

Thr Leu Thr Leu Thr Cys Thr Phe Ser Xaa Xaa Xaa Xaa Xaa Xaa
                20                  25                  30

Xaa Xaa Xaa Xaa Xaa Trp Ile Arg Gln Pro Pro Gly Lys Ala Leu Glu
            35                  40                  45

Trp Leu Ala Xaa Xaa Xaa Xaa Xaa Xaa Xaa Xaa Xaa Xaa Xaa Xaa
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Xaa Xaa Xaa Xaa Xaa Xaa Xaa Xaa Xaa Xaa Xaa Xaa
                100                 105                 110

Trp Gly Gln Gly Thr Leu Val Thr Val Ser Ser
        115                 120
```

<210> SEQ ID NO 242
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (24)..(33)
<223> OTHER INFORMATION: This region may encompass "Ser Ala Ser Ser Ser
      Val Ser Tyr Met His," "Ser Ala Ser Ser Arg Val Ser Tyr Met His,"
      "Ser Ala Arg Ser Ser Val Ser Tyr Met His" or "Arg Ala Ser Ser Ser
      Val Ser Tyr Met His"
<220> FEATURE:

```
<221> NAME/KEY: misc_feature
<222> LOCATION: (49)..(55)
<223> OTHER INFORMATION: This region may encompass "Ala Thr Ser Asn Leu
      Ala Ser," "Trp Thr Ser Asp Arg Tyr Ser" or "Asp Thr Ser Lys Leu
      Ala Ser"
<220> FEATURE:
<221> NAME/KEY: misc_feature
<222> LOCATION: (88)..(96)
<223> OTHER INFORMATION: This region may encompass "Gln Gln Trp Ser Ser
      Asn Pro Phe Thr," "Gln Gln Trp Ser Ser Asn Pro Leu Thr" or "Gln
      Gln His Leu His Ile Pro Tyr Thr"

<400> SEQUENCE: 242

Asp Val Val Met Thr Gln Ser Pro Ala Phe Leu Ser Val Thr Pro Gly
1               5                   10                  15

Glu Lys Val Thr Ile Thr Cys Xaa Xaa Xaa Xaa Xaa Xaa Xaa Xaa
            20                  25                  30

Xaa Trp Tyr Gln Gln Lys Pro Asp Gln Ala Pro Lys Leu Leu Ile Lys
        35                  40                  45

Xaa Xaa Xaa Xaa Xaa Xaa Xaa Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Xaa Xaa Xaa Xaa Xaa Xaa Xaa Xaa Xaa
                85                  90                  95

Phe Gly Gln Gly Thr Lys Leu Glu Ile Lys Arg
                100                 105
```